(12) United States Patent
Twite et al.

(10) Patent No.: US 10,744,207 B2
(45) Date of Patent: Aug. 18, 2020

(54) BIOLOGICAL COMPLEXES AND METHODS FOR USING SAME

(71) Applicant: ACEPODIA, INC., Grand Cayman (KY)

(72) Inventors: Amy A. Twite, Berkeley (CA); Ching-Wen Hsiao, Castro Valley, CA (US); Sonny Hsiao, Oakland, CA (US); Cheng Liu, Oakland, CA (US); Hong Liu, El Sobrante, CA (US)

(73) Assignee: ACEPODIA, INC., Grand Cayman (KY)

( * ) Notice: Subject to any disclaimer, the term of this patent is extended or adjusted under 35 U.S.C. 154(b) by 614 days.

(21) Appl. No.: 15/528,245

(22) PCT Filed: May 1, 2015

(86) PCT No.: PCT/US2015/028951
§ 371 (c)(1),
(2) Date: May 19, 2017

(87) PCT Pub. No.: WO2015/168656
PCT Pub. Date: Nov. 5, 2015

(65) Prior Publication Data
US 2018/0133341 A1     May 17, 2018

Related U.S. Application Data

(60) Provisional application No. 61/988,070, filed on May 2, 2014.

(51) Int. Cl.
*A61K 47/69* (2017.01)
*A61K 47/68* (2017.01)
*C12N 5/07* (2010.01)
*C12N 15/85* (2006.01)

(52) U.S. Cl.
CPC ...... *A61K 47/6901* (2017.08); *A61K 47/6867* (2017.08); *C12N 5/06* (2013.01); *C12N 15/85* (2013.01)

(58) Field of Classification Search
CPC .................................................. A61K 47/6901
See application file for complete search history.

(56) References Cited

U.S. PATENT DOCUMENTS

| | | | | |
|---|---|---|---|---|
| 2012/0142088 A1* | 6/2012 | Hsiao | ................ | A61K 47/6901 435/325 |
| 2013/0344094 A1* | 12/2013 | Gerg | ..................... | C07K 16/00 424/179.1 |

OTHER PUBLICATIONS

Borisenko et al. (Nucleic Acids Research, 2009; 37(4). e28: 1-11). (Year: 2009).*

* cited by examiner

*Primary Examiner* — Scott Long
(74) *Attorney, Agent, or Firm* — Muncy, Geissler, Olds & Lowe, P.C.

(57) ABSTRACT

The disclosure provides complexes comprising targeting units, methods for their production, and methods for their use. In some embodiments, complexes comprise therapeutic agents complexed with targeting units. In some embodiments, complexes comprise cells complexed with targeting units. In view of the foregoing, there is a need for improved modalities for targeting of therapeutics, in the area of immunotherapy and others. The present disclosure addresses these needs, and provides additional advantages as well.

74 Claims, 41 Drawing Sheets

Unmodified T cells (orange cells) mixed with Jeko lymphoma cells (green cells) and shake at r.t. for 30hr..

Rit-T cells (orange cells) mixed with Jeko lymphoma cells (green cells) and shake at r.t. for 30hr..

M2 FAM DNA conjugate with Rituxan Antibody

Lane 1 → Rituxan

Lane 2 → Rituxan + M2 FAM

After DNA conjugate with Rituxan for 1 hr, the molecular weight increased as seen in lane 2, showing that >50% of the conjugation has 1 modification on antibody heavy chains. Antibody : DNA = 1 : 30 concentration Anti-CD20-T cells were added into targeted cells Jeko and Raji (CD20 positive) and control cells Jurkat (CD20 negative), and shake at r.t. for 1 hr. Place in 37 for 4 hrs.
Unmodifided T cells were added into targeted cells Jeko and Raji (CD20 positive) and control cells Jurkat (CD20 negative), and shake at r.t. for 1 hr. Place in 37 for 4 hrs.
Y axis: killing percentage. X axis: T cells to target cells ratio.

BIOLOGICAL COMPLEXES AND METHODS FOR USING SAME

CROSS-REFERENCE

This application claims the benefit of U.S. Provisional Application No. 61/988,070, which application is incorporated herein by reference.

BACKGROUND OF THE INVENTION

Inefficient targeting of therapeutics is associated with side-effects from off-target activity, and/or poor if any therapeutic efficacy. One area in which targeting is particularly important is immunotherapy, which holds promise as a treatment modality for cancer and infectious disease, among others. Conventional immunotherapy generally involves activating or augmenting a subject's immune system to recognize or more effectively respond to a disease agent. Current approaches include the isolation, activation, expansion, and reintroduction of a subject's T-cells. However, this entire process is both laborious and time-consuming. Cell-expansion processes are limited by the number of cells in a starting sample that recognize a target of interest, if T-cells can even be made to recognize the target in the first place. Expansion to a therapeutically relevant population of target-specific T-cells from a single clone may take months. Moreover, the need for relatively short-lived accessory cells in this process imposes the further need for a replenishing source of such cells, and is accompanied by an increased risk of contamination, such as in the case when the accessory cells carry a virus. Limitations such as these reduce the potential of immunotherapy to treat various conditions, such as cancer.

There are about 200 different types of cancer. Cancers can start in any type of body tissue and can metastasize from one body tissue to another. There are many different causes of cancer and these include; carcinogens, age, genetic mutations, immune system problems, diet, weight, lifestyle, environmental factors such as pollutants, some viruses for example the human papilloma virus (HPV) is implicated in cervical cancer and some bacterial infections are also known to cause cancers. There are many different treatment options for cancer and the treatment sought is often determined by the type and stage of the cancer. Treatment options include; chemotherapeutic drug treatment, hormonal drug treatment, radiotherapy, surgery, complementary therapies and combinations thereof. However, some cancers still have poor prognosis and treatment options.

Acute myeloid leukemia (AML), for example, is the most common type of leukemia in adults, with more than 12,000 new AML cases being reported each year and 9,000 associated deaths occurring annually in the United States. Surgery and radiation therapy have very limited roles in the treatment of this type of cancer because the leukemia cells spread widely throughout the bone marrow and to many other organs. With appropriate induction and consolidation therapy, 60%-70% of adults with AML can be expected to achieve a complete remission. However, the remission tends to be shorter in older patients and relapse is common. Patients with relapsed leukemia have an especially poor prognosis, with a long term disease-free survival rate of only 5-10% without hematopoietic stem cell transplantation. There is currently no standard treatment for patients with relapsed AML, but for a time the most promising drug was a monoclonal antibody drug conjugate, Gemtuzumab. This drug was approved by FDA in 2000 as a single agent for AML patients over 60 years of age who were experiencing their first relapse, or those who were not considered candidates for standard chemotherapy. Unfortunately, Gemtuzumab failed to show evidence of efficacy in the post-approval trial, and was associated with significant hepatotoxicity. It was later withdrawn from the market in 2010. This currently limits the treatment options for relapsed AML patients to hematopoietic stem cell transplants (if one has not already been performed), arsenic trioxide (for the acute promyelocytic leukemia subtype only), participation in clinical trials, or palliative care.

Typical cell-based immunotherapy alternative approaches involve generating immune cells (activated T cells or natural killer cells) that can circulate long enough in patients to engage and destroy cancer cells through their natural cytotoxicity pathways. Some of these approaches involve cancer vaccines, and others involve the genetic engineering of the immune cells to recognize leukemia biomarkers and the use of bispecific antibody T cell conjugates. However, these approaches also have significant limitations, such as substantial production costs and limited number of bispecific antibodies on the surface of cells.

SUMMARY OF THE INVENTION

In view of the foregoing, there is a need for improved modalities for targeting of therapeutics, in the area of immunotherapy and others. The present disclosure addresses these needs, and provides additional advantages as well.

In one aspect, the disclosure provides a complex comprising a targeting unit and a therapeutic unit. In some embodiments, the targeting unit comprises a targeting moiety conjugated to a first linker, and the therapeutic unit comprises a therapeutic agent conjugated to a second linker, and wherein said targeting unit and said therapeutic unit form a reversible complex via interaction between the first linker and the second linker. The interaction may be direct or indirect. In some embodiments, the complex is reversible by disrupting the interaction between the first linker and the second linker by changing temperature, changing pH, enzymatic reaction, or changing ionic strength. In some embodiments, the first linker is a first polynucleotide and the second linker is a second polynucleotide, wherein the reversible complex forms via the first polynucleotide hybridizing to the second polynucleotide based on sequence complementarity. In some embodiments, the targeting unit comprises a targeting moiety conjugated to a first linker, and the therapeutic unit comprises a therapeutic agent conjugated to a second linker, and wherein said targeting unit and said therapeutic unit are separated by a length of 1 nm to 400 nm (e.g. more than 1 nm, 2 nm, 3 nm, 4 nm, 5 nm, 6 nm, 7 nm, 8 nm, 9 nm, 10 nm, or more; less than 400 nm, 300 nm, 200 nm, 100 nm, 50 nm, or less; or between 1 nm to 200 nm, 1 nm to 100 nm, 1 nm to 50 nm, 5 nm to 100 nm, or 5 nm to 50 nm) via interaction between the first linker and the second linker. In some embodiments, the first linker comprises a first reactive group and the second linker comprises a second reactive group, and further wherein the complex is formed via a reaction between the first reactive group and the second reactive group to form a covalent bond therebetween. In some embodiments, the therapeutic agent is a cell. In some embodiments, the targeting moiety exhibits specific binding to a biological marker on a target cell, wherein administering the complex enhances activity of the therapeutic agent at the target cell to a greater degree as compared to administering either the therapeutic agent or the targeting moiety alone.

In some embodiments, the targeting unit comprises a targeting moiety conjugated to a first polynucleotide, and the therapeutic unit comprises a therapeutic agent conjugated to a second polynucleotide, wherein said targeting unit and said therapeutic unit form a complex via complementarity between the first polynucleotide and the second polynucleotide, or with one or more adapter polynucleotides. In some embodiments, the targeting moiety comprises an antigen binding unit, such as an antibody. In some embodiments, the therapeutic agent is a live cell, such as an effector cell or a stem cell.

In some embodiments, the targeting unit comprises a targeting moiety conjugated to a first reactive group, and the therapeutic unit comprises a therapeutic agent conjugated to a second reactive group, and wherein said targeting unit and said therapeutic unit form a complex via a covalent bond formed by a reaction between the first reactive group and the second reactive group. In some embodiments, the targeting moiety comprises an antigen binding unit, such as an antibody. In some embodiments, the therapeutic agent is a live cell, such as an effector cell or a stem cell.

In one aspect, the disclosure provides a live cell comprising an outer surface and a population of at least about 1,000 exogenous targeting units complexed to the outer surface. In some embodiments, an exogenous targeting unit in said population comprises a targeting moiety that is characterized in that: (a) it exhibits specific binding to a biological marker; (b) it is not a nucleic acid; and (c) it is not produced by said live cell. In some embodiments, the targeting moiety is conjugated to a first polynucleotide. In some embodiments, the targeting moiety comprises an antigen-binding unit. In some embodiments, the first polynucleotide comprises a single-stranded region. In some embodiments, the targeting unit is complexed to the outer surface via the first polynucleotide and a second polynucleotide conjugated to the outer surface of the cell. In some embodiments, the targeting unit comprises a targeting moiety conjugated to a first member of a binding pair. In some embodiments, the targeting unit is complexed to the outer surface via the first member of the binding pair and a second member of the binding pair conjugated to the outer surface of the cell. In some embodiments, the binding pair is selected from the group consisting of: a DNA binding domain and a target DNA; a leucine zipper and a target DNA; biotin and avidin; biotin and streptavidin; calmodulin binding protein and calmodulin; a hormone and a hormone receptor; lectin and a carbohydrate; a cell membrane receptor and a receptor ligand; and an enzyme and a substrate. In some embodiments, the at least 1,000 exogenous targeting units comprise at least two different targeting units, each different targeting unit exhibiting specific binding to the same or different biological marker. In some embodiments, the cell is complexed to the targeting moiety via a covalent bond formed by a reaction between a first reactive group conjugated to the cell and a second reactive group conjugated to the targeting moiety. The second reactive group may be part of a linker comprising a PEG region.

In one aspect, the disclosure provides a live cell comprising an outer surface and at least a first type and a second type of exogenous targeting unit complexed to said outer surface. In some embodiments, the first type and the second type each comprise a distinct targeting moiety that (a) is not a nucleic acid, and (b) is not produced by said live cell, and wherein the first type and the second type of exogenous targeting units each bind specifically to a different antigen. In some embodiments, the live cell is an effector cell or a stem cell. In some embodiments, the targeting unit comprises an antigen-binding unit. In some embodiments, the antigen is a cancer antigen.

In one aspect, the disclosure provides a population of effector cells that are complexed with targeting units, such as exogenous targeting units, exhibiting binding specificity to one or more biological markers present on a population of target cells. In some embodiments, said effector cell population is characterized in that: upon exposing said effector cell population to said target cell population in an in vitro cell death assay, said population of effector cells induces death of at least 20% of said target cells within about 5 hours, when the ratio of the number of effector cells in said effector cell population to the number of target cells in said target cell population is about 10 to 1 or less. In some embodiments, said effector cell population is characterized in that: upon exposing said effector cell population to said target cell population in an in vitro cell death assay, said population of effector cells induces death of at least 5 fold more target cells as compared to a corresponding population of effector cells that are not complexed with the exogenous targeting unit, wherein the exogenous targeting unit is not produced by said population of effector cells.

In one aspect, the disclosure provides a method of producing a conjugated live cell complexed with a targeting unit comprising a targeting moiety. In some embodiments, the method comprises: (a) reacting a targeting moiety with a first polynucleotide to produce a targeting unit comprising the targeting moiety conjugated to the first polynucleotide; (b) reacting a live cell with a second polynucleotide to produce a conjugated cell comprising the second polynucleotide conjugated to the surface of the live cell; and (c) combining the targeting unit and the conjugated cell under conditions effective to form a complex between the conjugated live cell and the targeting unit via the first polynucleotide hybridizing to the second polynucleotide based on sequence complementarity. In some embodiments, the targeting moiety is conjugated to the first polynucleotide using a coupling group. In some embodiments, the coupling group is an activated ester, such as an NHS ester. In some embodiments, the second polynucleotide is conjugated to the live cell using a coupling group, such as an activated ester (e.g. an NHS ester).

In one aspect, the disclosure provides a method of delivering a therapeutic agent to a target cell comprising a biological marker. In some embodiments, the method comprises administering to the target cell a complex comprising a targeting unit and a therapeutic unit in accordance with any embodiment of the present disclosure, wherein the therapeutic agent is delivered to the cell via the targeting moiety specifically binding to the biological marker. In some embodiments, the first linker is a first polynucleotide and the second linker is a second polynucleotide, and further wherein the reversible complex forms via the first polynucleotide hybridizing to the second polynucleotide based on sequence complementarity. In some embodiments, the complex is administered to the target cell in vivo or in vitro. In some embodiments, the therapeutic agent is an epitope or bacterial cell, and the cell comprising the biological marker is an antigen presenting cell. In some embodiments, the biological marker is an extracellular marker secreted by the target cell in a target tissue. In some embodiments, the therapeutic agent is a stem cell or a cardiomyocyte, the target tissue is cardiac tissue, and further wherein the stem cell or cardiomyocyte repairs ischemic damage in the cardiac tissue by producing new cardiac tissue.

In one aspect, the disclosure provides a method of reducing one or more side-effects of a therapeutic agent in a subject in need thereof. In some embodiments, the method comprises administering to the subject a complex comprising a targeting unit and a therapeutic unit in accordance with any embodiment of the present disclosure, wherein the therapeutic agent in the complex is delivered in an amount that is less than an amount of the same therapeutic agent necessary to achieve a comparable therapeutic effect when administered alone. In some embodiments, the first linker is a first polynucleotide and the second linker is a second polynucleotide, and further wherein the reversible complex forms via the first polynucleotide hybridizing to the second polynucleotide based on sequence complementarity.

In one aspect, the disclosure provides a method of inducing death of target cells. In some embodiments, the method comprises administering to the target cells a complex comprising a targeting unit and a therapeutic unit in accordance with any embodiment of the present disclosure, wherein administering the complex to the target cells induces a greater degree of target cell death relative to administering a comparable amount of the therapeutic agent alone. In some embodiments, the first linker is a first polynucleotide and the second linker is a second polynucleotide, and further wherein the reversible complex forms via the first polynucleotide hybridizing to the second polynucleotide based on sequence complementarity. In some embodiments, the complex is administered to the target cell in vivo or in vitro.

In some embodiments, the method of inducing cell death comprises administering to the target cells a plurality of conjugated cells complexed to exogenous targeting units, in accordance with any embodiment of the present disclosure. In some embodiments, administering the complexed cells to the target cells induces a greater degree of target cell death relative to administering a comparable amount of complexed cells lacking the targeting units. In some embodiments, a complexed cell comprises a first type and a second type of exogenous targeting unit complexed to said outer surface, wherein the first type and the second type each comprise a distinct targeting moiety that (a) is not a nucleic acid, and (b) is not produced by said live cell, and wherein the first type and the second type of exogenous targeting units each bind specifically to a different antigen. In some embodiments, the plurality of complexed cells is administered to the target cells in vivo or in vitro.

In one aspect, the disclosure provides a method of treating cancer. In some embodiments, the method comprises administering to a subject in need thereof a complex comprising a targeting unit and a therapeutic unit in accordance with any embodiment of the present disclosure, wherein (a) the targeting moiety exhibits specific binding to a biological marker on the cancer cell; and (b) the complex induces death of cancer cells. In some embodiments, the first linker is a first polynucleotide and the second linker is a second polynucleotide, and further wherein the reversible complex forms via the first polynucleotide hybridizing to the second polynucleotide based on sequence complementarity. In some embodiments, the method comprises administering to a subject in need thereof conjugated cells complexed to exogenous targeting units, in accordance with any embodiment of the present disclosure, wherein (a) the biological marker is on the cancer cell; and (b) the complexed cell induces death of cancer cells. In some embodiments, the complexed cell comprises a first type and a second type of exogenous targeting unit complexed to said outer surface, wherein the first type and the second type each comprise a distinct targeting moiety that (a) is not a nucleic acid, and (b) is not produced by said live cell, and wherein the first type and the second type of exogenous targeting units each bind specifically to a different antigen.

In one aspect, the disclosure provides a method for inducing cell proliferation in a target tissue. In some embodiments, the method comprises administering to a subject in need thereof a complex comprising a targeting unit and a therapeutic unit in accordance with any embodiment of the present disclosure, wherein (a) the complex is delivered to the target tissue via the targeting moiety specifically binding to a biological marker; and (b) the therapeutic agent induces cell proliferation in the target tissue. In some embodiments, the first linker is a first polynucleotide and the second linker is a second polynucleotide, and further wherein the reversible complex forms via the first polynucleotide hybridizing to the second polynucleotide based on sequence complementarity. In some embodiments, the method comprises administering to a subject in need thereof conjugated cells complexed to exogenous targeting units, in accordance with any embodiment of the present disclosure, wherein (a) the cell is delivered to the target tissue via the targeting moiety specifically binding to the biological marker; and (b) the complexed cell proliferates in the target tissue. In some embodiments, the complexed cell comprises a first type and a second type of exogenous targeting unit complexed to said outer surface, wherein the first type and the second type each comprise a distinct targeting moiety that (a) is not a nucleic acid, and (b) is not produced by said live cell, and wherein the first type and the second type of exogenous targeting units each bind specifically to a different antigen.

In one aspect, the disclosure provides a method of growing stem cells in solution. In some embodiments, the method comprises (a) combining a first population of cells that are live conjugated cells complexed to exogenous targeting units, in accordance with any embodiment of the present disclosure, and a second population of cells, wherein (i) one of the first and second populations is a population of stem cells; (ii) the other of the first and second populations is a population of feeder cells; and (iii) the biological marker is a marker on the surface of cells in the second population; and (b) growing the stem cells as non-adherent cells free in solution, associated with the feeder cells via the targeting units.

In one aspect, the disclosure provides a population of cells complexed thereto one or more proteins. In some embodiments, the population of cells exhibits an increased ability to induce death of a target cell to which one of the one or more proteins binds, wherein the one or more proteins are not a bispecific antibody. An increased ability to induce death of a target cell may be a gained ability, where a comparable cell not complexed with the one or more proteins lacked such ability. Alternatively, an increased ability may represent an increase of 10%, 25%, 50%, 75%, 100%, 200%, 300%, 500%, 1000%, or more relative to comparable cells not complexed with the one or more proteins. In some embodiments, (a) said population of cells exhibits an increased ability to bind to a target cell; (b) one of the one or more proteins has a half-life on the cell surface of more than 8 hours; and (c) the one or more proteins are not bispecific antibodies. In general, bispecific antibody is an antibody having specificity for two different targets, such as a hybrid antibody having two different Fab arms, or two Fab arms directed to one antigen fused to two Fab arms directed to another antigen with both pairs of Fab arms joined by way of a heavy chain fusion. In some embodiments, at least one of the one or more proteins is a targeting moiety, such as any targeting moiety described herein.

In one aspect, the disclosure provides a method of inducing death of a target cell in a subject. In some embodiments, the method comprises (a) obtaining a population of effector cells from said subject; (b) complexing one or more proteins to the effector cells; and (c) administering the effector cells from step (b) to the subject thereby inducing death of the target cell; wherein the one or more proteins are not bispecific antibodies. In some embodiments, steps (a) to (c) are completed within 24 hours. In some embodiments, the effector cells from step (b) are administered without inducing cell expansion prior to administration, or without introducing exogenous nucleic acids into the effector cells prior to administration.

In one aspect, the disclosure provides a method of treating cancer in a subject. In some embodiments, the method comprises (a) obtaining a population of effector cells from said subject; (b) complexing one or more proteins to the effector cells; and (c) administering the effector cells from step (b) to the subject thereby treating cancer in the subject; wherein the one or more proteins are not bispecific antibodies. In some embodiments, steps (a) to (c) are completed within 24 hours. In some embodiments, the effector cells from step (b) are administered without inducing cell expansion prior to administration, or without introducing exogenous nucleic acids into the effector cells prior to administration.

In one aspect, the disclosure provides a method of producing a live cell complexed with a targeting moiety. In some embodiments, the method comprises: (a) conjugating a targeting moiety with a first linker comprising a first reactive group; (b) conjugating a live cell with a second linker comprising a second reactive group; and (c) combining the conjugated targeting unit and the conjugated live cell under conditions effective to form a complex between the live cell and the targeting moiety via a covalent bond formed by a reaction between a first reactive group and the second reactive group. The cell, targeting moiety, and reactive groups can be in accordance with any embodiment of the present disclosure.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
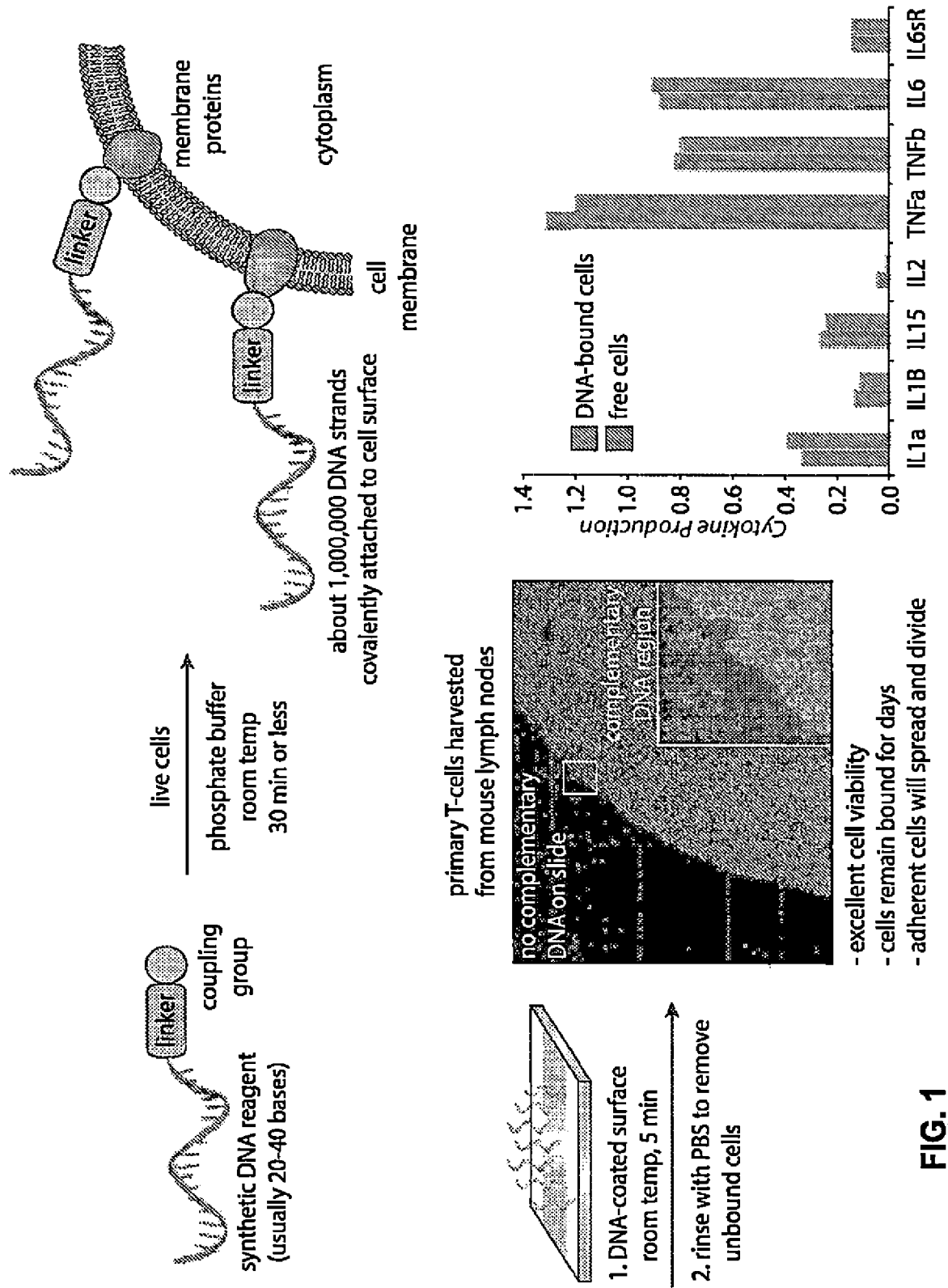
FIG. 1 illustrates an example process of conjugating DNA to a cell surface, binding of conjugated cells to a surface coated with complementary DNA, and shows viability and functionality of conjugated cells. The label "linker" refers to the entire pictured molecule, including the polynucleotide and coupling group.

The practice of some embodiments disclosed herein employ, unless otherwise indicated, conventional techniques of immunology, biochemistry, chemistry, molecular biology, microbiology, cell biology, genomics and recombinant DNA, which are within the skill of the art. See for example Sambrook and Green, Molecular Cloning: A Laboratory Manual, 4th Edition (2012); the series Current Protocols in Molecular Biology (F. M. Ausubel, et al. eds.); the series Methods In Enzymology (Academic Press, Inc.), PCR 2: A Practical Approach (M. J. MacPherson, B. D. Hames and G. R. Taylor eds. (1995)), Harlow and Lane, eds. (1988) Antibodies, A Laboratory Manual, and Culture of Animal Cells: A Manual of Basic Technique and Specialized Applications, 6th Edition (R. I. Freshney, ed. (2010)).

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs, such as peptide nucleic acid (PNA), Morpholino and locked nucleic acid (LNA), glycol nucleic acid (GNA), threose nucleic acid (TNA), 2'-fluoro, 2'-OMe, and phosphorothiolated DNA. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component or other conjugation target.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner according to base complementarity. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the enzymatic cleavage of a polynucleotide by an endonuclease. A second sequence that is complementary to a first sequence is referred to as the "complement" of the second sequence. The term "hybridizable" as applied to a polynucleotide refers to the ability of the polynucleotide to form a complex that is stabilized via hydrogen bonding between the bases of the nucleotide residues in a hybridization reaction.

"Complementarity" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions. Sequence identity, such as for the purpose of assessing percent complementarity, may be measured by any suitable alignment algorithm, including but not limited to the Needleman-Wunsch algorithm (see e.g. the EMBOSS Needle aligner available at www.ebi.ac.uk/Tools/psa/emboss needle/nucleotide.html, optionally with default settings), the BLAST algorithm (see e.g. the BLAST alignment tool available at blast.ncbi.nlm-.nih.gov/Blast.cgi, optionally with default settings), or the Smith-Waterman algorithm (see e.g. the EMBOSS Water aligner available at www.ebi.ac.uk/Tools/psa/emboss water/ nucleotide.html, optionally with default settings).

In general, "stringent conditions" for hybridization refer to conditions under which a nucleic acid having complementarity to a target sequence predominantly hybridizes with a target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part I, Second Chapter "Overview of principles of hybridization and the strategy of nucleic acid probe assay", Elsevier, N.Y.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells, and their progeny of a biological entity obtained in vivo or cultured in vitro are also encompassed.

The terms "therapeutic agent", "therapeutic capable agent" or "treatment agent" are used interchangeably and refer to a molecule or compound that confers some beneficial effect upon administration to a subject. The beneficial effect includes enablement of diagnostic determinations; amelioration of a disease, symptom, disorder, or pathological condition; reducing or preventing the onset of a disease, symptom, disorder or condition; and generally counteracting a disease, symptom, disorder or pathological condition.

As used herein, "treatment" or "treating," or "palliating" or "ameliorating" are used interchangeably. These terms refer to an approach for obtaining beneficial or desired results including but not limited to a therapeutic benefit and/or a prophylactic benefit. By therapeutic benefit is meant any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested. Typically, prophylactic benefit includes reducing the incidence and/or worsening of one or more diseases, conditions, or symptoms under treatment (e.g. as between treated and untreated populations, or between treated and untreated states of a subject).

The term "effective amount" or "therapeutically effective amount" refers to the amount of an agent that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. An effective amount of an active agent may be administered in a single dose or in multiple doses. A component may be described herein as having at least an effective amount, or at least an amount effective, such as that associated with a particular goal or purpose, such as any described herein.

The term "effective amount" also applies to a dose that will provide an image for detection by an appropriate imaging method. The specific dose may vary depending on one or more of: the particular agent chosen, the dosing regimen to be followed, whether it is administered in combination with other compounds, timing of administration, the tissue to be imaged, and the physical delivery system in which it is carried.

Compositions:

Compositions described herein have a wide variety of uses, including but not limited to use as therapeutics, use in diagnostic methods, use in drug screening, and use in promoting cell growth in vivo and in vitro, among others. In one aspect, the disclosure provides a complex comprising a targeting unit and a therapeutic unit. In some embodiments, the targeting unit comprises a targeting moiety conjugated to a first linker, and the therapeutic unit comprises a therapeutic agent conjugated to a second linker, and wherein said targeting unit and said therapeutic unit form a reversible complex via interaction between the first linker and the second linker. The interaction between the first linker and the second linker may be direct or indirect. In general, an indirect interaction is one that is mediated by one or more intermediate compounds (e.g. 1, 2, 3, 4, 5, 6, 7, 8, 9, 10, or more intermediate compounds). An intermediate compound may be of the same or different type as one or both linkers. In some embodiments, the first and second linkers are the same and interact via simultaneous interaction with an intermediate compound. For example, the first and second linkers may be the same antibody, which interact indirectly with one another by way of simultaneously binding an intermediate compound comprising two or more copies of the antigen to which the antibody is directed. In some embodiments, the first linker and the second linker are different. In some embodiments, the first and second linker interact directly. In general, a direct interaction is an interaction that does not require interaction with an intermediate compound. In some embodiments, the targeting unit comprises a targeting moiety conjugated to a first polynucleotide, and the therapeutic unit comprises a therapeutic agent conjugated to a second polynucleotide, and wherein said targeting unit and said therapeutic unit form a complex via complementarity between the first polynucleotide and the second polynucleotide, or with an adapter polynucleotide. The first and second polynucleotides may interact directly, such as by hybridizing to one another. The first and second polynucleotides may interact indirectly, such as via interaction with an intermediate compound. In some embodiments, the intermediate compound is an adapter polynucleotide, such as described herein. For example, the first and second polynucleotides may interact indirectly via complementarity with portions of the adapter polynucleotide. In some embodiments, the therapeutic agent is a cell, including a living cell. In some embodiments, the first and second linker are reactive groups that react with one another to form a covalent bond. Each reactive group may first be reacted directly with the entity to which it is attached (e.g. a targeting moiety or a therapeutic agent) to form a covalent bond.

In another aspect, the disclosure provides a live cell comprising an outer surface and a population of at least about 1,000 exogenous targeting units complexed to the outer surface, wherein an exogenous targeting unit in said population comprises a targeting moiety that is characterized in that: (a) it exhibits specific binding to a biological marker; (b) it is not a nucleic acid; and (c) it is not produced by said live cell In yet another aspect, the disclosure provides a live cell comprising an outer surface and at least a first type and a second type of exogenous targeting unit complexed to said outer surface, wherein the first type and the second type each comprise a distinct targeting moiety that (a) is not a nucleic acid, and (b) is not produced by said live cell, and wherein the first type and the second type of exogenous targeting units each bind specifically to a different antigen.

A targeting unit embodied in a subject complex disclosed herein typically comprises a targeting moiety which renders the targeting unit the ability to distinguish target from non-target by exhibiting preferential binding. Accordingly, a targeting moiety of a targeting unit includes compounds and complexes having a higher binding affinity for a target compound or complex than for non-target compounds or complexes in a complex mixture. A targeting moiety may be selected based on having, or produced to have, a binding affinity for a desired target, such as a biomarker associated with a target cell. Examples of targeting moieties include, but are not limited to, antibody (with affinity for a target antigen), hormone or other ligand (with affinity for a target receptor), lectin (with affinity for a target carbohydrate), carbohydrate (with affinity for a target lectin), nucleic acid (RNA or DNA) hybridizing sequences, aptamer (with affinity for a particular target), and the like. In some embodiments, the targeting moiety is not a nucleic acid. In some embodiments, the affinity with which a targeting moiety binds a particular target is about or more than about 2, 3, 4, 5, 6, 7, 8, 9, 10, 15, 20, 25, 50, 75, 100, 150, 200, 300, 400, 500, 1000, $1 \times 10^4$, $1 \times 10^5$, $1 \times 10^6$, $1 \times 10^7$, $1 \times 10^8$, or more fold greater than the affinity with which the targeting moiety binds a non-target compound. In some embodiments, the binding affinity ($K_D$) of a targeting moiety for its target is about 0.02 to about 200 nM. In some embodiments, the binding affinity is about or less than about 250 nM, 200 nM, 100 nM, 50 nM, 10 nM, 1 nM, 500 pM, 100 pM, 60 pM, 50 pM, 20 pM, 15 pM, 10 pM, 5 pM, 2 pM, or less. Affinity may be measured by any suitable method, such as surface plasmon resonance at a selected temperature (e.g. 25 or 37° C.).

Biological markers associated with a cell to which a targeting moiety may be directed include cell surface markers. Non-limiting examples of cell surface markers include carbohydrates; glycolipids; glycoproteins; CD (cluster of differentiation) antigens present on cells of a hematopoietic lineage (e.g., CD2, CD4, CD8, CD21, etc.); γ-glutamyl-transpeptidase; an adhesion protein (e.g., ICAM-1, ICAM-2, ELAM-1, VCAM-1); hormone, growth factor, cytokine, and other ligand receptors; ion channels; and the membrane-bound form of an immunoglobulin μ, chain. In some embodiments, the biological marker associated with a target cell is present on the surface of a target cells at about or less than about 100000, 50000, 10000, 5000, 1000, 750, 500, 100, 50, or fewer copies per cell. In some embodiments, the average density of a biological marker associated with the surface of a target cell in a population of target cells is about or less than about 100000, 50000, 10000, 5000, 1000, 750, 500, 100, 50, or fewer copies per cell. In some embodiments, the biological marker is associated with a target cell by way of increased concentration of the marker in a fluid surrounding the target cell or a tissue in which it resides than is found in fluid more distant from the target cell, such as where a cell secretes the biological marker. Of particular interest are biological markers associated with a disease or disease state. A vast variety of disease-related biological markers have been identified, and the corresponding targeting moieties have been generated, such as targeting moieties direct to alfa-fetoprotein (AFP), C-reactive protein (CRP), cancer antigen-50 (CA-50), cancer antigen-125 (CA-125) associated with ovarian cancer, cancer antigen 15-3 (CA15-3) associated with breast cancer, cancer antigen-19 (CA-19) and cancer antigen-242 associated with gastrointestinal cancers, carcinoembryonic antigen (CEA), carcinoma associated antigen (CAA), chromogranin A, epithelial mucin antigen (MC5), human epithelium specific antigen (HEA), Lewis(a)antigen, melanoma antigen, melanoma associated antigens 100, 25, and 150, mucin-like carcinoma-associated antigen, multidrug resistance related protein (MRPm6), multidrug resistance related protein (MRP41), Neu oncogene protein (C-erbB-2), neuron specific enolase (NSE), P-glycoprotein (mdr1 gene product), multidrug-resistance-related antigen, p170, multidrug-resistance-related antigen, prostate specific antigen (PSA), CD56, and NCAM.

In some embodiments, the targeting moiety is an antigen-binding unit. The term "antigen-binding unit" refers generally to a moiety having a high affinity for an antigen. For example, an antigen binding unit may have an affinity for a particular antigen of about or less than about 100 nM, 50 nM, 10 nM, 1 nM, 500 pM, 100 pM, 60 pM, 50 pM, 20 pM, 15 pM, 10 pM, 5 pM, 2 pM, or less. Non-limiting examples of antigen binding units include aptamers and antibodies. The term "antibody" as used herein includes whole antibodies and any antigen binding fragment (i.e., "antigen-binding portion") or single chains thereof. An "antibody" refers to a glycoprotein comprising at least two heavy (H) chains and two light (L) chains inter-connected by disulfide bonds, or an antigen binding portion thereof. A typical heavy chain is comprised of a heavy chain variable region (abbreviated herein as $V_H$) and a heavy chain constant region. A typical heavy chain constant region is comprised of three domains, $C_H1$, $C_H2$ and $C_H3$. A typical light chain is comprised of a light chain variable region (abbreviated herein as $V_L$) and a light chain constant region. A typical light chain constant region is comprised of one domain, $C_1$, $V_H$ and $V_L$ regions can be further subdivided into regions of hypervariability, termed complementarity determining regions (CDR), interspersed with regions that are more conserved, termed framework regions (FR). A $V_H$ and $V_L$ may be composed of three CDRs and four FRs, arranged from amino-terminus to carboxy-terminus in the following order: FR1, CDR1, FR2, CDR2, FR3, CDR3, and FR4. In general, variable regions of the heavy and light chains contain a binding domain that interacts with an antigen.

The term "antigen-binding portion" of an antibody (or simply "antibody portion" or "antibody fragment"), as used herein, refers to one or more fragments of an antibody that retain the ability to specifically bind to an antigen (e.g., a target biomarker). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_1$, and $C_H1$ domains; (ii) a F(ab')$_2$ fragment, a bivalent fragment comprising two Fab fragments linked by a disulfide bridge at the hinge region; (iii) a Fab' fragment, which is essentially a Fab with part of the hinge region (see, FUNDAMENTAL IMMUNOLOGY (Paul ed., $3^{rd}$ ed. 1993); (iv) an Fd fragment consisting of the $V_H$ and $C_H1$ domains; (v) an Fv fragment consisting of the $V_L$ and $V_H$ domains of a single arm of an antibody, (vi) a dAb fragment (Ward et al., (1989) Nature 341:544-546), which consists of a $V_H$ domain; (vii) an isolated complementarity determining region (CDR); and (viii) a nanobody, a heavy chain variable region containing a single variable domain and two constant domains. Furthermore, although the two domains of the Fv fragment, $V_L$ and are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments can be obtained using any suitable techniques known to those with skill in the art, and the fragments can be screened for target binding affinity using methods similar to those used for screening intact antibodies.

An antibody utilized in accordance with the present disclosure may be a polyclonal, monoclonal, chimeric, humanized, or fully human. The terms "monoclonal antibody" or "monoclonal antibody composition" as used herein refer to a preparation of antibody molecules of single molecular composition. A monoclonal antibody composition displays a single binding specificity and affinity for a particular epitope. The term "human antibody," as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies may include amino acid residues not encoded by human germline immunoglobulin sequences (e.g., mutations introduced by random or site-specific mutagenesis in vitro or by somatic mutation in vivo). However, the term "human antibody," as used herein, is not intended to include antibodies in which CDR sequences derived from the germline of another mammalian species, such as a mouse, have been grafted onto human framework sequences. The term "humanized antibody" is intended to refer to antibodies in which CDR sequences derived from the germline of another mammalian species, such as a mouse, have been grafted onto human framework sequences. Additional framework region modifications may be made within the human framework sequences. The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

In some embodiment, the targeting moiety is not produced by a cell conjugated thereto a linker.

A therapeutic agent embodied in a subject complex disclosed herein may be selected based on a condition being treated, or on a desired therapeutic effect. Non-limiting examples of therapeutic agents include small molecule drugs, polypeptides, antigens, antibodies, receptors, ligands, cells (e.g. eukaryotic, prokaryotic, bacterial, stem, pluripotent, recombinant, induced pluripotent, live, dead, or portions of any of these), viruses or components thereof, and labels (e.g. dyes for visualizing a target). Non-limiting examples of anti-cancer agents include mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, immunotherapeutic agents, proapoptotic agents, and anti-androgens.

In some embodiments, the therapeutic agent is a cell, including but not limited to live cells, dead cells, or to a mixture of live and dead cells. Non-limiting examples of cells can include an immune cell, natural killer cell, a macrophage, a neutrophil, a T-cell, a natural killer T-cell (NKT cells), a stem cell, a cancer cell, and antigen presenting cell (APC), or a bacterial cell. Cells used as a therapeutic agent may be primary cells from a sample from a subject, cells from a cell line, and/or transgenic cells. Cells may be eukaryotic or prokaryotic. In some embodiments, the cell is an effector cell. In general, the term "effector cell" relates to a cell that performs a specific function in response to a stimulus such as cells in the immune system. In some embodiments, effector cells are cells that induce cell death. Non-limiting examples of effector cells include lymphocytes (such as T cells, including cytolytic T cells (CTLs)), killer cells, natural killer cells, macrophages, monocytes, eosinophils, neutrophils, polymorphonuclear cells, granulocytes, mast cells, and basophiles. In some embodiments, the cell is a cell involved in the cognitive and/or activation phases of an immune response, such as antigen presenting cells (APCs), including dendritic cells.

Subjects from which cells may be derived include, but are not limited to, mammals, such as a human. Samples may be provided directly by the subject, or indirectly through one or more intermediaries, such as a sample collection service provider or a medical provider (e.g. a physician or nurse). Examples of samples from a subject from which cells may be derived include, without limitation, skin, heart, lung, kidney, bone marrow, breast, pancreas, liver, muscle, smooth muscle, bladder, gall bladder, colon, intestine, brain, prostate, esophagus, thyroid, serum, saliva, urine, gastric and digestive fluid, tears, stool, semen, vaginal fluid, interstitial fluids derived from tumorous tissue, ocular fluids, sweat, mucus, earwax, oil, glandular secretions, spinal fluid, hair, fingernails, plasma, nasal swab or nasopharyngeal wash, spinal fluid, cerebral spinal fluid, tissue, throat swab, biopsy, placental fluid, amniotic fluid, cord blood, emphatic fluids, cavity fluids, sputum, pus, microbiota, meconium, breast milk, and/or other excretions or body tissues. Examples of cell types to which a linker may be conjugated include, but are not limited to, lymphoid cells, such as B cell, T cell (Cytotoxic T cell, Natural Killer T cell, Regulatory T cell, T helper cell), Natural killer cell, cytokine induced killer (CIK) cells (see e.g. US20080241194); myeloid cells, such as granulocytes (Basophil granulocyte, Eosinophil granulocyte, Neutrophil granulocyte/Hypersegmented neutrophil), Monocyte/Macrophage, Red blood cell (Reticulocyte), Mast cell, Thrombocyte/Megakaryocyte, Dendritic cell; cells from the endocrine system, including thyroid (Thyroid epithelial cell, Parafollicular cell), parathyroid (Parathyroid chief cell, Oxyphil cell), adrenal (Chromaffin cell), pineal (Pinealocyte) cells; cells of the nervous system, including glial cells (Astrocyte, Microglia), Magnocellular neurosecretory cell, Stellate cell, Boettcher cell, and pituitary (Gonadotrope, Corticotrope, Thyrotrope, Somatotrope, Lactotroph); cells of the Respiratory system, including Pneumocyte (Type I pneumocyte, Type II pneumocyte), Clara cell, Goblet cell, Dust cell; cells of the circulatory system, including Myocardiocyte, Pericyte; cells of the digestive system, including stomach (Gastric chief cell, Parietal cell), Goblet cell, Paneth cell, G cells, D cells, ECL cells, I cells, K cells, S cells; enteroendocrine cells, including enterochromaffin cell, APUD cell, liver (Hepatocyte, Kupffer cell), Cartilage/bone/muscle; bone cells, including Osteoblast, Osteocyte, Osteoclast, teeth (Cementoblast, Ameloblast); cartilage cells, including Chondroblast, Chondrocyte; skin cells, including Trichocyte, Keratinocyte, Melanocyte (Nevus cell); muscle cells, including Myocyte; urinary system cells, including Podocyte, Juxtaglomerular cell, Intraglomerular mesangial cell/Extraglomerular mesangial cell, Kidney proximal tubule brush border cell, Macula densa cell; reproductive system cells, including Spermatozoon, Sertoli cell, Leydig cell, Ovum; and other cells, including Adipocyte, Fibroblast, Tendon cell, Epidermal keratinocyte (differentiating epidermal cell), Epidermal basal cell (stem cell), Keratinocyte of fingernails and toenails, Nail bed basal cell (stem cell), Medullary hair shaft cell, Cortical hair shaft cell, Cuticular hair shaft cell, Cuticular hair root sheath cell, Hair root sheath cell of Huxley's layer, Hair root sheath cell of Henle's layer, External hair root sheath cell, Hair matrix cell (stem cell), Wet stratified barrier epithelial cells, Surface epithelial cell of stratified squamous epithelium of cornea, tongue, oral cavity, esophagus, anal canal, distal urethra and vagina, basal cell (stem cell) of epithelia of cornea, tongue, oral cavity, esophagus, anal canal, distal urethra and vagina, Urinary epithelium cell (lining urinary bladder and urinary ducts), Exocrine secretory epithelial cells, Salivary gland mucous cell (polysaccharide-rich secretion), Salivary gland serous cell (glycoprotein enzyme-rich secretion), Von Ebner's gland cell in tongue (washes taste buds), Mammary gland cell (milk secretion), Lacrimal gland cell (tear secretion), Ceruminous gland cell in ear (wax secretion), Eccrine sweat gland dark cell (glycoprotein secretion), Eccrine sweat gland clear cell (small molecule secretion). Apocrine sweat gland cell (odoriferous secretion, sex-hormone sensitive), Gland of Moll cell in eyelid (specialized sweat gland), Sebaceous gland cell (lipid-rich sebum secretion), Bowman's gland cell in nose (washes olfactory epithelium), Brunner's gland cell in duodenum (enzymes and alkaline mucus), Seminal vesicle cell (secretes seminal fluid components, including fructose for swimming sperm), Prostate gland cell (secretes seminal fluid components), Bulbourethral gland cell (mucus secretion), Bartholin's gland cell (vaginal lubricant secretion), Gland of Littre cell (mucus secretion), Uterus endometrium cell (carbohydrate secretion), Isolated goblet cell of respiratory and digestive tracts (mucus secretion), Stomach lining mucous cell (mucus secretion), Gastric gland zymogenic cell (pepsinogen secretion), Gastric gland oxyntic cell (hydrochloric acid secretion), Pancreatic acinar cell (bicarbonate and digestive enzyme secretion), Paneth cell of small intestine (lysozyme secretion), Type II pneumocyte of lung (surfactant secretion), Clara cell of lung, Hormone secreting cells, Anterior pituitary cells, Somatotropes, Lactotropes, Thyrotropes, Gonadotropes, Corticotropes, Intermediate pituitary cell, Magnocellular neurosecretory cells, Gut and respiratory tract cells, Thyroid gland cells, thyroid epithelial cell, parafollicular cell, Parathyroid gland cells, Parathyroid chief cell, Oxyphil cell, Adrenal gland cells, chromaffin cells, Leydig cell of testes, Theca interna cell of ovarian follicle, Corpus luteum cell of ruptured ovarian follicle, Granulosa lutein cells, Theca lutein cells, Juxtaglomerular cell (renin secretion), Macula densa cell of kidney, Metabolism and storage cells, Barrier function cells (Lung, Gut, Exocrine Glands and Urogenital Tract), Kidney, Type I pneumocyte (lining air space of lung), Pancreatic duct cell (centroacinar cell), Nonstriated duct cell (of sweat gland, salivary gland, mammary gland, etc.), Duct cell (of seminal vesicle, prostate gland, etc.), Epithelial cells lining closed internal body cavities, Ciliated cells with propulsive function, Extracellular matrix secretion cells, Contractile cells; Skeletal muscle cells, stem cell, Heart muscle cells, Blood and immune system cells, Erythrocyte (red blood cell), Megakaryocyte (platelet precursor), Monocyte, Connective tissue macrophage (various types), Epidermal Langerhans cell, Osteoclast (in bone), Dendritic cell (in lymphoid tissues), Microglial cell (in central nervous system), Neutrophil granulocyte, Eosinophil granulocyte, Basophil granulocyte, Mast cell, Helper T cell, Suppressor T cell, Cytotoxic T cell, Natural Killer T cell, B cell, Natural killer cell, Reticulocyte, Stem cells and committed progenitors for the blood and immune system (various types), Pluripotent stem cells, Totipotent stem cells, Induced pluripotent stem cells, adult stem cells, Sensory transducer cells, Autonomic neuron cells, Sense organ and peripheral neuron supporting cells, Central nervous system neurons and glial cells, Lens cells, Pigment cells, Melanocyte, Retinal pigmented epithelial cell, Germ cells, Oogonium/Oocyte, Spermatid, Spermatocyte, Spermatogonium cell (stem cell for spermatocyte), Spermatozoon, Nurse cells, Ovarian follicle cell, Sertoli cell (in testis), Thymus epithelial cell, Interstitial cells, or Interstitial kidney cells.

The cells embodied in a subject complex or to which a linker is conjugated can be healthy cells, or diseased cells. For example the cells can be from a cancer condition such as epithelial cancer or carcinoma, including but not limited to, a carcinoma of the prostate, carcinoma of the breast, carcinoma of the colon, pancreatic carcinoma, lung carcinoma, skin carcinoma (melanoma), esophageal carcinoma, etc.; or the putative cell of origin (hepatocellular carcinoma, renal cell carcinoma, and small cell lung carcinoma, etc.). Other cancer cells include myoepithelial cancers, sarcomas, gliomas, lymphomas, leukemias, carcinoids, and any other type of cancer. Cells in other states or conditions of tissue may be used including but not limited to, autoimmune conditions, immune system related conditions (e.g. allergies, likely immune response to challenge), cells representative of conditions that contribute to or exhibit resistance to standard treatments, susceptibility or predisposition to a condition (e.g. susceptibility to diabetes, thyroid conditions, stroke, cardiovascular conditions, or liver quality, function, and degeneration, etc.). In some embodiments, the cell is a primary cell. In other embodiments, the cell is a mammalian cell. In some other embodiments, the cell is a stem cell.

In some embodiments the cells are from a cell line. Examples of cell lines include, but are not limited to, NK92, NK3.3, C8161, CCRF-CEM, MOLT, mIMCD-3, NHDF, HeLa-S3, Huh1, Huh4, Huh7, HUVEC, HASMC, HEKn, HEKa, MiaPaCell, Panel, PC-3, TF1, CTLL-2, C1R, Rat6, CV1, RPTE, A10, T24, J82, A375, ARH-77, Calu1, SW480, SW620, SKOV3, SK-UT, CaCo2, P388D1, SEM-K2, WEHI-231, HB56, TIB55, Jurkat, J45.01, LRMB, Bcl-1, BC-3, IC21, DLD2, Raw264.7, NRK, NRK-52E, MRC5, MEF, Hep G2, HeLa B, HeLa T4, COS, COS-1, COS-6, COS-M6A, BS-C-1 monkey kidney epithelial, BALB/3T3 mouse embryo fibroblast, 3T3 Swiss, 3T3-L1, 132-d5 human fetal fibroblasts; 10.1 mouse fibroblasts, 293-T, 3T3, 721, 9L, A2780, A2780ADR, A2780cis, A172, A20, A253, A431, A-549, ALC, B16, B35, BCP-1 cells, BEAS-2B, bEnd.3, BHK-21, BR 293, BxPC3, C3H-10T1/2, C6/36, Cal-27, CHO, CHO-7, CHO-IR, CHO-K1, CHO-K2, CHO-T, CHO Dhfr −/−, COR-L23, COR-L23/CPR, COR-L23/5010, COR-L23/R23, COS-7, COV-434, CML T1, CMT, CT26, D17, DH82, DU145, DuCaP, EL4, EM2, EM3, EMT6/AR1, EMT6/AR10.0, FM3, H1299, H69, HB54, HB55, HCA2, HEK-293, HeLa, Hepa1c1c7, HL-60, HMEC, HT-29, Jurkat, JY cells, K562 cells, Ku812, KCL22, KG1, KYO1, LNCap, Ma-Mel 1-48, MC-38, MCF-7, MCF-10A, MDA-MB-231, MDA-MB-468, MDA-MB-435, MDCK II, MDCK II, MOR/0.2R, MONO-MAC 6, MTD-1A, MyEnd, NCI-H69/CPR, NCI-H69/LX10, NCI-H69/LX20, NCI-H69/LX4, NIH-3T3, NALM-1, NW-145, OPCN/OPCT cell lines, Peer, PNT-1A/PNT 2, RenCa, RIN-5F, RMA/RMAS, Saos-2 cells, Sf-9, SkBr3, T2, T-47D, T84, THP1 cell line, U373, U87, U937, VCaP, Vero cells, WM39, WT-49, X63, YAC-1, YAR, and transgenic varieties thereof. Cell lines are available from a variety of sources known to those with skill in the art (see, e.g., the American Type Culture Collection (ATCC) (Manassas, Va.)).

In some embodiments, the cell is a T-cell. T-cells include all cells which express CD3, including T-cell subsets which also express CD4 and/or CD8. T-cells include both naive and memory cells (e.g. $T_{CM}$, $T_{EM}$ and $T_{EMRA}$), effector cells (e.g. CTLs or Tc cells), helper cells (e.g. Th1, Th2, Th3, Th9, Th7, $T_{FH}$), regulatory cells (e.g. Treg, and Tr1 cells), NKT cells, tumor infiltrating lymphocytes (TILs), lymphocyte-activated killer cells (LAKs), αβT cells, γδT cells, and similar unique classes of the T-cell lineage. In some embodiments the T cells are activated T-cells.

T cells can be obtained from a number of sources, including peripheral blood leukocytes, bone marrow, lymph node tissue, spleen tissue, and tumors. In some embodiments, peripheral blood leukocytes are obtained from an individual by leukopheresis. Isolating T cells from peripheral blood leukocytes may include lysing the red blood cells and separate peripheral blood leukocytes from monocytes by, for example, centrifugation through, e.g., a PERCOLL™ gradient. A specific subpopulation of T cells, such as CD4+ or CD8+ T cells, can be further isolated by positive or negative selection techniques. For example, negative selection of a T cell population can be accomplished with a combination of antibodies directed to surface markers unique to the cells negatively selected. One suitable technique includes cell sorting via negative magnetic immunoadherence, which utilizes a cocktail of monoclonal antibodies directed to cell surface markers present on the cells negatively selected. For example, to isolate CD4+ cells, a monoclonal antibody cocktail typically includes antibodies to CD14, CD20, CD11b, CD16, HLA-DR, and CD8. The process of negative selection may be used to produce an essentially homogenous population of the desired T cell population. In some embodiments, the T-cell is an alpha/beta T-cell. In some embodiments, the T-cell is a delta/gamma T-cell. In some embodiments, a composition comprises a mixture of two or more (e.g. 2, 3, 4, 5, or more) different kind of T-cells. In some embodiments, the linker conjugated to the T-cell is not associated with an activation domain.

In some embodiments, the cell is a member of an enriched population of cells. One or more desired cell types may be enriched by any suitable method, non-limiting examples of which include treating a population of cells to trigger expansion and/or differentiation to a desired cell type, treatment to stop the growth of undesired cell type(s), treatment to kill or lyse undesired cell type(s), purification of a desired cell type (e.g. purification on an affinity column for retain desired or undesired cell types on the basis of one or more cell surface markers). In some embodiment, the enriched population of cells is a population of cells enriched in gamma/delta T cells (γδ T cells). γδ T cells may be enriched by any suitable method. For example, the percentage of γδ T cells may be expanded in a population of hematolymphoid cells by first administering IL-12 and a ligand of CD2, followed by administering IL-2 and T cell mitogenic stimulus. In some embodiments, expanded γδ T cells can survive under culture conditions for a period of time which is greater than the period of time during which hematolymphoid cells in primary culture survive under the same conditions. Additional methods for expanding γδT cells are described in WO1999046365A1, which is hereby incorporated by reference. In some embodiments, the enriched population of cells is a population of cells enriched in Cytokine Induced Killer (CIK) cells. CIK cells can be generated from peripheral blood mononuclear cells (PBMC) by in-vitro culture in presence of IFN-γ, OKT-3, and IL-2. In some embodiments, high dose Th1-type hormonal stimulation of α/β T-cells with IFN-1, OKT-3 and IL-2 is used to produce CIK AI cells as the enriched population of cells. In some embodiments, the CIK cells are CD3+CD56+ cells. Additional methods for enriching CIK cells are described in US20080241194, which is hereby incorporated by reference.

In some embodiments, a cell embodied in a subject complex or to which a linker is conjugated is a stem cell. In general, "stem cell" refers to a cell that is capable of differentiating into different, more specialized cell types. A stem cell may be multi-potent, pluripotent, or totipotent. A stem cell may be isolated from a subject, from a cell line, or induced from a non-pluripotent cell. Embryonic stem cells may reside in the blastocyst and give rise to embryonic tissues, whereas somatic stem cells may reside in adult tissues for the purpose of tissue regeneration and repair. The terms "pluripotent" and "pluripotency" refer to cells with the ability to give rise to progeny that can undergo differentiation, under appropriate conditions, into cell types that collectively exhibit characteristics associated with cell lineages from the three germ layers (endoderm, mesoderm, and ectoderm). Pluripotent stem cells can contribute to tissues of a prenatal, postnatal or adult organism. A standard art-accepted test, such as the ability to form a teratoma in 8-12 week old SCID mice, can be used to establish the pluripotency of a cell population. However, identification of various pluripotent stem cell characteristics can also be used to identify pluripotent cells. More specifically, human pluripotent stem cells may express at least some, and optionally all, of the markers from the following non-limiting list: SSEA-3, SSEA-4, TRA-1-60, TRA-1-81, TRA-2-49/6E, ALP, Sox2, E-cadherin, UTF-1, Oct4, Lin28, Rex1, and Nanog. An "induced pluripotent stem cell" (iPSC) refers to a pluripotent stem cell artificially derived from a non-pluripotent cell. A non-pluripotent cell can be a cell of lesser potency to self-renew and differentiate than a pluripotent stem cell. Cells of lesser potency can be, but are not limited to, somatic stem cells, tissue specific progenitor cells, primary or secondary cells. Without limitation, a somatic stem cell can be a hematopoietic stem cell, a mesenchymal stem cell, an epithelial stem cell, a skin stem cell or a neural stem cell. Non-pluripotent cells can be reprogrammed to become iPSCs by the introduction of pluripotency genes or proteins, such as Oct4, Sox2, Lin28 and Nanog into the cell. The genes or proteins may be introduced into the differentiated cells by any suitable technique, including plasmid transfection, viral transfection, or direct protein delivery. Following introduction of the pluripotency genes or proteins, the ancestor cells may be cultured. Cells expressing pluripotency markers may be isolated and/or purified to produce a population of iPS cells. In some embodiments, the cell is an embryonic stem cell (ESC), such as from an ESC cell line, non-limiting examples of which include CHB-1 to CHB-12, RUES1 to RUES3, HUES1 to HUES28, HUES45, HUES48, HUES49, HUES53, HUES62 to HUES66, WA01 (H1), WA07 (H7), WA09 (H9), WA13 (H13), WA14 (H14), NYUES1 to NYUES7, MFS5, and UCLA1 to UCLA3. Further examples of stem cells are described in US20140093486, US20130084267, US20120107286, and WO2012172328A1, which are hereby incorporated by reference.

In some embodiments, the cell to be conjugated to a linker is of a cell type that constitutes about or more than about 10%, 20%, 30%, 40%, 50%, 60%, 70%, 80%, 90%, 95%, 99%, or more of the cells in a population, such as an enriched population. In some embodiments, the cell to be conjugated is of a cell type that is substantially the only cell type in a cell population, such as 100% of the cells. In some embodiments, about or more than about 10%, 20%, 30%, 40%, 50%, 60%, 70%, 80%, 90%, 95%, 99%, or more of the cells in a population are conjugated to a linker, such as a polynucleotide linker. In some embodiments, all cells in a population of cells are conjugated to at least one linker.

In some embodiments, one or more cell type, including one or more of the cell types disclosed herein, is a target cell having a biological marker to which a targeting moiety selectively or specifically binds. In general, selective or specific binding is used to refer to a binding interaction above a threshold affinity, such as a binding affinity described herein.

In some embodiments, the therapeutic agent is a virus, or a portion thereof. In some embodiments, the therapeutic agent is a bacteriophage (also referred to as a "phage") or a portion thereof (e.g. all or a portion of a phage tail), and the target cell comprising the biological marker to which the targeting moiety is directed is a bacterial cell. In some embodiments, interaction between the phage and the bacterial cell inhibits growth, survival, or replication of the bacterial cell, such as in a method to treat bacterial infection. Non-limiting examples of phages include a phage from the families Podoviridae, Siphoviridae, Myoviridae, Lipothrixviridae, Plasmaviridae, Corticoviridae, Fuscloviridae, Tectiviridae, Cystoviridae, Leviviridae, Microviridae, Inoviridae plectrovirus, and Inoviridae inovirus. See Ackermann and Dubow (1987) Viruses of Prokaryotes CRC Press, ISBN: 0849360544). In some embodiments the phage is derived from a tailed phage from the families Podoviridae, Siphoviridae, and Myoviridae. In some embodiments the phage is derived by mutagenesis or engineered from a naturally occurring or wild-type tailed phage from the family myoviridae or from the family Siphoviridae. In some embodiments, the phage is essentially unable to replicate in the target bacterium under the conditions of use. Loss of replication activity by an anti-bacterial phage, (also referred to as being unable to replicate, loss of assembly activity, and genetically incompetent anti-bacterial phage), can occur, e.g., through removal of all or critical portions of nucleic acids, inactivation of nucleic acids, removal of structural portions of a phage, e.g., removal of the head of a tailed phage. The replication activity of an anti-bacterial phage in a target bacterium may be measured relative to the replication activity of the parental phage in the host bacterium, or relative the parental phage in the target bacterium. Phage also include phage constructs whose nucleic acid has been partially or totally removed.

In some embodiments, the phage or portion thereof of a therapeutic agent comprises a tail-associated murein-degrading enzyme (TAME) having bactericidal activity. A non-limiting example of a TAME is ORF56 of the staphylococcal myovirus K, and truncations thereof. The therapeutic agent may comprise a TAME homolog from another source, such as from YP_238566 (ORF007 (*Staphylococcus* phage Twort)), YP_406405 (gp29 (*Listeria* bacteriophage P100)), NP_765044 (secretory antigen SsaA-like protein (*Staphylococcus epidermidis* ATCC 12228)), YP_164769 (orf134 (*Lactobacillus plantarum* bacteriophage LP65)), YP_492702 (transfer complex protein TraG (*Staphylococcus aureus* subsp. *aureus* USA300)), AAA71958 (putative (*Staphylococcus aureus*)), NP_765786 (N-acetylmuramoyl-L-alanine amidase (*Staphylococcus epidermidis* ATCC 12228)), YP_189676 (secretory antigen precursor SsaA-related protein (*Staphylococcus epidermidis* RP62A)), YP 189814 (N-acetylmuramoyl-L-alanine amidase (*Staphylococcus epidermidis* RP62A)), and the phage phi11 ORF49, a putative cell wall hydrolase (NP_803302; GeneID: 1258067). The activity will typically be a peptidoglycan degrading enzyme, and may have one or more muraminidase, glucosaminidase, transglycosylase, lysozyme, amidase or endopeptidase enzymatic activities. The enzyme may be capable of degrading of the cell wall, and may have even be characterized as "lytic" to the cell. The enzymes may be derived from phage structures, tails or tail-equivalents in podophage, or interior head proteins of podophage, which provide means for the phage genomic material to enter a bacterial host from the external environment—the entire class of such proteins is referred to as TAME proteins. An example of a TAME protein associated with a tail-equivalent in podophage is the gp16 protein of Phage T7. The gp16 protein is a transglycosylase that attacks peptidoglycan. The gp16 protein aids in DNA injection, but is contained inside the capsid and when ejected during infection, seems to form part of tail. See, e.g., Molineux (1999) The T7 family of bacteriophages. In Encyclopedia of Molecular Biology. Creighton T E, ed. NY, John Wiley & Col, pp. 2495-2507. In some embodiments, the therapeutic agent induces degradation of the cell well of a target bacteria. The target bacteria will typically be those which affect or infect animals, particularly primates. However, various bacteriostatic or bactericidal applications would be advantageously pursued, as will certain public health problems. The bacteria will often fall into the Gram-positive class, though there are other pathological bacteria which are not clearly categorized into one or the other, including *mycobacteria*, spores, or other prokaryotes. Pathogenic or pathological bacterial targets are of most interest, both Gram-positive strains, e.g., *Staphylococcus* species, including *aureus*, and *Streptococcus* species, as well as Gram-negative. Particularly important Gram-negative target species include the genera *Escherichia*, particularly *coli; Pseudomonas*, particularly *aeruginosa; Campylobacter; Salmonella; Neisseria; Helicobacter*; and *Vibrio*. See, e.g., the Merck Manual and the Merck Veterinary Manual. Further examples of phage and other antibacterial proteins useful in related embodiments are described in U.S. Pat. No. 8,202,516, which is incorporated herein by reference.

In some embodiments, a subject complex comprises a targeting unit and a therapeutic unit, each of which comprises a linker, which interact to bring the two units together to form the complex. For example, a first moiety (such as a targeting moiety) that is conjugated to a first linker forms a complex with a second moiety (such as a therapeutic agent or a cell) that is conjugated to a second linker via an interaction between the first and second linkers. In some embodiments, the interaction between the linkers is the formation of a covalent bond. In some embodiments, the interaction between the linkers is a non-covalent interaction, such as electrostatic, hydrophobic, hydrogen bonding, Van Der Waals, or magnetic interactions. In some embodiments, the interaction between the linkers is a reversible interaction, such that the complex formed between the targeting unit and the therapeutic unit is a reversible complex. In general, a reversible complex is a complex that can be disrupted by changing one or more conditions to which the complex is subject, such as the conditions of a solution containing a reversible complex. For example, a reversible interaction may be disrupted by changing temperature (e.g. applying heat), changing pH (e.g. lowering or increasing pH), enzymatic activity (e.g. enzymatic degradation), changing ionic strength (e.g. decreasing salt concentration), or a combination of two or more of these. In some embodiments, the linker interaction is disrupted by applying high heat beyond about 50° C., about 60° C., about 70° C., about 80° C., about 90° C. or even higher. In some embodiments, the linker interaction is disrupted by reducing pH to create an acidic condition below pH5, pH4, pH3 or even lower. In some embodiments, the linker interaction is disrupted by increasing pH to create an alkaline condition above pH8, pH9, pH10, pH11 or even higher. In some embodiments, a reversible complex is one that can be restored after disruption, such as by restoring conditions that favor formation of the complex.

An example of a reversible interaction is the interaction between two complementary polynucleotides. For example, the first and second linkers may form a complex under conditions that favor hybridization between complementary regions of their respective linkers. The complex may be disrupted by heating to a temperature that favors dissociation of the hybridized linkers, then reformed by cooling to a temperature that favors re-annealing. In some embodiments, a complex between the first linker and second linker forms upon exposing the first linker to the second linker, such as by combining in solution. In some embodiments, the complex forms only after treating the combination to trigger an interaction between the first and second linkers. For example, the first linker may be a polynucleotide with a single-stranded region that is complementary to a single-stranded region of the second linker polynucleotide, such that the linker hybridize to one another without further treatment but via the sequence complementarity. As another example, the first linker may be a polynucleotide with a double-stranded region that is complementary to a region of the second linker polynucleotide that is either double- or single-stranded, such that interaction between the first and second linkers is triggered by treating the combine moieties to render the complementary portion(s) of the linker(s) single-stranded.

A linker suitable for conjugating to a subject therapeutic agent or a targeting unit can be a member of a binding pair. A first member of a binding pair generally exhibits a higher affinity for a second member of the binding pair than for a non-member molecule. Examples of binding pairs include, but are not limited to, antigen-antibody, receptor-hormone, receptor-ligand, agonist-antagonist, lectin-carbohydrate, polynucleotide (RNA or DNA) hybridizing sequences, aptamer-target, avidin-biotin, streptavidin-biotin, leucine zipper-target polynucleotide, zinc finger-target polynucleotide, and the like. In some embodiments, the affinity of one member of a binding pair for another member of the binding pair is about or more than about 2, 3, 4, 5, 6, 7, 8, 9, 10, 15, 20, 25, 50, 75, 100, 150, 200, 300, 400, 500, 1000, $1\times10^4$, $1\times10^5$, $1\times10^6$, $1\times10^7$, $1\times10^8$, or more fold greater than the affinity with which the targeting moiety binds a non-target compound. In some embodiments, the binding affinity ($K_D$) between members of a binding pair is about 0.02 to about 200 nM. In some embodiments, the binding affinity is about or less than about 250 nM, 200 nM, 100 nM, 50 nM, 10 nM, 1 nM, 500 pM, 100 pM, 60 pM, 50 pM, 20 pM, 15 pM, 10 pM, 5 pM, 2 pM, or less. Affinity may be measured by any suitable method, such as surface plasmon resonance at a selected temperature (e.g. 25 or 37° C.). In some embodiments, the linker is an exogenous linker that is attached to a cell. In this context, "exogenous" is used to indicate that the linker was not produced by the cell to which it is conjugated. For example, an exogenous linker from a separate source may be mixed with a cell to conjugate the linker to the cell.

In some embodiments, the first and second linkers are polynucleotides, with affinity based on degree of complementarity. The linker polynucleotides may be fully single-stranded, fully double stranded, or comprise one or more single-stranded region and one or more double-stranded region (alternatively referred to as "partially single-stranded). In a partially single-stranded linker polynucleotide, a single stranded region be located at the 3' end and include the 3'-most nucleotide, at the 5' end and include the 5'-most nucleotide, or at a position in between. A single-stranded region may be proximal or distal to the moiety to which it is attached. In some embodiments, a linker polynucleotide is about, or more than about 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, 20 nt, 21 nt, 22 nt, 23 nt, 24 nt, 25 nt, 30 nt, 35 nt, 40 nt, 45 nt, 50 nt, 75 nt, 100 nt, 150 nt, 200 nt, or more in length. In some embodiments, a linker polynucleotide is about or less than about 100 nt, 75 nt, 50 nt, 45 nt, 40 nt, 35 nt, 30 nt, 25 nt, 24 nt, 23 nt, 22 nt, 21 nt, 20 nt, 19 nt, 18 nt, 17 nt, 16 nt, 15 nt, 14 nt, 13 nt, 12 nt, 11 nt, 10 nt, or fewer in length. In some embodiments, where a linker polynucleotide is partially single-stranded, a single-stranded region or double-stranded region is about or more than about 1 nt, 2 nt, 3 nt, 4 nt, 5 nt, 6 nt, 7 nt, 8 nt, 9 nt, 10 nt, 11 nt, 12 nt, 13 nt, 14 nt, 15 nt, 20 nt, 25 nt, 30 nt, 40 nt, 50 nt or more in length. In some embodiments, where a linker polynucleotide is partially single-stranded, a single-stranded region or double-stranded region is about or less than about 50 nt, 45 nt, 40 nt, 35 nt, 30 nt, 25 nt, 24 nt, 23 nt, 22 nt, 21 nt, 20 nt, 19 nt, 18 nt, 17 nt, 16 nt, 15 nt, 14 nt, 13 nt, 12 nt, 11 nt, 10 nt, or fewer in length. Where desired, a linker comprises a single-stranded polynucleotide sequence having a melting temperature (when forms a double-stranded sequence with its complementary strand) higher than about 40° C., 45° C., 50° C., 55° C., 60° C. or even higher.

Where a linker polynucleotide is double-stranded or partially single-stranded, one or both strands may be conjugated to targeting unit or therapeutic unit. The region of complementarity between a first linker polynucleotide and its partner second linker polynucleotide may be fully single-stranded, fully double-stranded, or partially single-stranded. In some embodiments, the region of complementarity is about or more than about 1 nt, 2 nt, 3 nt, 4 nt, 5 nt, 6 nt, 7 nt, 8 nt, 9 nt, 10 nt, 11 nt, 12 nt, 13 nt, 14 nt, 15 nt, 20 nt, 25 nt, 30 nt, 40 nt, 50 nt or more in length. In some embodiments, the region of complementarity is about or less than about 50 nt, 45 nt, 40 nt, 35 nt, 30 nt, 25 nt, 24 nt, 23 nt, 22 nt, 21 nt, 20 nt, 19 nt, 18 nt, 17 nt, 16 nt, 15 nt, 14 nt, 13 nt, 12 nt, 11 nt, 10 nt, or fewer in length.

The particular sequence of a linker or linker pair, and/or the portion(s) thereof that hybridize based on sequence complementarity may be designed in conformance with one or more of a variety of parameters. Parameters include considerations that relate to hybridization conditions, as described herein. Additional considerations include, but are not limited to, minimizing or eliminating complementary with genomic sequences (e.g. of conjugated cell), avoiding potentially immunogenic sequences (e.g. CpG sequences), avoiding sequences predicted to be capable of forming stable secondary structures under hybridization conditions, sequences having a specified length (such as any length described herein, and designing linker pairs (or hybridizing portions thereof) to have the same relative nucleotide composition (e.g. the same percentage of A, T, G, and/or C). Software for identifying complementarity and/or identity with a reference genome are available, such as the BLAST alignment tool available at blast.ncbi.nlm.nih.gov/Blast.cgi. Other tools useful for designing linkers that meet specified requirements are available online, such as those provided by Integrated DNA Technologies at www.idtdna.com/pages/scitools. In some embodiments, linkers comprise or consist of a pair of sequences selected from SEQ ID NO: 1 and SEQ ID NO: 2; SEQ ID NO: 3 and SEQ ID NO: 4; SEQ ID NO: 5 and SEQ ID NO: 6; SEQ ID NO: 7 and SEQ ID NO:8; SEQ ID NO: 9 and SEQ ID NO: 10; SEQ ID NO 11 and SEQ ID NO: 12; SEQ ID NO: 13 and SEQ ID NO: 14; SEQ ID NO: 15 and SEQ ID NO: 16; SEQ ID NO: 17 and SEQ ID NO: 18; SEQ ID NO: 19 and SEQ ID NO: 20; SEQ ID NO: 21 and SEQ ID NO: 22; and SEQ ID NO: 23 and SEQ ID NO: 24, as shown in Table 1. Sequences are shown in the 5' to 3' orientation.

TABLE 1

| SEQ ID NO: | Sequence |
|---|---|
| SEQ ID NO: 1 | AAAAAAAAAAAAAAAAAAAA |
| SEQ ID NO: 2 | TTTTTTTTTTTTTTTTTTTT |
| SEQ ID NO: 3 | ACTGACTGACTGACTGACTG |
| SEQ ID NO: 4 | CAGTCAGTCAGTCAGTCAGT |
| SEQ ID NO: 5 | TGTGTGTGTGTGTGTGTGTG |
| SEQ ID NO: 6 | ACACACACACACACACACAC |
| SEQ ID NO: 7 | GTAACGATCCAGCTGTCACT |
| SEQ ID NO: 8 | AGTGACAGCTGGATCGTTAC |
| SEQ ID NO: 9 | TCATACGACTCACTCTAGGG |
| SEQ ID NO: 10 | CCCTAGAGTGAGTCGTATGA |
| SEQ ID NO: 11 | ACTGATGGTAATCTGCACCT |
| SEQ ID NO: 12 | AGGTGCAGATTACCATCAGT |
| SEQ ID NO: 13 | AAAAAAAAAAAAAAAAAAAAAAAAAAAAAAAAAAAAAAAA |
| SEQ ID NO: 14 | TTTTTTTTTTTTTTTTTTTTTTTTTTTTTTTTTTTTTTTT |
| SEQ ID NO: 15 | ACTGACTGACTGACTGACTGACTGACTGACTGACTGACTG |
| SEQ ID NO: 16 | CAGTCAGTCAGTCAGTCAGTCAGTCAGTCAGTCAGTCAGT |
| SEQ ID NO: 17 | TGTGTGTGTGTGTGTGTGTGTGTGTGTGTGTGTGTGTGTG |
| SEQ ID NO: 18 | ACACACACACACACACACACACACACACACACACACACAC |
| SEQ ID NO: 19 | GTAACGATCCAGCTGTCACTGTAACGATCCAGCTGTCACT |
| SEQ ID NO: 20 | AGTGACAGCTGGATCGTTACAGTGACAGCTGGATCGTTAC |

TABLE 1-continued

SEQ ID NO: 21  TCATACGACTCACTCTAGGGTCATACGACTCACTCTAGGG

SEQ ID NO: 22  CCCTAGAGTGAGTCGTATGACCCTAGAGTGAGTCGTATGA

SEQ ID NO: 23  ACTGATGGTAATCTGCACCTACTGATGGTAATCTGCACCT

SEQ ID NO: 24  AGGTGCAGATTACCATCAGTAGGTGCAGATTACCATCAGT

In some embodiments, the first linker and the second linker interact indirectly, via interaction with one or more intermediate compounds. For example, a first linker polynucleotide and a second linker polynucleotides may interact via complementarity with a different portion of an adapter polynucleotide. An adapter polynucleotide can comprise DNA, RNA, nucleotide analogues, non-canonical nucleotides, labeled nucleotides, modified nucleotides, or combinations thereof. Adapter polynucleotides can be single-stranded, double-stranded, or partial duplex. In general, a partial-duplex adapter comprises one or more single-stranded regions and one or more double-stranded regions. Double-stranded adapters can comprise two separate oligonucleotides hybridized to one another (also referred to as an "oligonucleotide duplex"), and hybridization may leave one or more 3' overhangs, one or more 5' overhangs, one or more bulges resulting from mismatched and/or unpaired nucleotides, or any combination of these. An adapter polynucleotide that interacts with both the first linker polynucleotide and the second linker polynucleotide may comprise a contiguous backbone. For example, the first and second linkers may hybridize to different portions of a single-stranded adapter polynucleotide. Alternatively, the first linker polynucleotide may hybridize to a first strand of a double-stranded linker, the second linker polynucleotide may hybridize to a second strand of a double-stranded linker, and the first and second strands of the adapter may hybridize with one another, such that the first and second linkers interact indirectly via sequence complementarity with the double-stranded adapter polynucleotide. An adapter polynucleotide may alternatively comprise a discontiguous backbone, such as when two or more double-stranded adapter polynucleotides (e.g. 2, 3, 4, 5, or more) hybridize in a chain, with the first linker polynucleotide hybridizing to one end of the chain and the second linker polynucleotide hybridizing to the other end of the chain.

In some embodiments, a component of a complex (e.g. a therapeutic agent, a linker, or a targeting moiety) is a peptide that is designed or selected to minimize immunogenicity. Programs for assessing potential immunogenicity of peptide sequences are available, such as tools provided as part of the Epitope Database Analysis Resource, available at tools.immuneepitope.org/main/html/tcell_tools.html.

The linker and the moieties described herein can be conjugated by any suitable means known in the art. A linker conjugated to a targeting unit (e.g., an antibody) or therapeutic unit (e.g., a cell) may be conjugated via a covalent or a non-covalent linkage. In some embodiments, the linker is conjugated to a native functional group of a targeting unit or therapeutic unit, such as natively on a surface of a cell or a native group in a protein. The cell surface can include any suitable native functional group, such as amino acids and sugars. For example, reagents including maleimide, disulfide and the process of acylation can be used to form a direct covalent bond with a cysteine on a cell surface protein. Amide coupling can be used at an aspartamate and glutamate to form an amide bond. Diazonium coupling, acylation, and alkylation can be used at a tyrosine on the cell surface to form an amide bond linkage. It is possible that any of the amino acids (20 amino acids or any unnatural amino acids) can be used to form the direct covalent bond that is the attachment of the oligonucleotide with the cell surface. The 20 amino acids are isoleucine, leucine, lysine, methionine, phenylalanine, threonine, tryptophan, and valine (essential amino acids), and alanine, asparagine, aspartate, cysteine, glutamate, glutamine, glycine, proline, serine, and tyrosine, the nonessential amino acids, and also arginine and histidine. In some embodiments, the native functional group can be an amino acid such as lysine, cysteine, tyrosine, threonine, serine, aspartic acid, glutamic acid or tryptophan. In other embodiments, the native functional group is lysine. In some other embodiments, the native functional group can be an N-terminal serine or threonine.

In some embodiments, the linker may be conjugated to the targeting unit or therapeutic unit using a coupling group. For example, the coupling group can be an activated ester (e.g. NHS ester, 1-ethyl-3-(3-dimethylaminopropyl) carbodiimide (EDC) ester, dicyclohcxylcarbodiimide (DCC) ester, etc.), or an alkyl or acyl halide (e.g. —Cl, —Br, —I). In some embodiments, the activated ester is isolated and/or purified. In some embodiments, the activated ester is generated and/or used in situ. In some cases, the coupling group can directly conjugate to the therapeutic agent (e.g., surface of a cell used as a therapeutic agent) without pre-modification of the native functional group (e.g. amino acids). For example, the linker can be conjugated to the targeting unit or therapeutic unit by formation of a bond (e.g. an amide or ester bond) with an amino acid on a targeting moeity (e.g. antibody, aptamer) or a cell surface. In some embodiments, the coupling group is an NHS ester, which reacts with a nucleophilic native functional group on the targeting unit or therapeutic unit, resulting in an acylated product. For example, the native functional group can be an amine, which is conjugated via the NHS ester to form an amide. Alternatively, the native functional group can be a hydroxyl or a sulfhydryl group, which can be conjugated via the NHS ester to form an ester or a sulfohydryl ester linkage, respectively.

In some embodiments, the linker can be conjugated to the targeting unit or therapeutic unit using a bifunctional crosslinker. The bifunctional crosslinker can comprise two different reactive groups capable of coupling to two different functional targets such as peptides, proteins, macromolecules, semiconductor nanocrystals, or substrate. The two reactive groups can be the same or different and include but are not limited to such reactive groups as thiol, carboxylate, carbonyl, amine, hydroxyl, aldehyde, ketone, active hydrogen, ester, sulfhydryl or photoreactive moieties. In some embodiments, a cross-linker can have one amine-reactive group and a thiol-reactive group on the functional ends. In other embodiments, the bifuncitonal crosslinker can be a NHS-PEO-Maleimide, which comprise an N-hydroxysuccinimide (NHS) ester and a maleimide group that allow covalent conjugation of amine- and sulfhydryl-containing molecules. Further examples of heterobifunctional crosslinkers that may be used to conjugate the linker to the targeting unit or therapeutic unit include but are not limited to: amine-reactive+sulfhydryl-reactive crosslinkers, carbonyl-reactive+sulfhydryl-reactive crosslinkers, amine-reactive+photoreactive crosslinkers, sulfhydryl-reactive+photoreactive crosslinkers, carbonyl-reactive+photoreactive crosslinkers, carboxylate-reactive+photoreactive crosslinkers, and arginine-reactive+photoreactive crosslinkers.

Typical crosslinkers can be classified in the following categories (with exemplary functional groups):
1. Amine-reactive: the cross-linker couples to an amine (NH2) containing molecule, e.g. isothiocyanates, isocyanates, acyl azides, NHS esters, sulfonyl chlorides, aldehydes and glyoxals, epoxides and oxiranes, carbonates, arylating agents, imidoesters, carbodiimides, anhydrides, alkynes;
2. Thiol-reactive: the cross-linker couple to a sulfhydryl (SH) containing molecule, e.g. haloacetyl and alkyl halide derivates, maleimides, aziridines, acryloyl derivatives, arylating agents, thiol-disulfides exchange reagents;
3. Carboxylate-reactive: the cross-linker couple to a carboxylic acid (COOH) containing molecule, e.g. diazoalkanes and diazoacetyl compounds, such as carbonyldiimidazoles and carbodiimides;
4. Hydroxyl-reactive: the cross-linker couple to a hydroxyl (—OH) containing molecule, e.g. epoxides and oxiranes, carbonyldiimidazole, oxidation with periodate, N,N'-disuccinimidyl carbonate or N-hydroxylsuccimidyl chloroformate, enzymatic oxidation, alkyl halogens, isocyanates;
5. Aldehyde- and ketone-reactive: the cross-linker couple to an aldehyde (—CHO) or ketone (R2CO) containing molecule, e.g. hydrazine derivatives for schiff base formation or reduction amination;
6. Active hydrogen-reactive, e.g. diazonium derivatives for mannich condensation and iodination reactions; and
7. Photo-reactive, e.g. aryl azides and halogenated aryl azides, benzophenones, diazo compounds, diazirine derivatives.

For each category, i.e. whether a particular chemical targets a functional group, there are some subcategories, because some reactive groups are capable of reacting with several functional groups. For each of these subcategories there are many examples of chemicals. Many of these chemicals and the above list of subcategories can be found in, "*Bioconjugate Techniques*" by Greg T Hermanson, Academic Press, San Diego, 1996, which is hereby incorporated by reference.

In another embodiment, crosslinkers comprising polyethylene glycol (PEG), also referred to as polyethyleneoxide (PEO), spacers can be used as alternatives to reagents with purely hydrocarbon spacer arms. PEG spacers improve water solubility of reagent and conjugate, reduce the potential for aggregation of the conjugate, and increases flexibility of the crosslink, resulting in reduced immunogenic response to the spacer itself. By contrast to typical PEG reagents that contain heterogeneous mixtures of different PEG chain lengths, these PEO reagents are homogeneous compounds of defined molecular weight and spacer 5 arm length, providing greater precision in optimization and characterization of crosslinking applications. For example, succinimidyl-[(N-maleimidopropionamido)-hexaethyleneglycol] ester was used in the examples to make a stock solution by dissolving 5 mg of NHS-PEO6-maleimide (Pierce Biotechnology, Inc. Rockford, Ill. 61105).

In some embodiments, the conjugation can result in a carboxyl or a carbonyl group, or amino or thio equivalents thereof. Examples of such groups include but are not limited to ketones, imides, thiones, amides, imidamides, thioamides, esters, imidoesters, thioesters, carbamates, ureas, thioureas, carbonates, carbonimidates and carbonthioates. In some embodiments, the conjugation can result in a hydrazone or an oxime bond. In some embodiments, the conjugation may result in a disulfide bond. In some embodiments, the linker can be conjugated using Native Chemical Ligation (NCL) methods. Additional examples of linkers and coupling groups are disclosed in WO2010118235A1, which is hereby incorporated by reference.

In some embodiments, about or at least about 500, 1000, 10000, 100000, 500000, 750000, 1000000, 5000000, $10^7$, or more linkers are conjugated to a single targeting unit (e.g., encompassing a targeting moiety) or therapeutic unit (e.g., a single cell surface). In some cases, the linker(s) can be directly conjugated to the cell surface. A cell is conjugated "directly" when the cell membrane (cell surface, outside of the cell, or component thereof) is not actively modified or changed before the attachment of the linker. Specifically, since the attachment is to a native functional group on the cell surface, "directly" means that the native functional group is not modified before the linker conjugation.

The buffer solution for the conjugation can be selected based on the choice of chemical linker or crosslinker and maintaining growth conditions for cells (i.e., to prevent cell lysis). In some embodiments, the buffer solution range is from pH 6-8 and does not contain the same functional groups used in the chemical linker to react with the conjugation linker (e.g. single-stranded polynucleotide). A pH of 7.2 can be used, but the pH does not have to be neutral, and typically is dependent on compatibility with the chemical reaction and the cellular conditions.

In some embodiments, the buffer solution is a phosphate buffer solution of neutral pH such that an N-hydrosuccinimide (NHS) ester (e.g., NHS-PEO-maleimide) may be used as the coupling group. The reaction is generally carried out under conditions that allow the conjugation of the linker and the moiety (e.g. antibody, aptamer, cell surface). In some embodiments where an NHS ester crosslinker and phosphate buffer solution is used, the reactions are carried out at neutral pH (e.g., pH 7.2) and at room temperature for a specified period of time (e.g. about 1, 3, 5, 10, 15, 20, 30, 45, 60 or more minutes).

The linker can be a polynucleotide. Exemplary polynucleotides include, but are not limited to, deoxy-ribonucleic acid (DNA), ribonucleic acid (RNA), peptide nucleic acid (PNA), morpholino and locked nucleic acid (LNA), glycol nucleic acid (GNA), threose nucleic acid (TNA), single-stranded DNA (ssDNA), aptamer, and others nucleic acid moieties such as fluorinated nucleic acids.

The length of the polynucleotide used to attach on the therapeutic unit or the targeting unit can range from about 4 nucleotides to about 500 nucleotides. For example, the length of the polynucleotide can be between about 12 to about 40 nucleotides, or about 20 to about 25 nucleotides. In some embodiments, the length of the polynucleotide can be at least about 5, 10, 15, 20, 25, 30, 35, 40, 45, 50, 55, 60, 65, 70, 75, 80, 85, 90, 95, 100, 120, 140, 160, 180, 200, 300, 400 or 500 bases. In some embodiments, the length of the polynucleotide can be less than about 5, 10, 15, 20, 25, 30, 35, 40, 45, 50, 55, 60, 65, 70, 75, 80, 85, 90, 95, 100, 120, 140, 160, 180, 200, 300, 400 or 500 bases.

In some cases, the linker can be an aptamer. Aptamers are oligonucleotides that can adopt a three-dimensional structure and bind a specific target molecule. Aptamers can be created by selecting them from a large random sequence pool, but natural aptamers also exist (e.g. riboswitches). Aptamers can be used for both basic research and clinical purposes as macromolecular drugs. Aptamers can be combined with ribozymes to self-cleave in the presence of their target molecule. These compound molecules have additional research, industrial and clinical applications. DNA or RNA aptamers are short strands of nucleic acid moieties. Aptamers can be nucleic acid species that have been engineered through repeated rounds of in vitro selection or equivalently, SELEX (systematic evolution of ligands by exponential enrichment) to bind to various molecular targets such as small molecules, proteins, nucleic acids, and even cells, tissues and organisms. Aptamers are useful in biotechnological and therapeutic applications as they offer molecular recognition properties that rival that of the commonly used biomolecule, antibodies. In addition to their discriminate recognition, aptamers offer advantages over antibodies as they can be engineered completely in a test tube, are readily produced by chemical synthesis, possess desirable storage properties, and elicit little or no immunogenicity in therapeutic applications. Aptamer selection includes a nucleic acid-based genetic regulatory element called a riboswitch that possesses similar molecular recognition properties to the artificially made aptamers. This type of aptamer is a new mode of genetic regulation.

Another class of aptamers that can be used includes smart aptamers, which have pre-defined equilibrium (Kd), rate ($k_{off}$, $k_{on}$) constants and thermodynamic (H, S) parameters of aptamer-target interaction. The aptamer can be selected by kinetic capillary electrophoresis. Unmodified aptamer applications currently focus on treating transient conditions such as blood clotting, or treating organs such as the eye where local delivery is possible. This rapid clearance can be an advantage in applications such as in vivo diagnostic imaging. An example is a tenascin-binding aptamer under development for cancer imaging. Several modifications, such as 2'-fluorine-substituted pyrimidines, polyethylene glycol (PEG) linkage, etc. (both of which are used in Macugen, an FDA-approved aptamer) are available to scientists with which to increase the half-life of aptamers easily to the day or even week time scale.

In some embodiments, a linker comprises polynucleotide having a sequence that can be used as an identifying sequence, a barcode sequence, a probe, a capture sequence for hybridization, a recognition sequence, a gene expression control sequence, a gene sequence, enhancers, and/or sequences incorporating or derived from naturally-occurring enzymes, proteins, or other sequences.

In some embodiments, the linker polynucleotide sequences attached to a given cell can be the same. In another embodiment, the linker polynucleotide sequences attached to a given cell can be different. This may allow the attachment of different polynucleotides for multiples uses. For example, one polynucleotide can be used to capture the cell at a particular placement, and another polynucleotide can provide hybridization or activated sequences to accomplish a specific activity or utility.

Utilizing linkers reversible or irreversible in the manner disclosed herein can generate therapeutic units including but not limited to living cells that comprise a plurality of targeting units.

In some embodiments, the disclosure provides a cell comprises at least two different exogenous targeting units complexed to its outer surface (e.g. a first type and a second type), wherein each of the different exogenous targeting units comprises a distinct targeting moiety that is not produced by the cell to which it is complexed, and binds specifically to a different antigen (e.g. a first type specifically binding to a first antigen and a second type specifically binding to a second antigen). In some embodiments, the cell is complexed to more than 2, 3, 4, 5, 6, 7, 8, 9, 10, 15, 20, or more different exogenous targeting units. The cell can be any desirable cell type, such as a cell type described herein or known in the art. The targeting moieties can be any suitable targeting moiety, such as the ones described herein or know in the art. Although specifically binding distinct targets, two or more different targeting moieties may be of the same or different class of molecule. For example, two may be antibodies, or one may be an antibody and another may be a receptor ligand. Different targeting moieties may be conjugated to a cell by the same or different linkers. For example, the cell may be complexed to multiple copies of a single first linker, and two or more different targeting moieties may be complexed to one or more copies of the same second linker. Alternatively, the cell may be complexed with multiple copies of two or more different first linkers, each of the different first linkers capable of specifically interacting with a corresponding second linker uniquely associated with one of the target moieties. Combinations are also possible, such that two or more different targeting moieties are conjugated to identical linkers while one or more other targeting moieties are conjugated to different linkers. In some embodiments, the ratio of one targeting unit to another targeting unit on the same cell surface is 1 to X, where X is about or more than about 1, 1.5, 2, 3, 4, 5, 6, 7, 8, 9, 10, 15, 20, 25, 50, 75, 100, or more. For example, a cell via the use of linkers may comprise on its outer surface a first targeting moiety, namely an anti-erb2 antibody, and a second targeting moiety, namely an anti-EGFR antibody. In some embodiments, a cell is complexed to antibodies directed to two or more of: Her2, Her3, EGFR, CD20, CD19, Erb2, Erb3, CD28, IGF1R, IMC-1121, Met, VEGF, PDGFRα, PDGFRβ, CD22, CD79b, CD32B, IGF-1, IGF-2, OPN, Ang-2, VEGFR, EpCAM. In some embodiments, a cell is complexed to a combination of antibodies selected from the following combinations: anti-her2 and anti-her3, anti-EGFR and anti-her2, antiCD20 and antiCD19, anti-erb2 and anti-erb3, antiCD20 and antiCD28, antiCD19 and antiCD28, anti-her2 and anti-IGF-1R, anti-EGFR and anti-IMC-1121, anti-EGFR and anti-Met, anti-EGFR and anti-VEGF, anti-PDGFRα and anti-PDGFRβ, anti-CD20 and anti-CD22, anti-CD79b and anti-CD32B, anti-IGF-1 and anti-IGF-2, anti-VEGF and anti-OPN, anti-VEGF and anti-Ang-2, anti-her2 and anti-VEGF, anti-PDGFRβ and anti-VEGFR, anti-her2 and anti-EpCAM, anti-CD19 and anti-CD22. In some embodiments, a cell is complexed to antibodies directed to two or more of Erb2, Erb3, EGFR, her1, her2, her3, her4, IGF-1R. In some embodiments, a cell is complexed to antibodies directed to two or more of VEGFR1, VEGFR2, VEGFR3.

In some embodiment, the disclosure provides a conjugated live cell comprising a targeting moiety is not produced by the cell. Specifically, the targeting moiety is not synthesized by the cell via the process of transcription and translation, but rather become associated with the cell by exogenous means.

In some embodiments, administering a complex comprising a targeting unit and a therapeutic unit to target a cell enhances activity of the therapeutic agent at the target cell to a greater degree as compared to administering either the therapeutic agent or the targeting moiety alone. This is sometimes referred to as a synergistic effect. For example, by targeting the therapeutic agent to the target cell by means of the targeting unit, administering the complex may reduce off-target effects associated with administering the therapeutic agent alone, and/or may reduce the dose necessary to achieve a particular therapeutic result. In some embodiments, a synergistically effective therapeutic amount of a complex produces a greater effect than the additive effects of the members of the complex when used alone.

In another aspect, the disclosure provides a population of effector cells (e.g. T cells) in accordance with any of the embodiments disclosed herein. In some embodiments, the population comprises effector cells complexed with targeting units exhibiting binding specificity to one or more biological markers present on a cell of a target cell population. In some embodiments, the population of effector cells is characterized in that upon exposing the effector cell population to a population of the target cells in an in vitro cell death assay, the population of effector cells induces death of the target cells. In some embodiments, cell death is induced in about or more than about 10%, 20%, 30%, 40%, 50%, 60%, 70%, 80%, 90%, 95%, 99%, or up to 100% of the target cells in the target cell population. In some embodiments, the desired amount of target cell death in a target cell population is reached by about or less than about 48, 24, 18, 12, 11, 10, 9, 8, 7, 6, 5, 4, 3, 2, or 1 hours. In some embodiments, the ratio of effector cells to target cells in a cell death assay is about or less than about X to 1, wherein X is 0.5, 1, 2, 3, 4, 5, 6, 7, 8, 9, 10, 15, 20, 25, 50, 75, 100, 150, 200, 250, 500, or more. In some embodiments, the amount of cell death induced by the complexed effector cells is about or more than about 2-fold, 3-fold, 4-fold, 5-fold, 6-fold, 7-fold, 8-fold, 9-fold, 10-fold, 15-fold, 20-fold, 25-fold, 50-fold, 75-fold, 100-fold, 200-fold, 250-fold, 500-fold, 1000-fold, or 10000-fold greater than the amount of cell death induced by a corresponding population of effector cells that are not complexed with the targeting unit. An example method for preparing a reference population of corresponding effector cells that are not complexed with a targeting unit includes dividing a population of effector cells into two subpopulations, one that is treated to form complexes with targeting units as described herein and one that is untreated. A variety of cell death assays may be employed to determine the ability of a population of complexed effector cells to induce death of target cells. Examples of such methods are provided herein.

Methods:

In one aspect, the disclosure provides a method of producing a conjugated cell complexed with a targeting unit, such as conjugated cells and targeting units as described herein. In some embodiments, the method comprises (a) reacting a targeting moiety with a first polynucleotide to produce a targeting unit comprising the targeting moiety conjugated to the first polynucleotide; (b) reacting a live cell with a second polynucleotide to produce a conjugated cell comprising the second polynucleotide conjugated to the surface of the live cell; and (c) combining the targeting unit and the conjugated cell under conditions effective to form a complex between the conjugated live cell and the targeting unit via the first polynucleotide hybridizing to the second polynucleotide based on sequence complementarity. Any of the targeting unit comprising a targeting moiety disclosed herein or known in the art can be utilized in practicing the subject methods. In some embodiments, the targeting moiety comprises a peptide or a protein. For example, the target moiety can comprise an antibody. In some embodiments, the targeting moiety comprises an aptamer. Similarly, any of the cells disclosed herein or known in the art can be utilized in the subject methods.

A wide variety of techniques are know in the art to effect the steps of reacting a targeting moiety with a first polynucleotide to produce a targeting unit, and the step of reacting a live cell with a second polynucleotide to produce a conjugated cell. For example, the first polynucleotide can be conjugated to the targeting moiety using a bifunctional crosslinker. The bifunctional crosslinker can comprise two different reactive groups capable of coupling to two different functional targets such as peptides, proteins, macromolecules, semiconductor nanocrystals, or substrate. The two reactive groups can be the same or different and include but are not limited to such reactive groups as thiol, carboxylate, carbonyl, amine, hydroxyl, aldehyde, ketone, active hydrogen, ester, sulfhydryl or photoreactive moieties. In some embodiments, a cross-linker can have one amine-reactive group and a thiol-reactive group on the functional ends. In other embodiments, the bifunctional crosslinker can be a NHS-PEO-Maleimide, which comprise an N-hydroxysuccinimide (NHS) ester and a maleimide group that allow covalent conjugation of amine- and sulfhydryl-containing molecules.

In practicing the subject methods, the first and/or second polynucleotide can be independently a DNA, an RNA or a peptide nucleic acid (PNA) molecule, or a combination thereof. The first and/or second polynucleotide can comprise at least about 5, 10, 15, 20, 25, 30, 35, 40, 45, 50, 55, 60, 65, 70, 75, 80, 85, 90, 95, 100, 120, 140, 160, 180, 200, 300, 400 or 500 bases. The first and the second polynucleotide can be fully or substantially complementary to each other. For example, the first and the second polynucleotide can share at least about 50%, 60%, 70%, 80%, 90%, 95%, 99% or 100% complementarity over at least about 5, 10, 15, 20, 25, 30, 35, 40, 45, 50, 55, 60, 65, 70, 75, 80, 85, 90, 95, 100, 120, 140, 160, 180, 200, 300, 400 or 500 bases pairs. In some cases, the first polynucleotide can be provided in excess to the second polynucleotide. For example, the first polynucleotide can be provided in at least about 1.1, 1.2, 1.3, 1.4, 1.5, 1.6, 1.7, 1.8, 1.9, 2.0, 2.5, 3.0, 3.5, 4.0, 4.5, 5.0, 6.0, 7.0, 8.0, 9.0, 10.0, 15, 20, 25, 30, 40, 50, 60, 70, 80, 90, 100, 200, 300, 400, 500, 600, 700, 800, 900, or 1000 times the amount of the second polynucleotide. In some cases, the second polynucleotide can be provided in excess to the first polynucleotide. For example, the second polynucleotide can be provided in at least about 1.1, 1.2, 1.3, 1.4, 1.5, 1.6, 1.7, 1.8, 1.9, 2.0, 2.5, 3.0, 3.5, 4.0, 4.5, 5.0, 6.0, 7.0, 8.0, 9.0, 10.0, 15, 20, 25, 30, 40, 50, 60, 70, 80, 90, 100, 200, 300, 400, 500, 600, 700, 800, 900, or 1000 times the amount of the first polynucleotide. Additional examples of methods for conjugating polynucleotides to cells are disclosed in WO2010118235A1, which is hereby incorporated by reference.

The conjugated targeting unit and the conjugated cell are combined under conditions effective to form a complex via the first polynucleotide hybridizing to the second polynucleotide based on sequence complementarity. Conditions for forming the complex via sequence complementarity are known in the art, and may vary with a number of factors, such as length, complexity, and nucleotide composition of sequences to be annealed. Condition parameters that may be varied to achieve hybridization include, but are not limited to, temperature, pH, salt concentration, buffers, incubation time, and others known in the art. Alternatively, the linkers themselves may be designed in the first instance to favor hybridization under a desired set of reaction conditions. Linker parameters that may be varied to achieve hybridization under certain conditions (or range of conditions) include, but are not limited to, sequence composition (e.g.

G-C content), sequence length, sequence complexity (e.g. repeated single-nucleotide runs or randomly generated sequences), stability of potential intra-strand interactions, melting temperature, and the like. In some embodiments, linkers are designed to have about or less about 90%, 80%, 70%, 60%, 50%, 40%, 30%, 20%, 10%, or lower GC content. In some embodiments, the linkers are selected to have a about or more than about, 10%, 20%, 30%, 40%, 50%, 60%, 70%, 80%, 90%, or more GC content. In some embodiments, linkers are designed to comprise or consist of sequences of 1, 2, 3, 4, 5, 6, 7, 8, 9, or 10 nucleotides repeated 1, 2, 3, 4, 5, 6, 7, 8, 9, 10, 15, or 20 times, or repeated until reaching the end of the linker (e.g. AAA . . . , or ATAT . . . ). In some embodiments, linkers are selected to have a Tm of about or more than about 30° C., 35° C., 40° C., 45° C., 50° C., 55° C., 60° C., 65° C., 70° C., 75° C., 80° C., 85° C., or higher. Software for selecting subsequences, for evaluating the characteristics of a selected sequence, and for generating sequences that meet specified parameters are known to those skilled in the art. An example set of such tools is provided by Integrated DNA Technologies, and is available at www.idtdna.com/pages/scitools.

In one aspect, the disclosure provides a method of delivering a therapeutic agent to a target cell comprising a biological marker. In some embodiments, the method comprises administering to the target cell a complex comprising a targeting unit and a therapeutic unit in accordance with any embodiment of the present disclosure, wherein the therapeutic agent is delivered to the cell via the targeting moiety specifically binding to the biological marker. In some embodiments, the complex is administered to the target cell in vivo, such as to a cell in a subject. Complexes administered to a subject may be in any suitable form, such as a component of a pharmaceutical composition, which may additionally comprise one or more pharmaceutically acceptable carriers and optionally one or more additional therapeutic agents (such as in a combination composition). Pharmaceutically acceptable carriers include, but are not limited to, solvents, dispersion media, coatings, antibacterial and antifungal agents, isotonic and absorption delaying agents, and the like, compatible with pharmaceutical administration. See for example, Remington's Pharmaceutical Sciences (2005). Formulations suitable for parenteral administration, for example, include aqueous sterile injection solutions, which may contain antioxidants, buffers, bacteriostats, and solutes that render the formulation isotonic with the blood of the intended recipient; and aqueous and nonaqueous sterile suspensions that may include suspending agents and thickening agents. Supplementary active compounds can also be incorporated into the compositions. Pharmaceutical compositions can be included in a container, pack, or dispenser together with instructions for administration. A pharmaceutical composition typically is formulated to be compatible with its intended route of administration. Examples of routes of administration include parenteral, e.g., intravenous, intradermal, subcutaneous, oral (e.g., inhalation), transdermal (topical), transmucosal, and rectal administrations. Solutions or suspensions used for parenteral, intradermal, or subcutaneous application can include one or more of the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

In some embodiments, the biological marker is associated with a target cell by way of increased concentration of the marker in a fluid surrounding the target cell or a tissue in which it resides than is found in fluid more distant from the target cell, such as where a cell secretes or otherwise releases the biological marker (also referred to as extracellular markers). In some embodiments, the extracellular marker is a marker secreted or otherwise released from a cell in response to cell or tissue damage. For example, CK-MB and Troponin I are released 4 to 8 hours after the onset of chest pain, and are released after irreversible injury (i.e., necrosis) has occurred. Nourin-1 is an inflammatory polypeptide released within 5 minutes by heart tissues in response to myocardial ischemia. In some embodiments, the therapeutic agent is a cell, the delivery of which to a target tissue containing the target cell that released the biological marker induces tissue repair. For example, a stem cell or cardiomyocyte complexed with a targeting unit that targets an extracellular marker associated with cardiac tissue damage may be delivered to the damaged tissue by virtue of the targeting unit. Delivered cells may then differentiate and/or multiply to repair and replace the damaged tissue by producing new cardiac tissue.

In some embodiments, the complex is administered to the cell in vitro, such as in cell culture. Target cells in culture may be free in solution or adherent. Typically, cells are maintained in culture medium. Culture media can be any known physiologically acceptable liquid culture medium that supports cell viability and proliferation under a variety of conditions. The composition of the media may vary with the cell type being cultured. The culture medium may contain organic and inorganic components required for cell proliferation and may contain standard medium components such as, for example, AIM V, IMDM, MEM, DMEM, RPMI 1640, Alpha Medium or McCoy's Medium, which can use combinations of serum albumin, cholesterol and/or lecithin selenium and inorganic salts. Cultures are typically carried out at a pH which approximates physiological conditions, e.g., 6.9 to 7.4. The medium is typically exposed to an oxygen-containing atmosphere which contains from 4 to 20 vol. percent oxygen, such as 6 to 8 vol. percent oxygen. Target cells may be from a cell line. In some embodiments, cells are derived from a subject for treatment under in vitro conditions, and subsequent reintroduction into the subject (also referred to as "ex vivo" treatment).

In some embodiments, the therapeutic agent is an epitope or a bacterial cell, and the target cell comprising the biological marker is an antigen presenting cell. Administration of the complex may therefore function as a vaccine, such that administration of the complex triggers an immune response to the epitope that is stronger and/or faster than is stimulated by delivery of the epitope alone. For example, administering the complex may reduce the presence of a target pathogen by about or more than about 25%, 30%, 35%, 40%, 45%, 50%, 60%, 70%, 80%, 90%, 99%, or more after a measurement period. In some embodiments, the measurement period is about or less than about 14, 12, 10, 9, 8, 7, 6, 5, or fewer days; 8, 7, 6, 5, 4, 3, 2, or fewer weeks; or 6, 5, 4, 3, 2, 1, or fewer months. The epitope may be a self- or non-self-epitope. Self-epitopes refer to epitopes associated with a subject's own cells, whereas non-self-epitopes refer to epitopes derived from other than the subject's own cells. In some embodiments, the self-epitope is a cancer cell or a portion thereof (e.g. a cell surface marker, protein, or nucleic acid). In some embodiments, the non-self epitope is an epitope associated with a pathogen, such a bacterium, a virus, a fungus, or a parasite. The therapeutic agent may be the entire pathogen or a portion thereof (e.g. a surface protein, a non-surface protein, or a polynucleotide). Examples of infectious virus to which stimulation of a protective immune response is desirable include: Retroviridae (e.g., human immunodeficiency viruses, such as HIV-1 (also referred to as HTLV-111, LAV or HTLV-III/LAV, or HIV-III; and other isolates, such as HIV-LP; Picornaviridae (e.g., polio viruses, hepatitis A virus; enteroviruses, human coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arena viridae (hemorrhagic fever viruses); Reoviridae (e.g., reoviruses, orbiviurses and rotaviruses); Birnaviridae; Hepadnaviridae (Hepatitis B virus); Parvoviridae (parvo viruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), heqpes viruses'); Poxviridae (variola viruses, vaccinia viruses, pox viruses); and Iridoviridae (e.g., African swine fever virus); and unclassified viruses (e.g., the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astro viruses). Examples of infectious bacteria to which stimulation of a protective immune response is desirable include: *Helicobacter pylons, Borellia burgdorferi, Legionella pneumophilia, Mycobacteria* sps (e.g. *M. tuberculosis, M. avium, M. intracellular* c, *M. kansaii, M. gordonac*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus antracis, Corynebacterium diphtheriae, Corynebacterium* sp., *Erysipelothrix rhusiopathiae, Clostridium perfringers, Clostridium tetani, Enterobacter aerogenes, Klebsiella pneumoniae, Pasteurella multocida, Bacteroides* sp., *Fusobacterium nucleatum, Streptobacillus* monïliformis, *Treponema pallidium, Treponema pertenue, Leptospira*, and *Actinomyces israelli*. Examples of infectious fungi to which stimulation of a protective immune response is desirable include: *Cryptococcus neoformans, Histoplasma capsulatum, Coccidioides immitis, Blastomyces dermatitidis, Chlamydia trachomatis, Candida albicans*. Other infectious organisms (i.e., protists) include: *Plasmodium falciparum* and *Toxoplasma gondii*.

In one aspect, the disclosure provides a method of reducing one or more side-effects of a therapeutic agent in a subject in need thereof. In some embodiments, the method comprises administering to the subject a complex comprising a targeting unit and a therapeutic unit in accordance with any embodiment of the present disclosure, wherein the therapeutic agent in the complex is delivered in an amount that is less than an amount of the same therapeutic agent necessary to achieve a comparable therapeutic effect when administered alone. Decrease in the effective dose can be determined with respect to doses associated with historical treatment outcomes for an individual subject receiving a therapeutic agent alone. Decrease in the effective dose can be determined with respect to two groups of subjects, one group receiving the therapeutic agent alone, and the other receiving the therapeutic agent as part of the complex. In some embodiments, the dose of a therapeutic agent in a complex used to achieve a particular therapeutic result is about or more than about 1.5, 2, 3, 5, 7, or 10-fold or more lower than when used independently to achieve the same or better therapeutic effect. In some embodiments, the dose of a therapeutic agent in a complex used to achieve a particular therapeutic result is about or less than about 90%, 80%, 70%, 60%, 50%, 40%, 30%, 25%, 20%, 15%, or 10% of the dose used to achieve the same result when the therapeutic agent is administered alone.

In one aspect, the disclosure provides a method of inducing death of target cells. In some embodiments, the method comprises administering to the target cells a complex comprising a targeting unit and a therapeutic unit in accordance with any embodiment of the present disclosure, wherein administering the complex to the target cells induces a greater degree of target cell death relative to administering a comparable amount of the therapeutic agent alone. In some embodiments, the complex is administered to the target cells in vivo, such as described herein with respect to other aspects of the disclosure. In some embodiments, the complex is administered to the target cells in vitro, such as described herein with respect to other aspects of the disclosure. A target cell may be any to which a targeting moiety may be directed, such as a cell disclosed herein. In some embodiments, the target cell is a cancer cell. In some embodiments, cell death is induced in about or more than about 10%, 20%, 30%, 40%, 50%, 60%, 70%, 80%, 90%, 95%, 99%, or up to 100% of the target cells in a target cell population. In some embodiments, the desired amount of target cell death in a target cell population is reached by about or less than about 48, 24, 18, 12, 11, 10, 9, 8, 7, 6, 5, 4, 3, 2, or 1 hours. In some embodiments, the ratio of complex to target cells in a cell death assay is about or less than about X to 1, wherein X is 0.5, 1, 2, 3, 4, 5, 6, 7, 8, 9, 10, 15, 20, 25, 50, 75, 100, 150, 200, 250, 500, or more. In some embodiments, the amount of cell death induced by an amount of therapeutic agent administered in a complex is about or more than about 2-fold, 3-fold, 4-fold, 5-fold, 6-fold, 7-fold, 8-fold, 9-fold, 10-fold, 15-fold, 20-fold, 25-fold, 50-fold, 75-fold, 100-fold, 200-fold, 250-fold, 500-fold, 1000-fold, or 10000-fold greater than the amount of cell death induced by the same amount of therapeutic agent when administered alone.

In some embodiments, the method of inducing cell death comprises administering to the target cells a plurality of conjugated cells complexed to exogenous targeting units, in accordance with any embodiment of the present disclosure. In some embodiments, administering the complexed cells to the target cells induces a greater degree of target cell death relative to administering a comparable amount of complexed cells lacking the targeting units. In some embodiments, a complexed cell comprises two or more different exogenous targeting units (e.g. about or more than about 2, 3, 4, 5, 6, 7, 8, 9, 10, 15, 20, or more different exogenous targeting units), such as described herein with respect to other aspects of the disclosure. In some embodiments, the complexed cells are administered to the target cells in vivo, such as described herein with respect to other aspects of the disclosure. In some embodiments, the complexed cells are administered to the target cells in vitro, such as described herein with respect to other aspects of the disclosure. A target cell may be any to which a targeting moiety may be directed, such as a cell disclosed herein. In some embodiments, the target cell is a cancer cell. In some embodiments, cell death is induced in about or more than about 10%, 20%, 30%, 40%, 50%, 60%, 70%, 80%, 90%, 95%, 99%, or up to 100% of the target cells in a target cell population. In some embodiments, the desired amount of target cell death in a target cell population is reached by about or less than about 48, 24, 18, 12, 11, 10, 9, 8, 7, 6, 5, 4, 3, 2, or 1 hours. In some embodiments, the ratio of complexed cells to target cells in a cell death assay is about or less than about X to 1, wherein X is 0.5, 1, 2, 3, 4, 5, 6, 7, 8, 9, 10, 15, 20, 25, 50, 75, 100, 150, 200, 250, 500, or more. In some embodiments, the amount of cell death induced by a number of complexed cells under certain conditions is about or more than about 2-fold, 3-fold, 4-fold, 5-fold, 6-fold, 7-fold, 8-fold, 9-fold, 10-fold, 15-fold, 20-fold, 25-fold, 50-fold, 75-fold, 100-fold, 200-fold, 250-fold, 500-fold, 1000-fold, or 10000-fold greater than the amount of cell death induced by the same number of control cells when administered alone, wherein the control cells are of the same cell type as the complexed cells but are not complexed to a targeting moiety.

Cell death may be determined by any suitable method, including, but not limited to, counting cells before and after treatment, or measuring the level of a marker associated with live or dead cells (e.g. live or dead target cells). Degree of cell death may be determined by any suitable method. In some embodiments, degree of cell death is determined with respect to a starting condition. For example, an individual may have a known starting amount of target cells, such as a starting cell mass of known size or circulating target cells at a known concentration. In such cases, degree of cell death may be expressed as a ratio of surviving cells after treatment to the starting cell population. In some embodiments, degree of cell death may be determined by a suitable cell death assay. A variety of cell death assays are available, and may utilize a variety of detection methodologies. Example of detection methodologies include, without limitation, the use of cell staining, microscopy, flow cytometry, cell sorting, and combinations of these. Further non-limiting examples of cell death assays are described in WO2011131472A1, which is incorporated herein by reference.

Any suitable method may be used to compare degree of cell death induced by one composition with respect to another (e.g. a conjugated therapeutic agent or cell to a corresponding uncomplexed therapeutic agent or cell). For example, relative degree of cell death can be determined with respect to historical treatment outcomes for an individual subject receiving a therapeutic agent alone as compared to the degree of target cell death (e.g. rate of target cell death) following treatment with the therapeutic agent in a complex of any of the disclosed embodiments. As another example, relative degree of cell death can be determined determined with respect to two groups of subjects, one group receiving a therapeutic agent alone, and the other receiving the therapeutic agent as part of a complex in accordance with a disclosed embodiment. As a further example, a population of target cells may be divided into two sub-populations in an in vitro assay, with one subpopulation receiving cells complexed with targeting units as described herein, and another subpopulation being treated with an equivalent amount of cells of the same type as the complexed cells but lacking the targeting units.

In one aspect, the disclosure provides a method of treating cancer. In some embodiments, the method comprises administering to a subject in need thereof a complex comprising a targeting unit and a therapeutic unit in accordance with any embodiment of the present disclosure, wherein (a) the targeting moiety exhibits specific binding to a biological marker on the cancer cell; and (b) the complex induces death of cancer cells. In some embodiments, the method comprises administering to a subject in need thereof conjugated cells complexed to exogenous targeting units, in accordance with any embodiment of the present disclosure, wherein (a) the biological marker is on the cancer cell; and (b) the complexed cell induces death of cancer cells. In some embodiments, a complexed cell comprises two or more different exogenous targeting units (e.g. about or more than about 2, 3, 4, 5, 6, 7, 8, 9, 10, 15, 20, or more different exogenous targeting units), such as described herein with respect to other aspects of the disclosure. Non-limiting examples of cancers that may be treated by the disclosed methods (and cells of which may be targeting by a targeting unit) include Acanthoma, Acinic cell carcinoma, Acoustic neuroma, Acral lentiginous melanoma, Acrospiroma, Acute cosinophilic leukemia, Acute lymphoblastic leukemia, Acute megakaryoblastic leukemia, Acute monocytic leukemia, Acute myeloblastic leukemia with maturation, Acute myeloid dendritic cell leukemia, Acute myeloid leukemia, Acute promyelocytic leukemia, Adamantinoma, Adeno carcinoma, Adenoid cystic carcinoma, Adenoma, Adenomatoid odontogenic tumor, Adrenocortical carcinoma, Adult T-cell leukemia, Aggressive NK-cell leukemia, AIDS-Related Cancers, AIDS-related lymphoma, Alveolar soft part sarcoma, Ameloblastic fibroma, Anal cancer, Anaplastic large cell lymphoma, Anaplastic thyroid cancer, Angioimmunoblastic T-cell lymphoma, Angiomyolipoma, Angiosarcoma, Appendix cancer, Astrocytoma, Atypical teratoid rhabdoid tumor, Basal cell carcinoma, Basal-like carcinoma, B-cell leukemia, B-cell lymphoma, Bellini duct carcinoma, Biliary tract cancer, Bladder cancer, Blastoma, Bone Cancer, Bone tumor, Brain Stem Glioma, Brain Tumor, Breast Cancer, Brenner tumor, Bronchial Tumor, Bronchioloalveolar carcinoma, Brown tumor, Burkitt's lymphoma, Cancer of Unknown Primary Site, Carcinoid Tumor, Carcinoma, Carcinoma in situ, Carcinoma of the penis, Carcinoma of Unknown Primary Site, Carcinosarcoma, Castleman's Disease, Central Nervous System Embryonal Tumor, Cerebellar Astrocytoma, Cerebral Astrocytoma, Cervical Cancer, Cholangiocarcinoma, Chondroma, Chondrosarcoma, Chordoma, Choriocarcinoma, Choroid plexus papilloma, Chronic Lymphocytic Leukemia, Chronic monocytic leukemia, Chronic myelogenous leukemia, Chronic Myeloproliferative Disorder, Chronic neutrophilic leukemia, Clear-cell tumor, Colon Cancer, Colorectal cancer, Craniopharyngioma, Cutaneous T-cell lymphoma, Degos disease, Dermatofibrosarcoma protuberans, Dermoid cyst, Desmoplastic small round cell tumor, Diffuse large B cell lymphoma, Dysembryoplastic neuroepithelial tumor, Embryonal carcinoma, Endodermal sinus tumor, Endometrial cancer, Endometrial Uterine Cancer, Endometrioid tumor, Enteropathy-associated T-cell lymphoma, Ependymoblastoma, Ependymoma, Epithelioid sarcoma, Erythroleukemia, Esophageal cancer, Esthesioneuroblastoma, Ewing Family of Tumor, Ewing Family Sarcoma, Ewing's sarcoma, Extracranial Germ Cell Tumor, Extragonadal Germ Cell Tumor, Extrahepatic Bile Duct Cancer, Extramammary Paget's disease, Fallopian tube cancer, Fetus in fetu, Fibroma, Fibrosarcoma, Follicular lymphoma, Follicular thyroid cancer, Gallbladder Cancer, Gallbladder cancer, Ganglioglioma, Ganglioneuroma, Gastric Cancer, Gastric lymphoma, Gastrointestinal cancer, Gastrointestinal Carcinoid Tumor, Gastrointestinal Stromal Tumor, Gastrointestinal stromal tumor, Germ cell tumor, Germinoma, Gestational choriocarcinoma, Gestational Trophoblastic Tumor, Giant cell tumor of bone, Glioblastoma multiforme, Glioma, Gliomatosis cerebri, *Glomus* tumor, Glucagonoma, Gonadoblastoma, Granulosa cell tumor, Hairy Cell Leukemia, Hairy cell leukemia, Head and Neck Cancer, Head and neck cancer, Heart cancer, Hemangioblastoma, Hemangiopericytoma, Hemangiosarcoma, Hematological malignancy, Hepatocellular carcinoma, Hepatosplenic T-cell lymphoma, Hereditary breast-ovarian cancer syndrome, Hodgkin Lymphoma, Hodgkin's lymphoma, Hypopharyngeal Cancer, Hypothalamic Glioma, Inflammatory breast cancer, Intraocular Melanoma, Tslet cell carcinoma, Islet Cell Tumor, Juvenile myelomonocytic leukemia, Kaposi Sarcoma, Kaposi's sarcoma, Kidney Cancer, Klatskin tumor, Krukenberg tumor, Laryngeal Cancer, Laryngeal cancer, Lentigo maligna melanoma, Leukemia, Leukemia, Lip and Oral Cavity Cancer, Liposarcoma, Lung cancer, Luteoma, Lymphangioma, Lymphangiosarcoma, Lymphoepithelioma, Lymphoid leukemia, Lymphoma, Macroglobulinemia, Malignant Fibrous Histiocytoma, Malignant fibrous histiocytoma, Malignant Fibrous Histiocytoma of Bone, Malignant Glioma, Malignant Mesothelioma, Malignant peripheral nerve sheath tumor, Malignant rhabdoid tumor, Malignant triton tumor, MALT lymphoma, Mantle cell lymphoma, Mast cell leukemia, Mediastinal germ cell tumor, Mediastinal tumor, Medullary thyroid cancer, Medulloblastoma, Medulloblastoma, Medulloepithelioma, Melanoma, Melanoma, Meningioma, Merkel Cell Carcinoma, Mesothelioma, Mesothelioma, Metastatic Squamous Neck Cancer with Occult Primary, Metastatic urothelial carcinoma, Mixed Mullerian tumor, Monocytic leukemia, Mouth Cancer, Mucinous tumor, Multiple Endocrine Neoplasia Syndrome, Multiple Myeloma, Multiple myeloma, Mycosis Fungoides, Mycosis fungoides, Myelodysplastic Disease, Myelodysplastic Syndromes, Myeloid leukemia, Myeloid sarcoma, Myeloproliferative Disease, Myxoma, Nasal Cavity Cancer, Nasopharyngeal Cancer, Nasopharyngeal carcinoma, Neoplasm, Neurinoma, Neuroblastoma, Neuroblastoma, Neurofibroma, Neuroma, Nodular melanoma, Non-Hodgkin Lymphoma, Non-Hodgkin lymphoma, Nonmelanoma Skin Cancer, Non-Small Cell Lung Cancer, Ocular oncology, Oligoastrocytoma, Oligodendroglioma, Oncocytoma, Optic nerve sheath meningioma, Oral Cancer, Oral cancer, Oropharyngeal Cancer, Osteosarcoma, Osteosarcoma, Ovarian Cancer, Ovarian cancer, Ovarian Epithelial Cancer, Ovarian Germ Cell Tumor, Ovarian Low Malignant Potential Tumor, Paget's disease of the breast, Pancoast tumor, Pancreatic Cancer, Pancreatic cancer, Papillary thyroid cancer, Papillomatosis, Paraganglioma, Paranasal Sinus Cancer, Parathyroid Cancer, Penile Cancer, Perivascular epithelioid cell tumor, Pharyngeal Cancer, Pheochromocytoma, Pineal Parenchymal Tumor of Intermediate Differentiation, Pineoblastoma, Pituicytoma, Pituitary adenoma, Pituitary tumor, Plasma Cell Neoplasm, Pleuropulmonary blastoma, Polyembryoma, Precursor T-lymphoblastic lymphoma, Primary central nervous system lymphoma, Primary effusion lymphoma, Primary Hepatocellular Cancer, Primary Liver Cancer, Primary peritoneal cancer, Primitive neuroectodermal tumor, Prostate cancer, Pseudomyxoma peritonei, Rectal Cancer, Renal cell carcinoma, Respiratory Tract Carcinoma Involving the NUT Gene on Chromosome 15, Retinoblastoma, Rhabdomyoma, Rhabdomyosarcoma, Richter's transformation, Sacrococcygeal teratoma, Salivary Gland Cancer, Sarcoma, Schwannomatosis, Sebaceous gland carcinoma, Secondary neoplasm, Seminoma, Serous tumor, Sertoli-Leydig cell tumor, Sex cord-stromal tumor, Sezary Syndrome, Signet ring cell carcinoma, Skin Cancer, Small blue round cell tumor, Small cell carcinoma, Small Cell Lung Cancer, Small cell lymphoma, Small intestine cancer, Soft tissue sarcoma, Somatostatinoma, Soot wart, Spinal Cord Tumor, Spinal tumor, Splenic marginal zone lymphoma, Squamous cell carcinoma, Stomach cancer, Superficial spreading melanoma, Supratentorial Primitive Neuroectodermal Tumor, Surface epithelial-stromal tumor, Synovial sarcoma, T-cell acute lymphoblastic leukemia, T-cell large granular lymphocyte leukemia, T-cell leukemia, T-cell lymphoma, T-cell prolymphocytic leukemia, Teratoma, Terminal lymphatic cancer, Testicular cancer, Thecoma, Throat Cancer, Thymic Carcinoma, Thymoma, Thyroid cancer, Transitional Cell Cancer of Renal Pelvis and Ureter, Transitional cell carcinoma, Urachal cancer, Urethral cancer, Urogenital neoplasm, Uterine sarcoma, Uveal melanoma, Vaginal Cancer, Verner Morrison syndrome, Verrucous carcinoma, Visual Pathway Glioma, Vulvar Cancer, Waldenstrom's macroglobulinemia, Warthin's tumor, Wilms' tumor, and combinations thereof. In some embodiments, the targeted cancer cell represents a subpopulation within a cancer cell population, such as a cancer stem cell. In some embodiments, the cancer is of a hematopoietic lineage, such as a lymphoma.

In some embodiments, therapeutic efficacy is measured based on an effect of treating a proliferative disorder, such as cancer. In general, therapeutic efficacy of the methods and compositions of the disclosure, with regard to the treatment of a proliferative disorder (e.g. cancer, whether benign or malignant), may be measured by the degree to which the methods and compositions promote inhibition of tumor cell proliferation, the inhibition of tumor vascularization, the death of tumor cells, and/or a reduction in the size of at least one tumor such that a human is treated for the proliferative disorder. Several parameters to be considered in the determination of therapeutic efficacy are discussed herein. The proper combination of parameters for a particular situation can be established by the clinician. Progress in treating cancer (e.g., reducing tumor size or killing cancerous cells) can be ascertained using any suitable method, such as those methods currently used in the clinic to track tumor size and cancer progress. In some embodiments, the efficacy parameter used to evaluate the treatment of cancer is a reduction in the size of a tumor. Tumor size can be determined using any suitable technique, such as measurement of dimensions, or estimation of tumor volume using available computer software, such as FreeFlight software developed at Wake Forest University that enables accurate estimation of tumor volume. Tumor size can be determined by tumor visualization using, for example, CT, ultrasound, SPECT, spiral CT, MRI, photographs, and the like. In embodiments where a tumor is surgically resected after completion of the therapeutic period, the presence of tumor tissue and tumor size can be determined by gross analysis of the tissue to be resected, and/or by pathological analysis of the resected tissue.

In some embodiments, the growth of a tumor is stabilized (e.g., one or more tumors do not increase more than 1%, 5%, 10%, 15%, or 20% in size, and/or do not metastasize) as a result of treatment. In some embodiments, a tumor is stabilized for at least about 1, 2, 3, 4, 5, 6, 7, 8, 9, 10, 11, 12, or more weeks. In some embodiments, a tumor is stabilized for at least about 1, 2, 3, 4, 5, 6, 7, 8, 9, 10, 11, 12, or more months. In some embodiments, a tumor is stabilized for at least about 1, 2, 3, 4, 5, 6, 7, 8, 9, 10, or more years. In some embodiments, the size of a tumor or the number of tumor cells is reduced by at least about 5%, 10%, 15%, 20%, 25, 30%, 35%, 40%, 45%, 50%, 55%, 60%, 65%, 70%, 75%, 80%, 85%, 90%, 95%, or more. In some embodiments, the tumor is completely eliminated, or reduced below a level of detection. In some embodiments, a subject remains tumor free (e.g. in remission) for at least about 1, 2, 3, 4, 5, 6, 7, 8, 9, 10, 11, 12, or more weeks following treatment. In some embodiments, a subject remains tumor free for at least about 1, 2, 3, 4, 5, 6, 7, 8, 9, 10, 11, 12, or more months following treatment. In some embodiments, a subject remains tumor free for at least about 1, 2, 3, 4, 5, 6, 7, 8, 9, 10, or more years after treatment.

When a tumor is subject to surgical resection following completion of a therapeutic period, the efficacy of treatment in reducing tumor size can be determined by measuring the percentage of resected tissue that is necrotic (i.e., dead). In some embodiments, a treatment is therapeutically effective if the necrosis percentage of the resected tissue is greater than about 20% (e.g., at least about 30%, 40%, 50%, 60%, 70%, 80%, 90%, or 100%), or greater than about 90% or greater (e.g., about 90%, 95%, or 100%). In some embodiments, the necrosis percentage of the resected tissue is 100%, that is, no living tumor tissue is present or detectable.

A number of secondary parameters can be employed to determine efficacy. Examples of secondary parameters include, but are not limited to, detection of new tumors, detection of tumor antigens or markers (e.g., CEA, PSA, or CA-125), biopsy, surgical downstaging (i.e., conversion of the surgical stage of a tumor from unresectable to resectable), PET scans, survival, disease progression-free survival, time to disease progression, quality of life assessments such as the Clinical Benefit Response Assessment, and the like, all of which can point to the overall progression (or regression) of cancer in a human. Biopsy is particularly useful in detecting the eradication of cancerous cells within a tissue. Radioimmunodetection (RAID) is used to locate and stage tumors using serum levels of markers (antigens) produced by and/or associated with tumors ("tumor markers" or "tumor-associated antigens"), and can be useful as a pre-treatment diagnostic predicate, a post-treatment diagnostic indicator of recurrence, and a post-treatment indicator of therapeutic efficacy. Examples of tumor markers or tumor-associated antigens that can be evaluated as indicators of therapeutic efficacy include, but are not limited to, carcinembryonic antigen (CEA) prostate-specific antigen (PSA), CA-125, CA19-9, ganglioside molecules (e.g., GM2, GD2, and GD3), MART-1, heat shock proteins (e.g., gp96), sialyl Tn (STn), tyrosinase, MUC-1, HER-2/neu, c-erb-B2, KSA, PSMA, p53, RAS, EGF-R, VEGF, MAGE, and gp100. Other tumor-associated antigens are known in the art. RAID technology in combination with endoscopic detection systems also efficiently distinguishes small tumors from surrounding tissue (see, for example, U.S. Pat. No. 4,932,412).

In some embodiments, the treatment of cancer in a human patient is evidenced by one or more of the following results: (a) the complete disappearance of a tumor or circulating cancer cells (i.e., a complete response), (b) about a 25% to about a 50% reduction in the size of a tumor or number of circulating cancer cells for at least four weeks after completion of the therapeutic period as compared to measurement before treatment, (c) at least about a 50% reduction in the size of a tumor or number of circulating cancer cells for at least four weeks after completion of the therapeutic period as compared to measurement before the therapeutic period, and (d) at least a 2% decrease (e.g., about a 5%, 10%, 20%, 30%, 40%, 50%, 60%, 70%, 80% or 90% decrease) in a specific cancer-associated antigen level at about 4-12 weeks after completion of the therapeutic period as compared to the cancer-associated antigen level before the therapeutic period. While at least a 2% decrease in a cancer-associated antigen level is preferred, any decrease in the cancer-associated antigen level is evidence of treatment of a cancer in a patient by a method of the disclosure. For example, with respect to unresectable, locally advanced pancreatic cancer, treatment can be evidenced by at least a 10% decrease in the CA19-9 tumor-associated antigen level at 4-12 weeks after completion of the therapeutic period as compared to the CA19-9 level before the therapeutic period. Similarly, with respect to locally advanced rectal cancer, treatment can be evidenced by at least a 10% decrease in the CEA tumor-associated antigen level at 4-12 weeks after completion of the therapeutic period as compared to the CEA level before the therapeutic period.

With respect to quality of life assessments, such as the Clinical Benefit Response Criteria, the therapeutic benefit of the treatment in accordance with some embodiments can be evidenced in terms of pain intensity, analgesic consumption, and/or the Karnofsky Performance Scale score. The Karnofsky Performance Scale allows patients to be classified according to their functional impairment. The Karnofsky Performance Scale is scored from 0-100. In general, a lower Karnofsky score is predictive of a poor prognosis for survival. Thus, the treatment of cancer in a human patient alternatively, or in addition, is evidenced by (a) at least a 50% decrease (e.g., at least a 60%, 70%, 80%, 90%, or 100% decrease) in pain intensity reported by a patient, such as for any consecutive four week period in the 12 weeks after completion of treatment, as compared to the pain intensity reported by the patient before treatment, (b) at least a 50% decrease (e.g., at least a 60%, 70%, 80%, 90%, or 100% decrease) in analgesic consumption reported by a patient, such as for any consecutive four week period in the 12 weeks after completion of treatment as compared to the analgesic consumption reported by the patient before treatment, and/or (c) at least a 20 point increase (e.g., at least a 30 point, 50 point, 70 point, or 90 point increase) in the Karnofsky Performance Scale score reported by a patient, such as for any consecutive four week period in the 12 weeks after completion of the therapeutic period as compared to the Karnofsky Performance Scale score reported by the patient before the therapeutic period.

The treatment of a proliferative disorder (e.g. cancer, whether benign or malignant) in a human patient desirably is evidenced by one or more (in any combination) of the foregoing results, although alternative or additional results of the referenced tests and/or other tests can evidence treatment efficacy.

In some embodiments, tumor size is reduced as a result of treatment in accordance with a method of the disclosure without significant adverse events in the subject. Adverse events are categorized or "graded" by the Cancer Therapy Evaluation Program (CTEP) of the National Cancer Institute (NCI), with Grade 0 representing minimal adverse side effects and Grade 4 representing the most severe adverse events. The NCI toxicity scale (published April 1999) and Common Toxicity Criteria Manual (updated August 1999) is available through the NCI, e.g., through the NCI internet website at www.ctep.info.nih.gov or in the Investigator's Handbook for participants in clinical trials of investigational agents sponsored by the Division of Cancer Treatment and Diagnosis, NCI (updated March 1998). In some embodiments, treatment is associated with minimal adverse events, e.g. Grade 0, Grade 1, or Grade 2 adverse events, as graded by the CTEP/NCI. However, as discussed herein, reduction of tumor size, although preferred, is not required in that the actual size of tumor may not shrink despite the eradication of tumor cells. Eradication of cancerous cells is sufficient to realize a therapeutic effect. Likewise, any reduction in tumor size is sufficient to realize a therapeutic effect.

Detection, monitoring, and rating of various cancers in a human are further described in Cancer Facts and Figures 2001, American Cancer Society, New York, N.Y., and International Patent Application WO2001024684. Accordingly, a clinician can use standard tests to determine the efficacy of cancer treatment. However, in addition to tumor size and spread, the clinician also may consider quality of life and survival of the patient in evaluating efficacy of treatment.

Improved efficacy may be measured using any method known in the art, including but not limited to those described herein. In some embodiments, the improved therapeutic efficacy is an improvement of at least about 10%, 20%, 30%, 40%, 50%, 60%, 70%, 75%, 80%, 90%, 95%, 100%, 110%, 120%, 150%, 200%, 300%, 400%, 500%, 600%, 700%, 1000%, 10000% or more, using an appropriate measure (e.g. tumor size reduction, duration of tumor size stability, duration of time free from metastatic events, duration of disease-free survival). Improved efficacy may also be expressed as fold improvement, such as at least about 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 1000-fold, 10000-fold, or more, using an appropriate measure (e.g. tumor size reduction, duration of tumor size stability, duration of time free from metastatic events, duration of disease-free survival).

In one aspect, the disclosure provides a method for inducing cell proliferation in a target tissue. In some embodiments, the method comprises administering to a subject in need thereof a complex comprising a targeting unit and a therapeutic unit in accordance with any embodiment of the present disclosure, wherein (a) the complex is delivered to the target tissue via the targeting moiety specifically binding to a biological marker; and (b) the therapeutic agent induces cell proliferation in the target tissue. In some embodiments, the method comprises administering to a subject in need thereof conjugated cells complexed to exogenous targeting units, in accordance with any embodiment of the present disclosure, wherein (a) the cell is delivered to the target tissue via the targeting moiety specifically binding to the biological marker; and (b) the complexed cell proliferates in the target tissue. In some embodiments, a complexed cell comprises two or more different exogenous targeting units (e.g. about or more than about 2, 3, 4, 5, 6, 7, 8, 9, 10, 15, 20, or more different exogenous targeting units), such as described herein with respect to other aspects of the disclosure. A complex may be directed to a target tissue as a result of the targeting moiety having an affinity for a target cell in the tissue, such as a target cell as described herein. In some embodiments, the therapeutic agent is a growth factor that stimulates proliferation or differentiation of a target cell of interest having a cell surface receptor to which the growth factor binds. Non-limiting examples of growth factors include granulocyte macrophage-colony stimulating factor (GM-CSF), granulocyte-colony stimulating factor (G-CSF), macrophage-colony stimulating factor (M-CSF), tumor necrosis factor (TNF-α), insulin-like growth factor (IGF), transforming growth factor-β (TGF-β), nerve growth factor (NGF), epidermal growth factor (EGF), stem cell factor (SCF), platelet-derived growth factor (PDGF), fibroblast growth factors (FGF), interleukin-1, interleukin-2, keratinocyte growth factor, ciliary neurotrophic growth factor, insulin, Schwann cell-derived growth factor, vaccinia virus growth factor, bombyxin, neu differentiation factor, v-Sis, glial growth factor/acetylcholine receptor-inducing activity and other proteins belonging to their structural superfamilies. In some embodiments, the conjugated cell is a progenitor cell that, upon delivery to the target tissue, proliferates and differentiates to repair, regenerate, or reconstruct the target tissue. In some embodiments, the progenitor cell is a stem cell, such as a stem cell as disclosed herein.

In some embodiments, administering the complex forms part of a therapy. The therapy may be regenerative therapy requiring tissue replacement, regeneration or repair. The therapy may be for a neurological disease, disorder or deficit. The therapy may improve functional and/or cognitive recovery. The therapy may be of stroke, peripheral arterial disease, neuropathy or any other disease or disorder that requires tissue regeneration, revascularisation, or local anti-inflammatory action, including but not limited to, neurological disorder, disease or deficit, such as Parkinson's disease, Alzheimer's disease, stroke, or ALS; lysosomal storage disorders; cardiovascular disorders, such as myocardial infarction, congestive heart failure, peripheral arterial disease, diabetic ulcers, wound healing; diseases of the lung, including idiopathic pulmonary fibrosis, respiratory distress syndrome, chronic obstructive pulmonary disease, idiopathic pulmonary hypertension, cystic fibrosis and asthma; metabolic or inflammatory disorders, such as diabetes (i or ii), rheumatoid arthritis, osteoarthritis, lupus, crohn's disease, inflammatory bowel disease, or graft versus host disease; blindness-causing diseases of the retina, such as age-related macular degeneration, Stargardt disease, diabetic retinopathy, retinitis pigmentosa; and demyelinating diseases, such as multiple sclerosis, cerebral palsy, central pontine myelinolysis, tabes *dorsalis*, transverse myelitis, Devic's disease, progressive multifocal leukoencephalopathy, optic neuritis, leukodystrophies, Guillain-Barre syndrome, anti-MAG peripheral neuropathy and Charcot-Marie-tooth disease.

Tn one aspect, the disclosure provides a method of growing stem cells in solution. Tn some embodiments, the method comprises (a) combining a first population of cells that are live conjugated cells complexed to exogenous targeting units, in accordance with any embodiment of the present disclosure, and a second population of cells, wherein (i) one of the first and second populations is a population of stem cells; (ii) the other of the first and second populations is a population of feeder cells; and (iii) the biological marker is a marker on the surface of cells in the second population; and (b) growing the stem cells as non-adherent cells free in solution, associated with the feeder cells via the targeting units. In some embodiments, the first population of cells are stem cells and the second population of cells are feeder cells. In some embodiments, the first population of cells are feeder cells, and the second population of cells are stem cells. Cells may be grown under any suitable conditions suspended in a suitable medium. In some embodiments, the medium is periodically or continuously stirred to maintain the cells in suspension. In general, feeder cells promote the growth and maintenance of stem cells. Physical interaction between feeder cells is believed to contribute to this effect. Previous systems relied on the use of adherent feeder cells, which limits efficiency of cell growth by restricting such growth to a two-dimensional surface. Interaction between free cells in solution can be promoted by the formation of complexes in accordance with other aspects of the disclosure.

In some embodiments, the complexed cell is a stem cell, and the targeting moiety has affinity for a cell surface marker associated with a feeder cell. In some embodiments, the complexed cell is a feeder cell and the targeting moiety has affinity for a stem cell. Combining the two populations of cells (complexed cells and target cells) in a suitable medium may be used to promote interaction and cell growth free in solution. The stem cells may be any suitable stem cell, such as those described herein. A feeder cell may be selected based on suitability for use in combination with a particular type of stem cell. Examples of feeder cells include, but are not limited to, primary mouse embryonic fibroblasts (PMEF), mouse embryonic fibroblasts (MEF), murine fetal fibroblasts (MFF), human embryonic fibroblasts (HEF), human fetal muscle cells (HFM), human fetal skin cells (HFS), human adult skin cells, human foreskin fibroblasts (HFF), human adult fallopian tubal epithelial cells (HAFT) and human marrow stromal cells (hMSCs). A variety of media for culturing stem cells are available, such as DMEM (high or low glucose), Eagle's basal medium, Ham's F10 medium (F10), Ham's F-12 medium (F12), Iscove's modified Dulbecco's medium, Mesenchymal Stem Cell Growth Medium (MSCGM), Liebovitz's L-15 medium, MCDB, DMEM/F12, RPMI 1640, advanced DMEM (Gibco), DMEM/MCDB201 (Sigma), and CELL-GRO FREE. Media can be supplemented with additional factors known in the art, such as serum (e.g. 10% or 15% fetal calf serum), growth factors (e.g. PDGF and/or EGF), and antibiotics (e.g. one or more of penicillin, streptomycin, and gentamicin). Cultures can be maintained under conditions suitable for cell survival and growth. Example conditions include 37° C. and 5% $CO_2$.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1: Conjugation of DNA to a Cell without a Cell Wall Via a Lysine Native Functional Group FIG. 1 illustrates an example protocol for conjugating a DNA linker to the surface of a cell. First, a synthetic, single-stranded polynucleotide linker (linker1) having a 5'-thiol was modified to place a coupling group at the 5' end. NHS-$PEO_6$-Maleimide (succinimidyl-[(N-maleimidopropionamido)-hexaethyleneglycol] ester) was purchased from Pierce. A stock solution was prepared by dissolving 5 mg of NHS-$PEO_6$-maleimide (NHS-PEO-Mal) in 1 mL of DMSO (Sigma). DNA modification was achieved by passing a thawed solution of 5'-thiol ssDNA (30 µL, 0.39 mM) through a NAP-5 size-exclusion column (GE Healthcare). The eluent was then exposed to 20 µL of the NHS-$PEO_6$-Maleimide solution at room temperature for 10 minutes. The reaction was then purified by passing it through a second NAP-5 column that was pre-equilibrated with PBS solution (pH 7.2). The concentration of DNA in the column eluent was verified using UV-vis spectroscopy. The resulting solution was then applied to samples of live cells. To confirm the nature of the modification chemistry, models of the oligonucleotide conjugates were prepared and characterized. To do this, 0.5 mL of DMF was saturated with 6-amino-N-(4-aminophenethyl) hexanamide and added to 1 mL of the reaction solution obtained after NAP-5 purification. After 30 min of incubation at room temperature, the oligonucleotide conjugates were analyzed using MALDI-TOF MS. Observed masses were within 0.090% of expected values.

Figure 2:
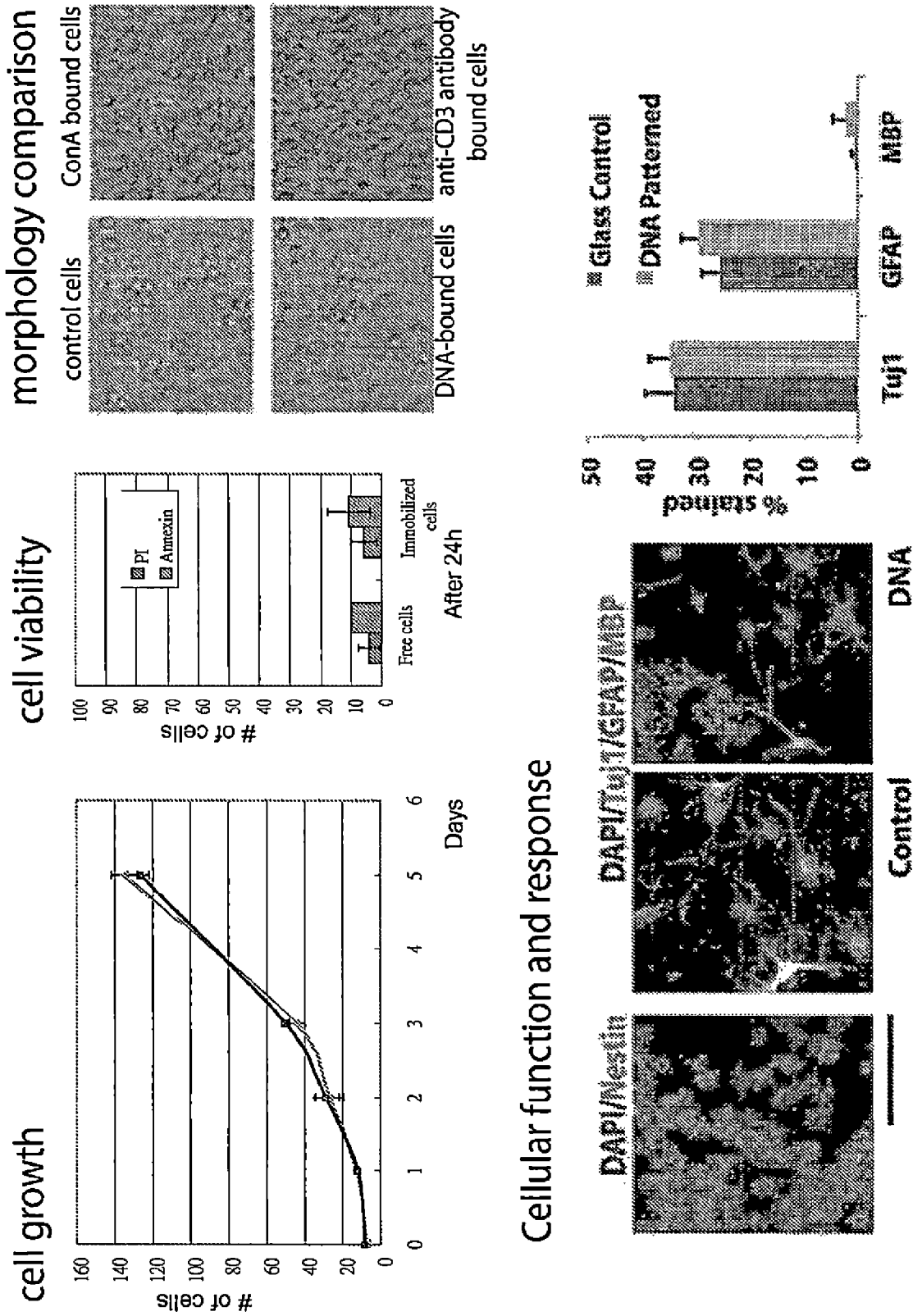
FIG. 2 illustrates the results of various analyses comparing conjugated cells to unconjugated cells. In the "cell viability" bar graph, bars from left to right in each pair correspond to groups listed in the legend from top to bottom, respectively. In the bar graph showing percent staining, bars from left to right in each pair correspond to groups listed in the legend from top to bottom, respectively.

The coupling-group-containing linker1 polynucleotides were combined with live T-cells harvested from mouse lymphnodes, in phosphate buffer at room temperature for less than 30 minutes. The resulting cells were thus conjugated to about $10^6$ linker1 molecules per cell. Linker conjugation was validated by growing the conjugated cells on a surface coated in a defined pattern with DNA complementary linker1. As shown in FIG. 1, cells remained viable but were restricted to the region coated with complementary DNA. Functionality of conjugated cells was assessed by measuring production of various cytokines. As show in the bar graph in FIG. 1, there was no significant difference in cytokine production levels between DNA-bound cells and free cells. These results indicate that conjugation did not produce any undesired activation of intracellular pathways. Functionality of conjugated cells was also assessed along other dimensions by comparing conjugated cells to unconjugated cells, the results of which are shown in FIG. 2. Cell growth rate over 5 days (Jurkat T lymphocytes), cell viability after 24 hours (by PI and Annexin-IV assays on bound and unbound cells), morphology, and cellular function response as measure by DAPI/Tuj1/GFAP/MBP staining was similar between conjugated and non-conjugated cells. Free and DNA-bound primary mouse T cells also showed identical drug response patterns to concanavalin A, phorbol myristate acetate, and cyclosporin A.

Figure 9:
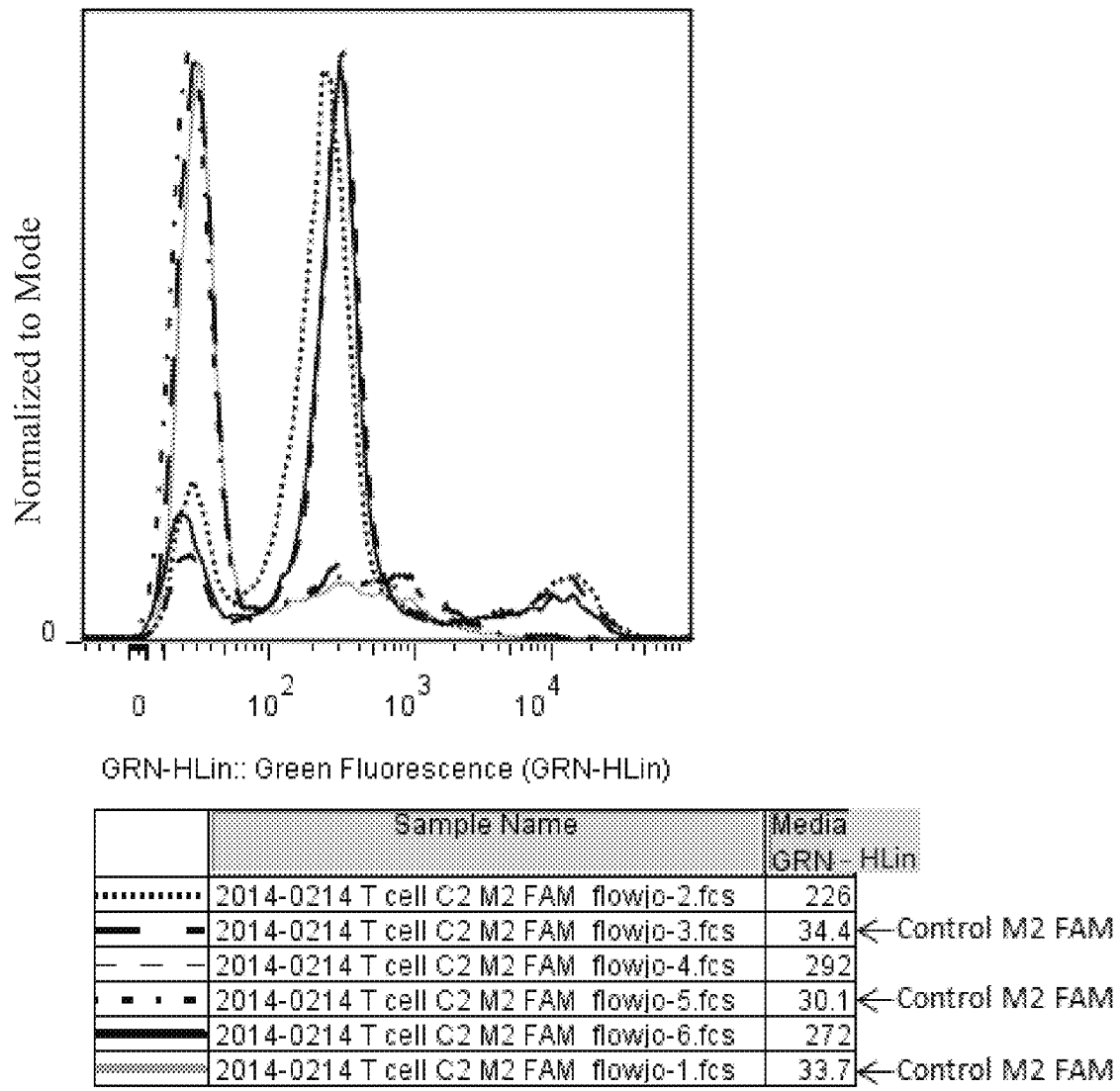
FIG. 9 shows results of flow cytometry analysis quantifying DNA to cell-surface conjugation. The y-axis of the plot is shown normalized to mode. 100 μM C2 DNA was linked to 5 million gd T cells, then reacted with M2 FAM on ice shaking for 30 minutes. The two highest groups of peaks correspond to the control cells (left peaks) and complexed cells (right peaks). The results show the successful conjugation of DNA duplex onto T cell membrane.

In a separate conjugation experiment, the amount of DNA conjugated to a cell surface was quantified by flow cytometry. Cells were combined with a FAM labeled oligonucleotide that included a single-stranded portion complementary to linker1 (linker; "M2 FAM"), or as a control lacked such complementary region ("Control M2 FAM"). After reacting with the labeled oligonucleotides, fluorescence of individual cells was measured by flow cytometry. As shown in FIG. 9 by the shift in population density at higher fluorescent levels in cells combined with linker2 relative to conjugated cells combined with the control DNA sequence, linker1 was conjugated to T cells. The number of linker1 per cell was quantified using FITC-5 MESF beads (Bangs Laboratories, Inc.).

Example 2: Conjugation of DNA to an Antibody

Figure 8:
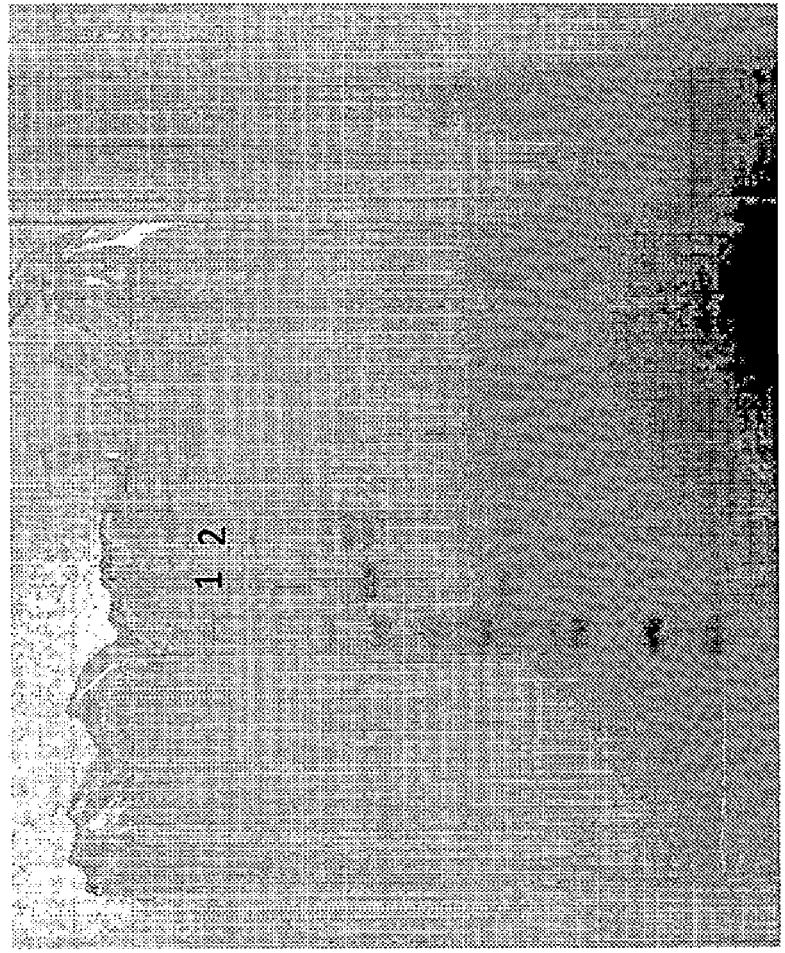
FIG. 8 shows a PAGE gel illustrating size shift of antibody fragments following conjugation to a linker polynucleotide.

A biosimilar of the Rituxan antibody was obtained from Eureka, and was diluted to 5 mg/mL in phosphate buffered saline (PBS). A single-stranded DNA linker (linker2) having a coupling-group at the 5' end was prepared as in Example 1. Linker2 was complementary to linker1. Linker2 was then combined with the antibody at a ratio of about 30 to 1 of linker2 to antibody, in a total volume of about 200 µL, and incubated for about 1.5 hours at room temperature (e.g. about 18-23° C.). Conjugation was confirmed by running an aliquot of the product on a polyacrylamide gel. The results of PAGE analysis are illustrated in FIG. 8. The far left lane is a size ladder. Lane 1 is unconjugated Rituxan antibody, and lane 2 contains conjugated antibody. The fastest-running band in lane 2 corresponds to unconjugated light chain, with a faint band above that corresponding to singly-conjugated light chain. Above that is a triplet of bands corresponding to unconjugated heavy-chain, and singly- and doubly-conjugated heavy chain. The gel confirms that over 75% of treated antibody has at least a singly-conjugated heavy chain.

Example 3: Forming Complexes Between Conjugated Cells and Conjugated Antibodies

In order to direct T-cells to interact with a targeted cell, T-cells conjugated to linker1 (as in Example 1) were combined with antibodies conjugated to linker2 (as in Example 2). 5 million gamma-delta T-cells were conjugated as in Example 1, washed twice with 5 mL PBS, and reacted with 200 μL of conjugated Rituxan antibody conjugated as in Example 2. After 15 minutes shaking, the treated cells were washed twice with 5 mL PBS, pelleted, and resuspended in 100 μL PBS. Resulting T-cells complexed with antibody are alternatively referred to as "armed" T cells.

Figure 10:
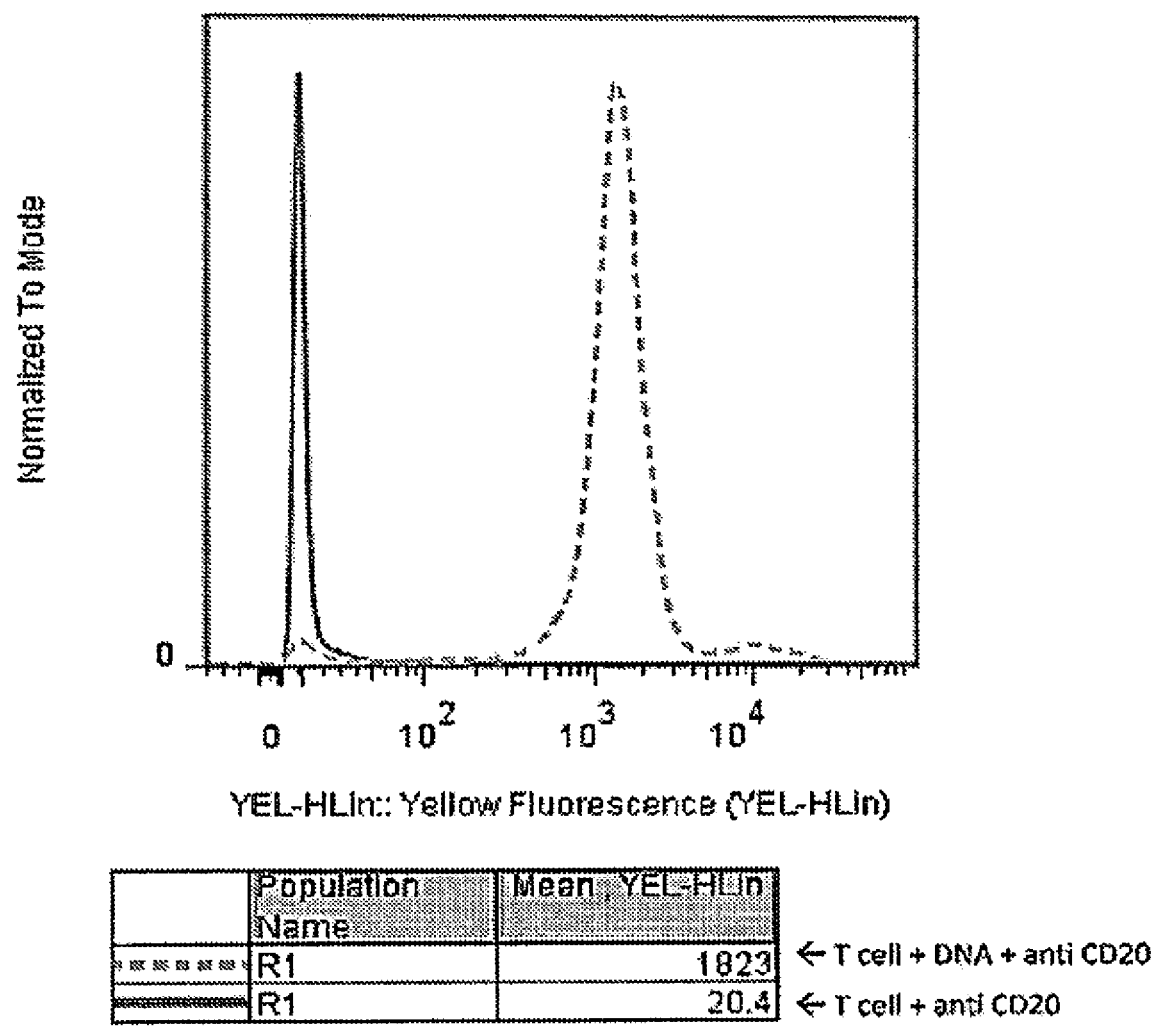
FIG. 10 shows results of flow cytometry analysis quantifying antibody complexed to cell surfaces. The dashed line corresponds to cells conjugated to antibody by way of a linker.
Figure 11:
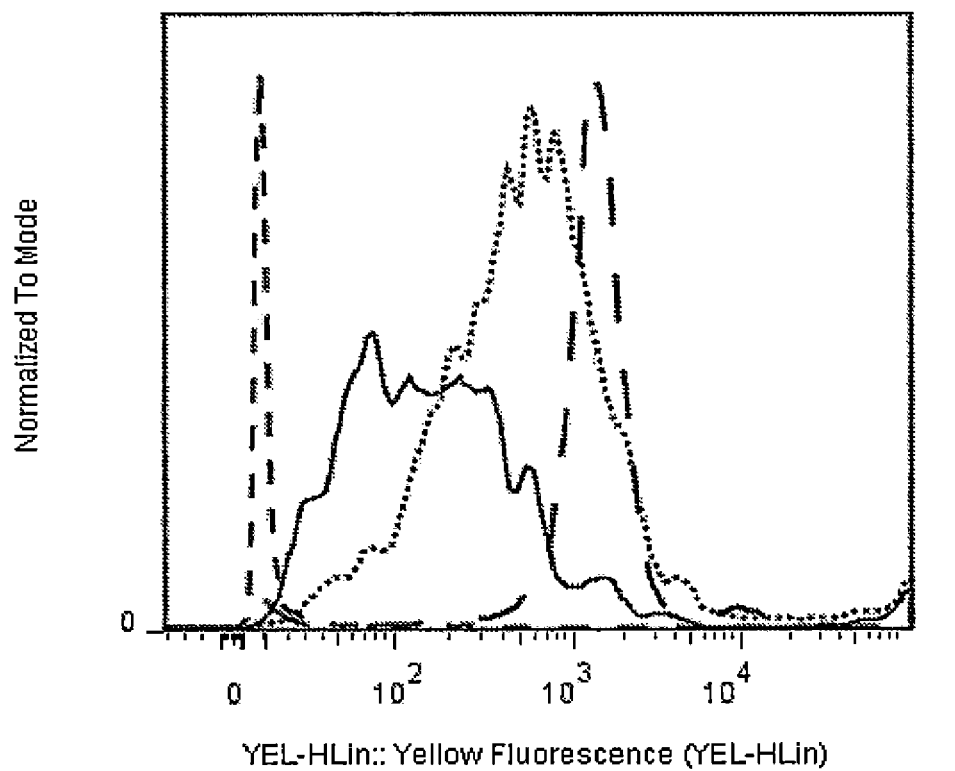
FIG. 11 shows results of flow cytometry analysis quantifying cell surface antibody half-life. The first peak for each line from left to right in the plot correspond to rows 3, 4, 5, and 1 of the accompanying table, respectively.

FIG. 10 illustrates the results of quantifying T-cell surface antibody complexed by this process. 100 μM of linker1 DNA ("C2 DNA") was linked to 15 million gd T cells, which were then combined with Rituxan conjugated with linker2 DNA (M2-Rituxan) and shaken for 15 minutes. The mixture was then reacted with Anti-FAB2-PE in the dark, shaking for 10 minutes. Unmodified gd T cells were treated with Rituxan followed by Anti-FAB2-PE as a control. An anti-FAB2-PE antibody was used to detect the presence of antibody on cells run through a flow cytometer. As illustrated by the flow cytometry results, Rituxan was successfully complexed with the gd T cells by this process. This procedure was repeated, with measurements taken at 0, 48, and 96 hours to monitor half-life of Rituxan at the cell surface. Results are illustrated in FIG. 11. The results indicate that the cell-surface half-life of the antibodies in this particular experiment was about 2 days. The number of Rituxan per cell was quantified using Quantum Simply Cellular beads (Bangs Laboratories, Inc.).

Figure 17:
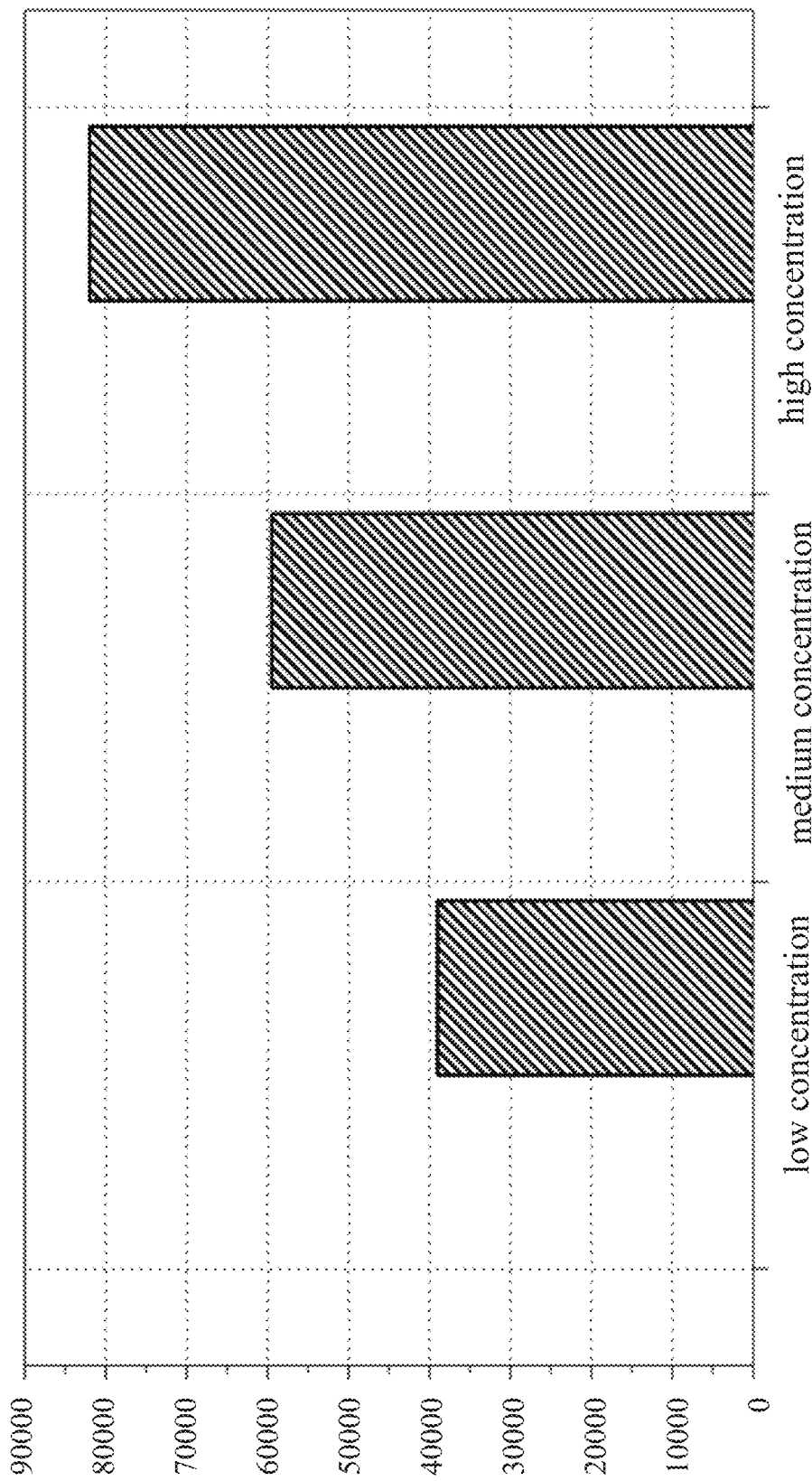
FIG. 17 is a graph showing control over antibody loading.

Complexes were similarly formed between T-cells and increasing concentrations of conjugated Rituxan antibodies, with the result that higher concentrations resulted in an increase in complexes per cell, as illustrated in FIG. 17 (Rituxan antibodies on the cell surface were detected using an anti-Fab2-PE antibody).

Figure 3:
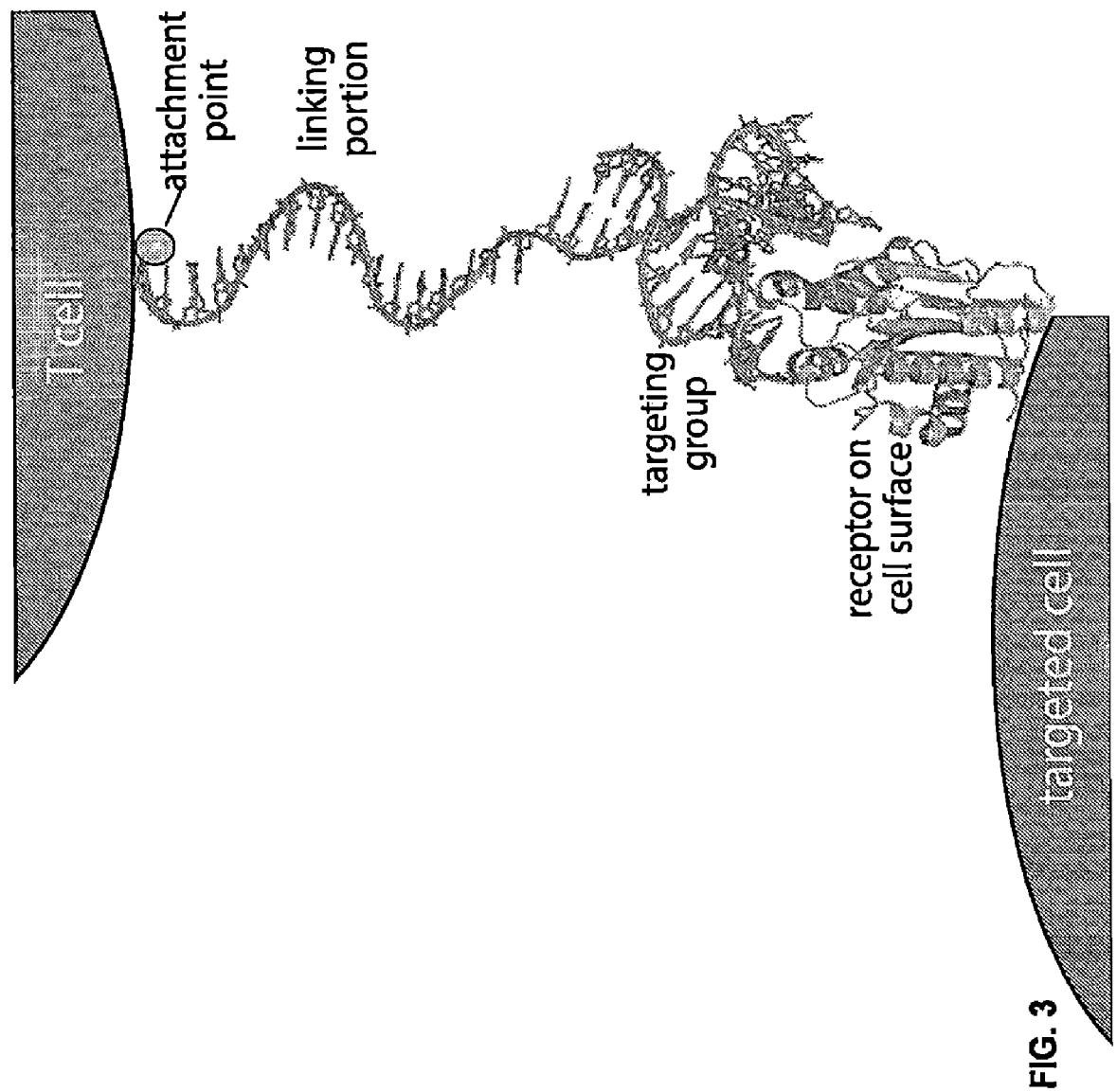
FIG. 3 illustrates a non-limiting example of an interaction between a complexed cell and a target cell, in according with an embodiment.
Figure 4:
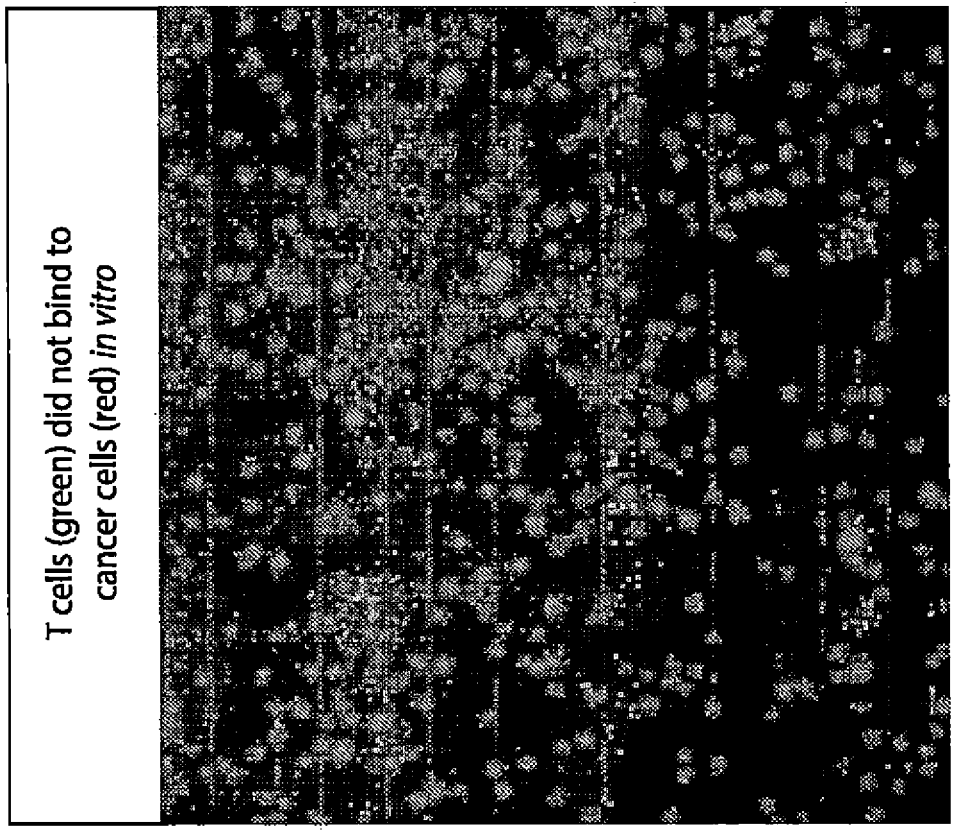
FIG. 4 shows a relative lack of interaction between unconjugated T cells and target cells.
Figure 4:
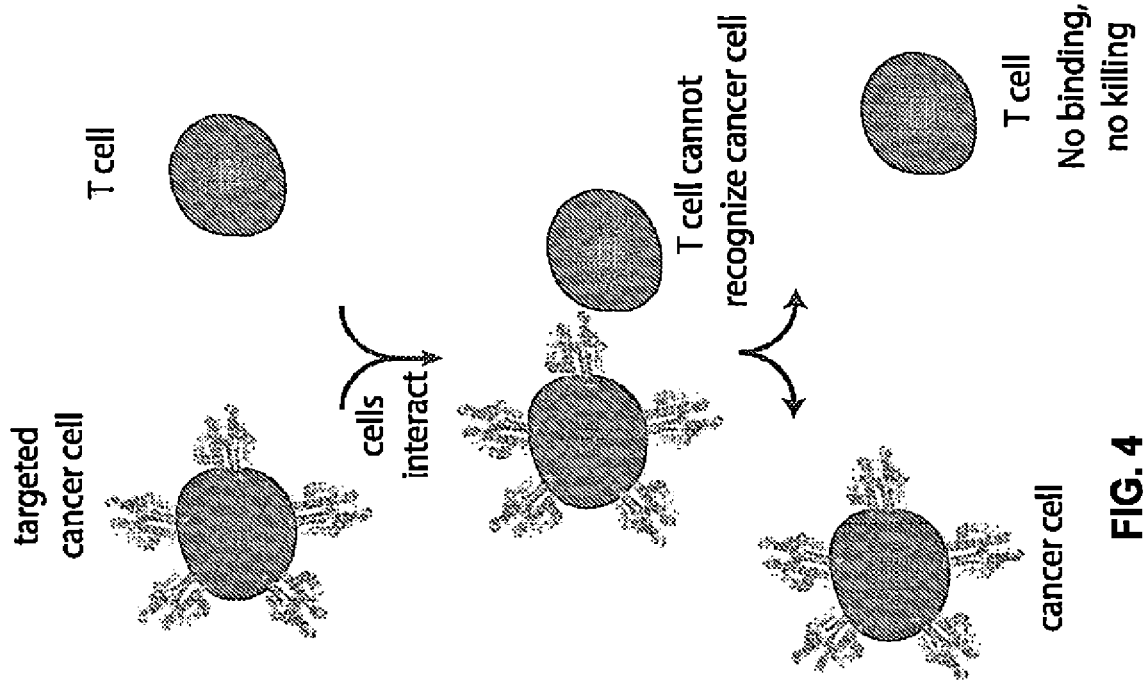
Figure 5:
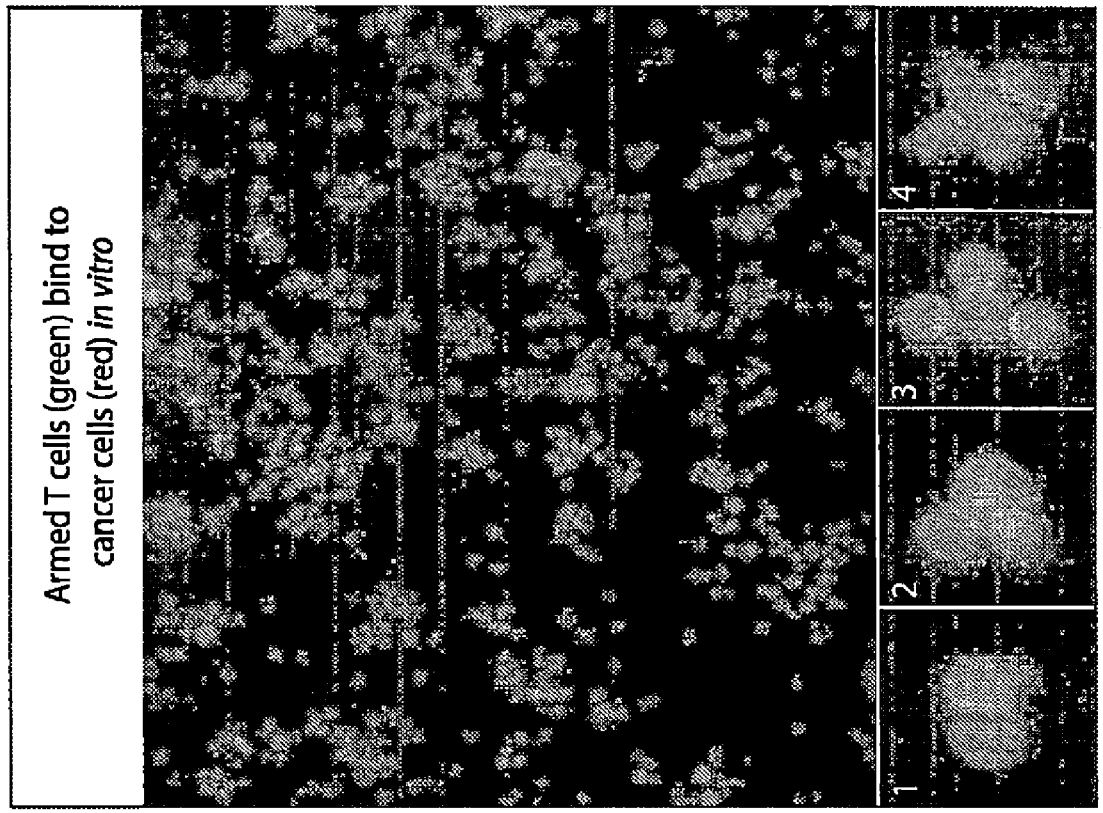
FIG. 5 illustrates a non-limiting possible mechanism for inducing cell death in target cells according to an embodiment, and microscopy images showing interaction of complexed cells with target cells. In the original color images of panels labeled 1 through 4, the large central circle was red, and the small circles overlapping the perimeter were green.
Figure 5:
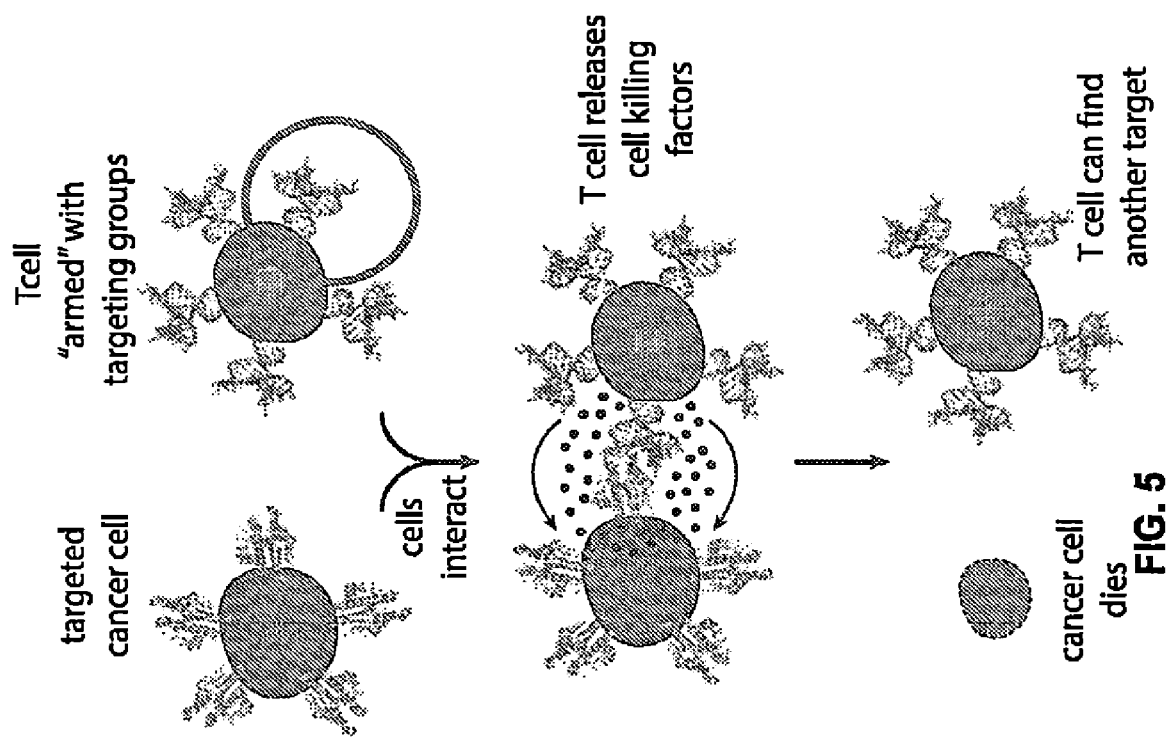

Example 4: Aptamer-Armed T-Cells Induce Interaction with and Death of Target Cells T-cells were conjugated with linker1 as in Example 1. Conjugated T cells were mixed with an aptamer comprising linker2 at one end. In one experiment, U266 cells (a B lymphocyte line) were modified by conjugation with linker1 and combined with an aptamer comprising linker2, which aptamer recognized tyrosine kinase 7 (PTK7), expressed on the surface of Jurkat T cells. Unmodified U266 cells were used as a control. U266 cells were labeled with CytoTracker Red dye to distinguish them in microscopy photos. Labeled U266 cells were incubated with Jurkat cells labeled with CytoTracker Green dye, then visualized after a fixed time (e.g. 2 hours). An illustration of how a complexed cell may interact with a target cell under these conditions is provided in FIG. 3. FIG. 4 shows that uncomplexed U266 cells did not appreciably interact with target Jurkat cells. However, as shown in FIG. 5, conjugated U266 cells did bind to target Jurkat cells. Without wishing to be bound by theory, FIG. 5 also illustrates one possible mechanism for how this interaction may lead to cell killing.

Figure 6:
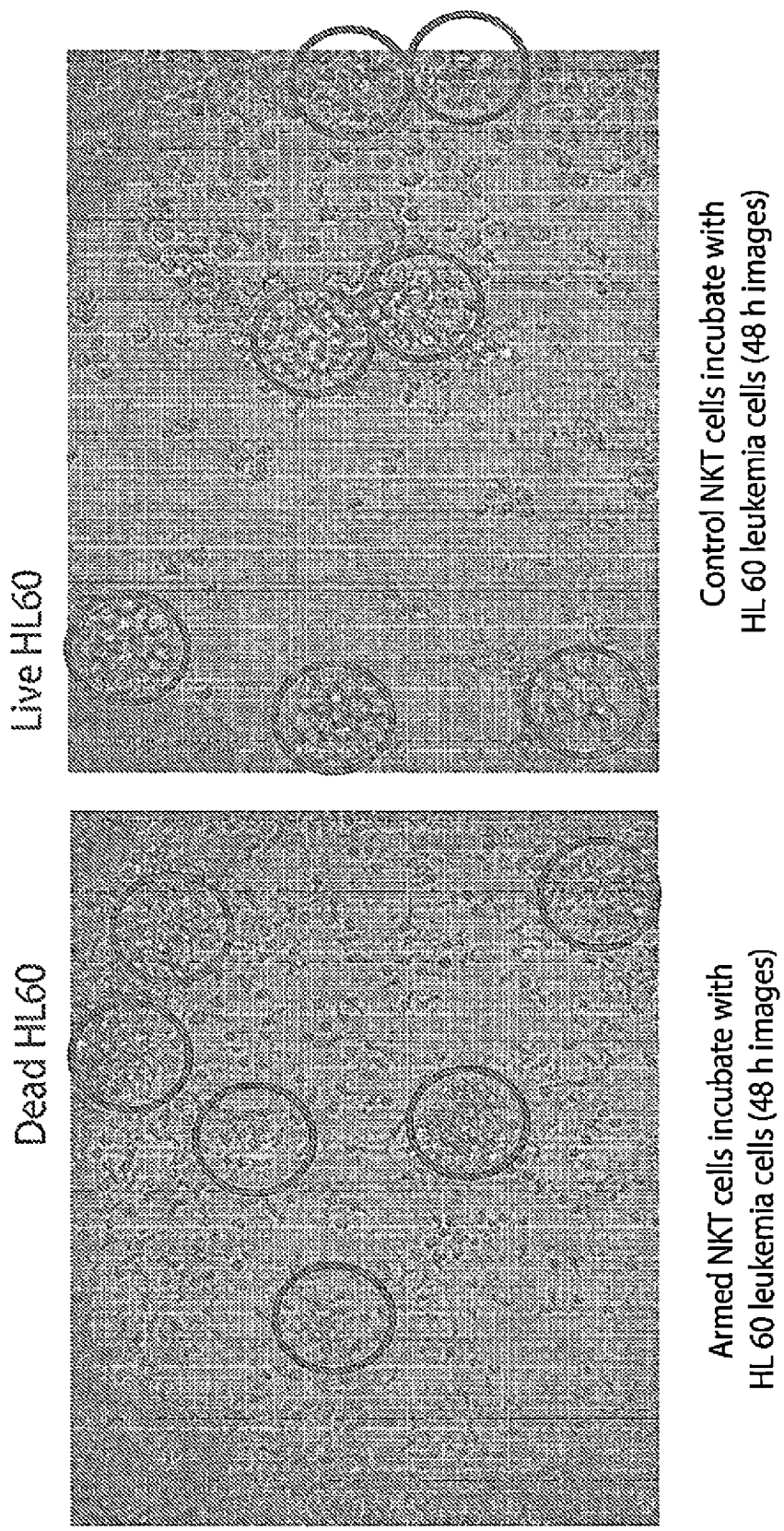
FIG. 6 shows microscopy images illustrating induction of target cell death by complexed cells, according to an embodiment.

In a similar experiment, cell killing is demonstrated for armed NKT cells targeting HL60 leukemia cells by changes in cell morphology. Results are shown in FIG. 6. A much greater proportion of HL60 cells incubated for 48 hours with armed NKT cells were dead, as compared to HL60 cells incubated with uncomplexed control NKT cells for the same period of time.

Example 5: T-Cells Complexed with Rituxan Induce Target Cell Death

Figure 12:
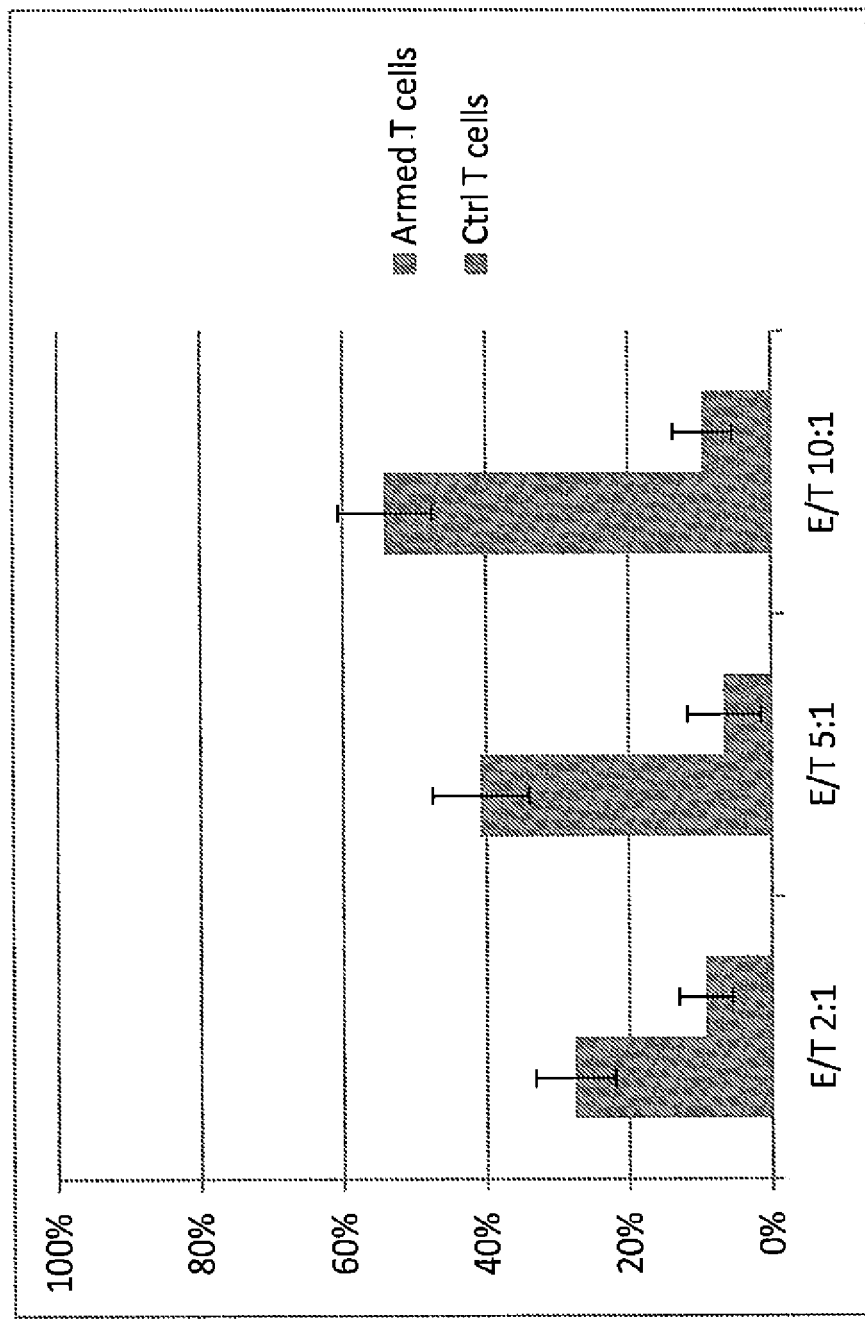
FIG. 12 shows results of an example cell death (cytotoxicity) assay. Bars from left to right in each pair correspond to groups listed in the legend from top to bottom, respectively.
Figure 13:
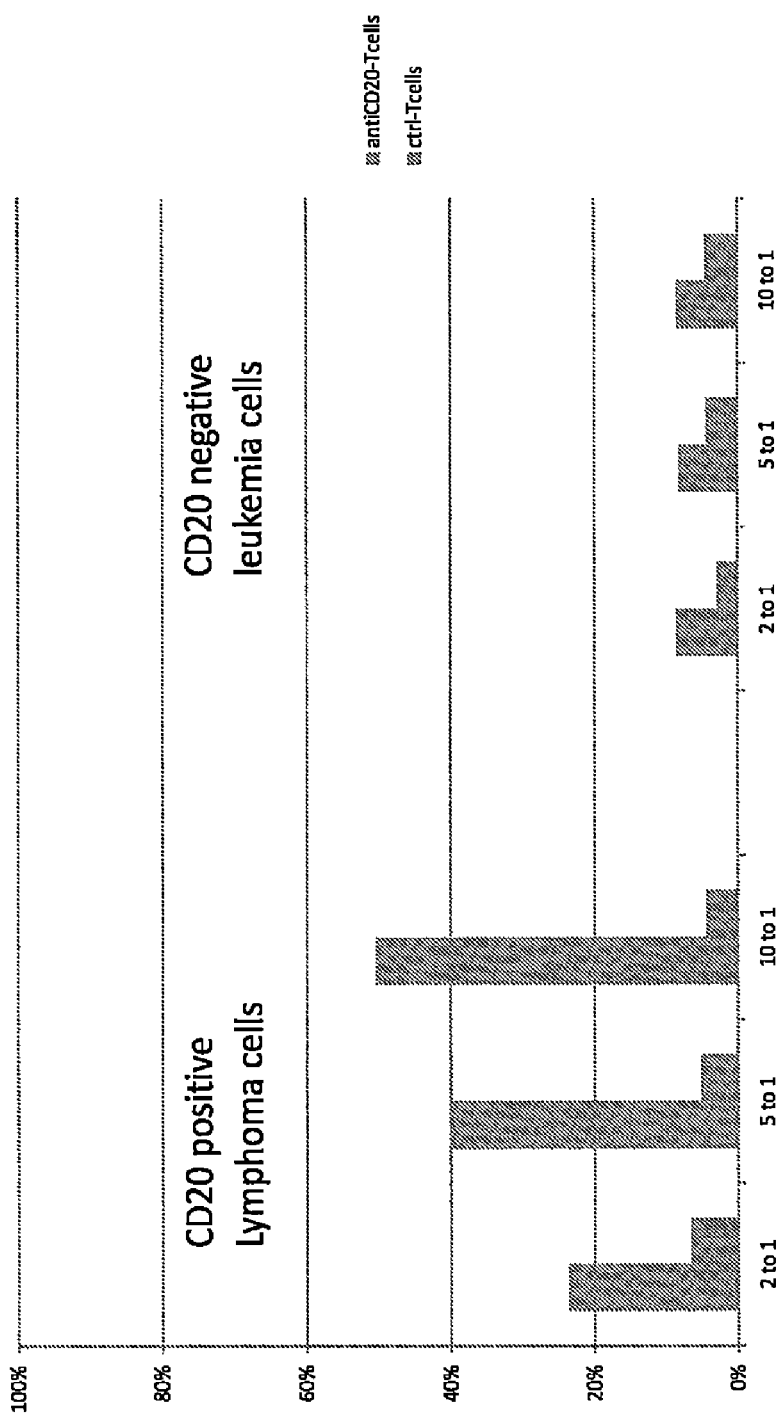
FIG. 13 shows results of an example cell death (cytotoxicity) assay. Bars from left to right in each pair correspond to groups listed in the legend from top to bottom, respectively.
Figure 14:
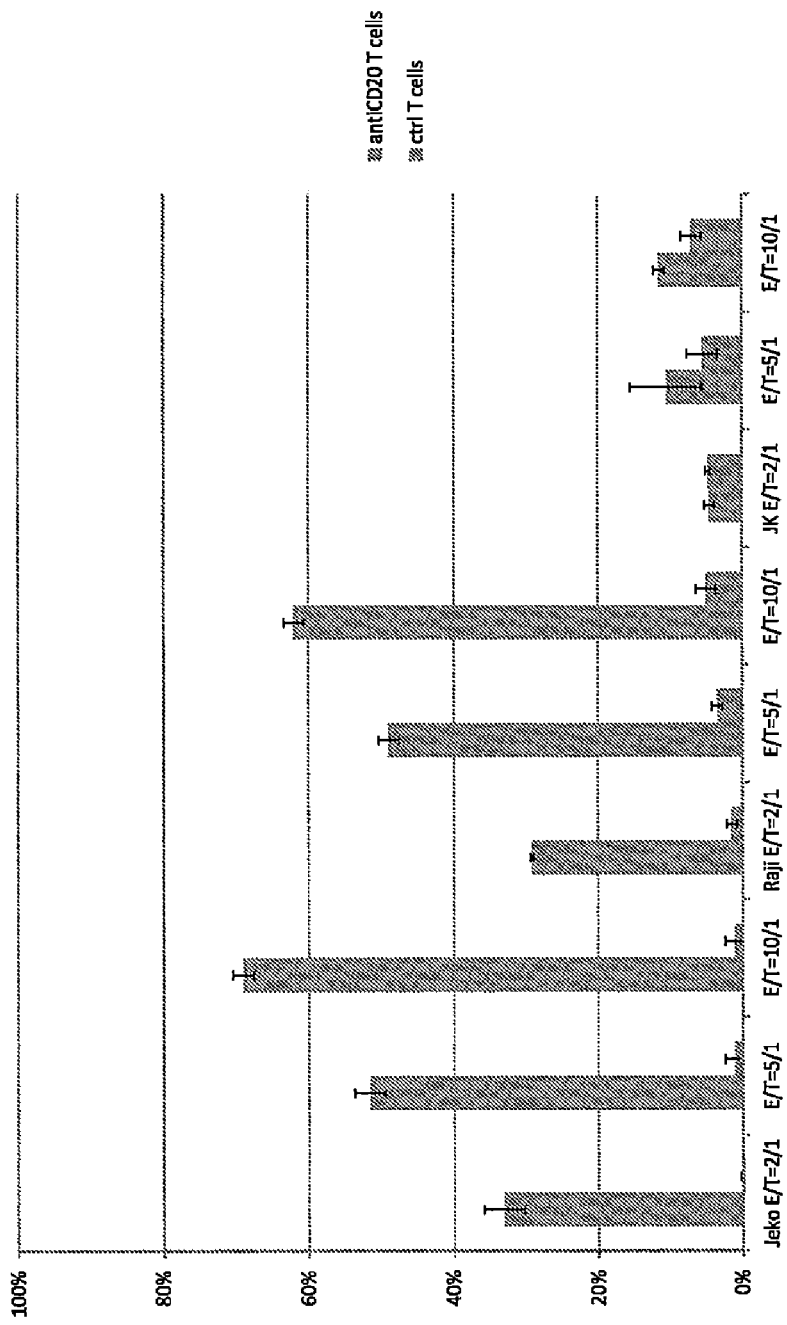
FIG. 14 shows results of an example cell death (cytotoxicity) assay. Bars from left to right in each pair correspond to groups listed in the legend from top to bottom, respectively.

For the purposes of this example, assessing target cell death followed the following general assay parameters. Linker1 with a coupling group was prepared as in Example 1. 175 μL C2.SH was combined with 1.2 μL of the NHS-PEO-Mal linker1 reaction, and incubated at room temperature for 20 minutes. A pellet of 5 million gd T cells was reacted with the resulting C2-NHS linker1. Pellets were broken by resuspending 20 times. The reaction was mixed by orbital shaking for 25 minutes at room temperature. Cells were then washed twice with 5 mL PBS. Cells were then combined with Rituxan antibody conjugated to linker2 as in Example 2 (M2-Rit), and incubated for 15 minutes while orbital shaking. Cells were washed twice with 5 mL PBS, and resuspended in growth media (RPMI). 1 million target cells (Jeko, JK, or Daudi cells) were prepared in parallel by spinning down, resuspending in 1 mL PBS, adding 0.5 μL Cell Tracker Green (reacted for 15 minutes, before washing with 5 mL PBS), and resuspending in 1 mL growth media. Control (un-complexed) T cells were also prepared by spinning down 3 million gd T cells, washing in 10 mL PBS, and resuspending in 1 mL RPMI. Cells were distributed to the wells of a 96-well plate, with 100 uL of growth media per well. Plates were shaking at room temperature for 30 minutes, and incubated at 37° C. and 5% $CO_2$ for 4-6 hours. Cells were stained with propidium iodide (PT, a fluorescent DNA intercalator for identifying dead cells), which was prepared by dissolving 4 μL of 1 mg/mL PI solution in 396 μL PBS and added to wells at 5 μL per well. Cells were incubated with PI stain for 15 minutes in the dark. Cells were transferred to a disposable flow plate, and flow cytometry was performed to obtain fluorescent measurements for cells. Target cells were identified based on the Cell Tracker Green fluorescence, and dead cells were distinguished from live cells by a higher level of PI fluorescence. FIG. 12 shows the results of incubating armed or control T cells (E) to target cells (T) at the specified ratios for 4 hours, expressed as percent dead cells. The armed cells induced significantly more cell death. Similarly, to generated the results illustrated in FIG. 13, complexed cells (anti CD20 T cells) or uncomplexed control T cells were combined with CD20 positive lymphoma cells (left set of bars) or CD20 negative leukemia cells (right set of bars) at the specified ratios of conjugated to target cells, shaken an room temperature for 1 hours, and incubated at 37° C. for 4 hours. Conjugated cells induced significantly more cell death (percentage shown on Y-axis), but only in target cells bearing the target biological marker, CD20. The protocol in followed for FIG. 13 was repeated for two CD20 positive cell lines (Jeko and Raji cells), with Jurkat cells as the CD20 negative control. The results, illustrated in FIG. 14, are comparable.

Figure 7:
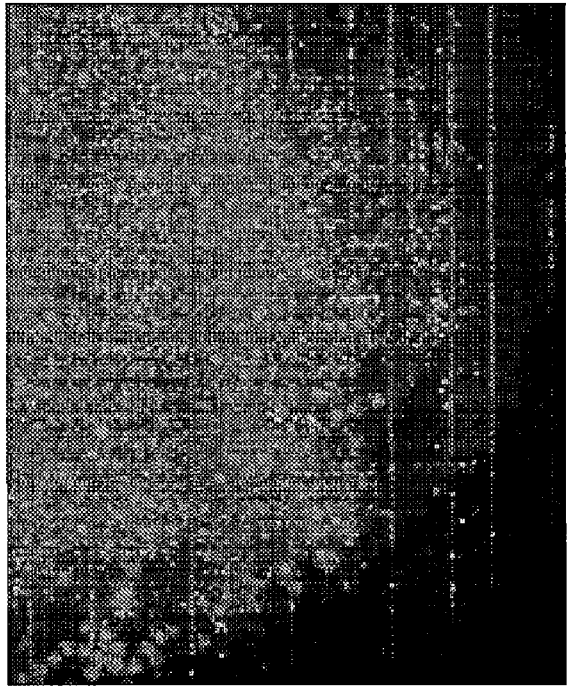
FIG. 7 shows microscopy images illustrating interaction of complexed cells with target cells according to an embodiment.
Figure 7:
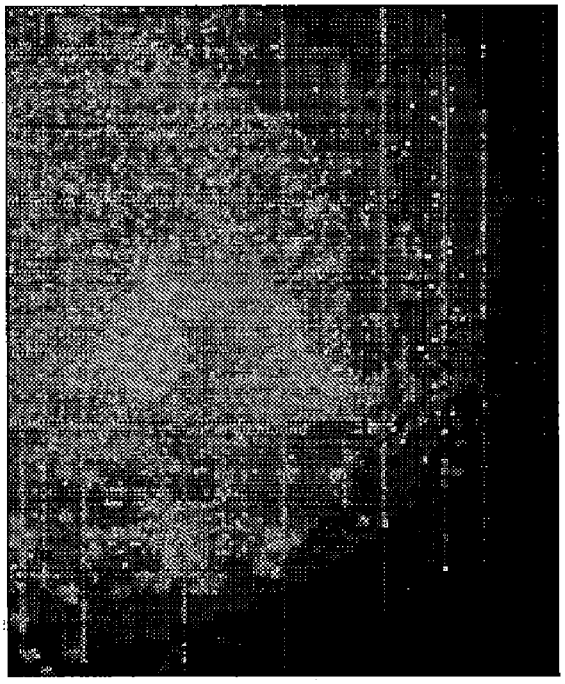

For FIG. 7, cells were visualized under microscopy instead of subjected to flow cytometry. For the images in FIG. 7, T cells complexed with Rituxan (Rit-T cells, orange) were mixed with Jeko lymphoma cells (green) and shaken at room temperature for 30 hours. The microscopy images illustrate the high degree of overlap in signals from complexed cells and target cells, indicating interaction between conjugated cells and target cells. In contrast, uncomplexed (unmodified) T cells did not show an appreciable degree of interaction with target cells under similar conditions.

Example 6: Target Cell Killing in Whole Blood

Figure 15:
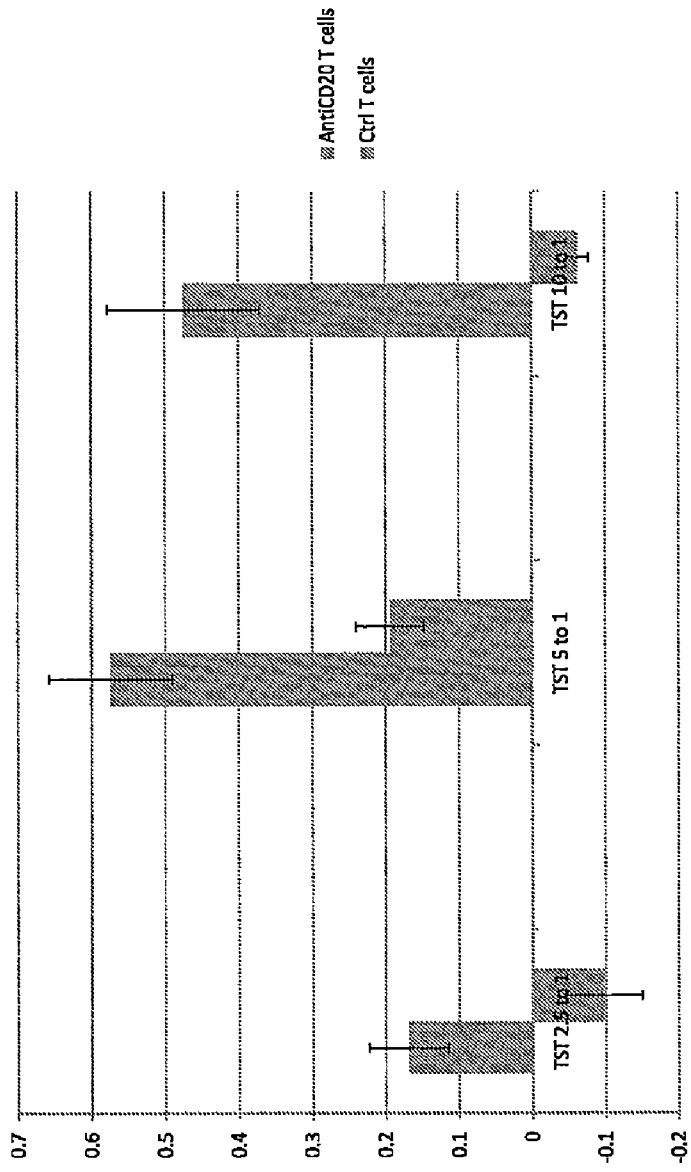
FIG. 15 shows results of an example cell death (cytotoxicity) assay in whole blood. Bars from left to right in each pair correspond to groups listed in the legend from top to bottom, respectively.

The ability of complexed cells to induce cell death in target cells in whole blood, as opposed to media was also evaluated, and results are shown in FIG. 15. Complexed T-cells and control T cells were prepared as in Example 5. 0.2 to 1 million Rituxan-conjugated gd T cells (AntiCD20 T cells, left bars in a pair) or control T cells (right bars in a pair) were added into 100 μL of whole blood, and shaken at room temperature for 1 hour, then incubated at 37° C. for 16 hours. Remaining live B cells were stained with anti-CD20-APC antibody, and counted using a flow cytometer. Results for the indicated ratios of complexed or control cells to target cells are shown as a fraction of dead cells. As an alternative measure of cell death in whole blood, Ramji cells, prepared as in Example 5, could be used as target cells and mixed with the conjugated or control cells in whole blood (e.g. 0.5 million Raji cells mixed with 1 mL of whole blood).

Example 7: T-Cells Complexed with Anti-Her2 Induce Target Cell Death

Figure 16:
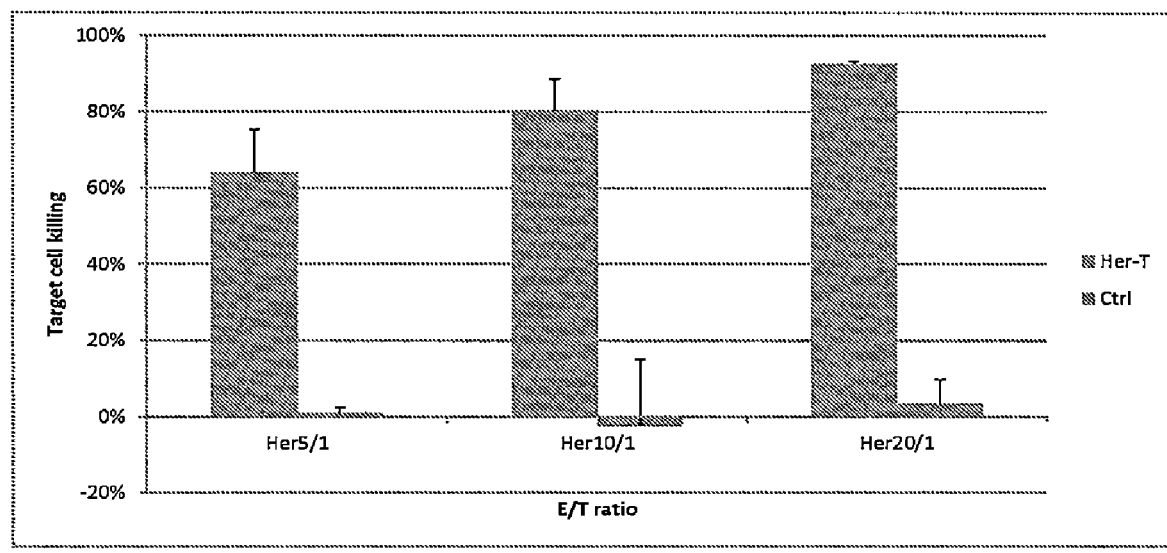
FIG. 16 shows results of an example cell death (cytotoxicity) assay. Bars from left to right in each pair correspond to groups listed in the legend from top to bottom, respectively.

The ability of armed T-cells to trigger cell death in breast cancer cells was evaluated in a flow-cytometry cell death assay, similar to that used in Example 5. The results are shown in FIG. 16. T-cells complexed with anti-Her2 antibody (Her-T), and uncomplexed control cells (Ctrl) were prepared in a process similar to that used in Example 5 for Rituxan antibody complexes and controls. SKBR3 cells, a breast cancer cell line that expresses Her2, were prepared as target cells in a process similar to the preparation of target cells in Example 5. Complexed or uncomplexed cells were combined with target cells in the indicated ratios, and incubated in DMEM for 16 hours at 37° C. Percent of dead target cells was measured by flow cytometry as in Example 5. The results show that uncomplexed control T cells did not induce a significant level of cell death, while complexed cells induced between 60% to about 90% cell death.

Example 8: Linker Design and Analysis

Sequences were evaluated for conformance with a variety of parameters, including lacking homology with known genome sequences, avoiding immunogenic sequences (e.g. CpG sequences), avoiding sequences with secondary structure, having a melting temperature above 55° C., and either repetitive sequences or pairs of linkers that were 20 nt or 40 nt long and having the same nucleotide proportions. Pairs of linkers were selected for further analysis. These pairs were SEQ ID NO: 1 and SEQ ID NO: 2; SEQ ID NO: 3 and SEQ ID NO: 4; SEQ ID NO: 5 and SEQ ID NO: 6; SEQ ID NO: 7 and SEQ ID NO:8; SEQ ID NO: 9 and SEQ ID NO: 10; SEQ ID NO 11 and SEQ ID NO: 12; SEQ ID NO: 13 and SEQ ID NO: 14; SEQ ID NO: 15 and SEQ ID NO: 16; SEQ ID NO: 17 and SEQ ID NO: 18; SEQ ID NO: 19 and SEQ ID NO: 20; SEQ ID NO: 21 and SEQ ID NO: 22; and SEQ ID NO: 23 and SEQ ID NO: 24, as shown in Table 1. Linker functionality was then verified by measuring formation of complexes between cells conjugated to one linker of a pair and an antibodies conjugated to the other linker of a pair.

Example 9: Preparation of Complexed CIK Cells

A population of cells enriched in Cytokine Induced Killer (CIK) cells can be generated from peripheral blood mononuclear cells (PBMC) by in-vitro culture in presence of IFN-γ, OKT-3, and IL-2. High dose Th1-type hormonal stimulation of α/β T-cells with IFN-1, OKT-3 and IL-2 can be used to produce an enriched population of CIK AI cells. The CIK cells can be $CD3^+CD56^+$ cells. Early CIK cultures can be further enriched via a CD56-magnetic bead column. For single cell CIK cloning, T cells can be purified from source LGL by FACS sorting for presence of CD3 or CD56 and absence of CD16. Cells can be expanded to more than $2\times10^6$ cells each.

Expanded CIK cells can then be conjugated to a linker polynucleotide, such as described in Example 1. Conjugated cells can then be combined with conjugated Rituxan antibodies to form complexes comprising CIK cells complexed with Rituxan, in accordance with Example 3. Effectiveness of complexed CIK cells in killing target cells, such as cancer cells, is demonstrated in accordance with Examples 5-7.

Example 10: Effects of Linker Length on Cell Killing

Figure 18:
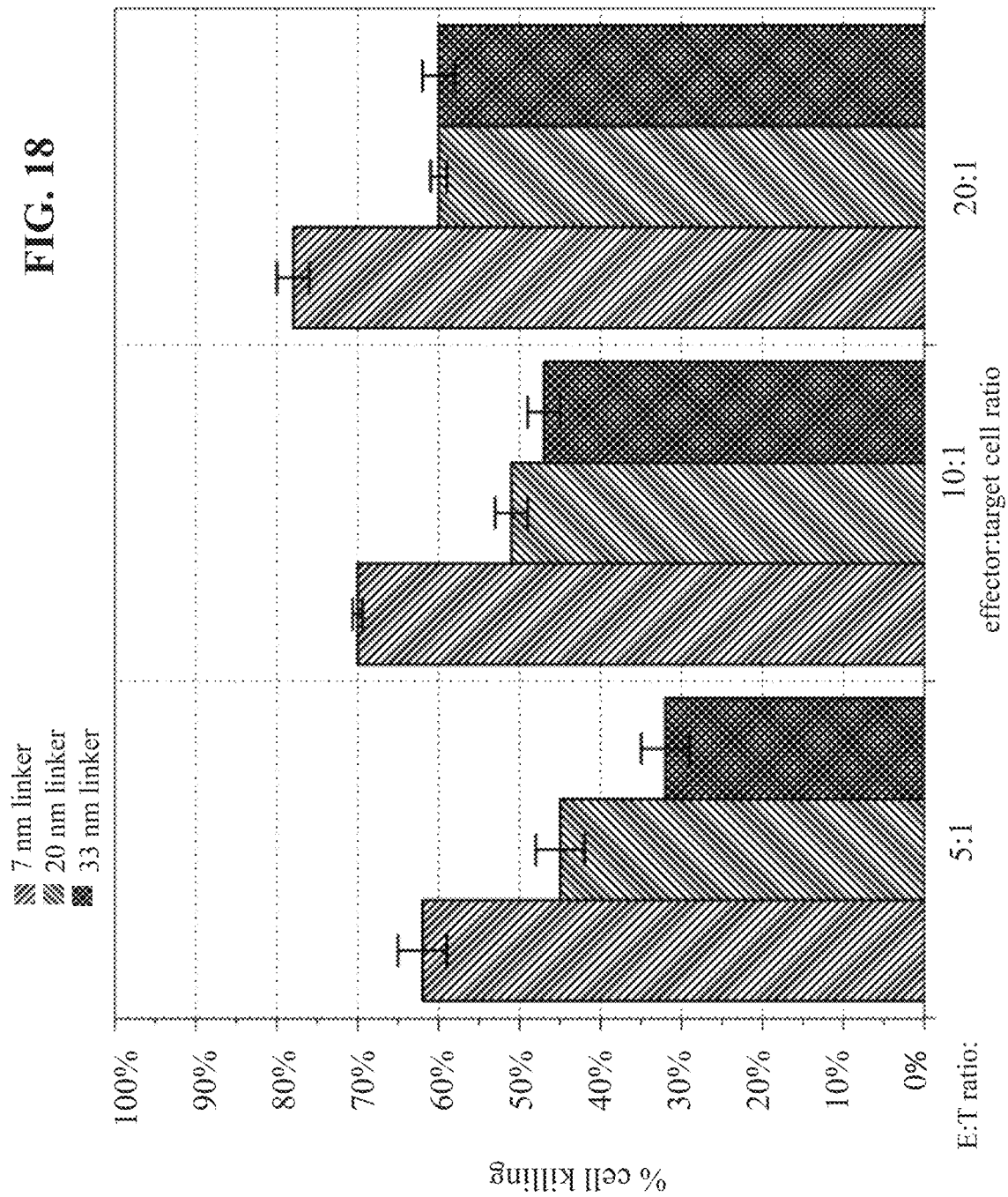
FIG. 18 is a graph showing effect of linker length on % cell killing (y-axis) for the indicated effector cell to target cell ratios (x-axis; groups from left to right—5:1, 10:1, 20:1). Within each triplet, the bars represent results for linkers of 7 nm, 20 nm, and 33 nm, respectively.
Figure 19:
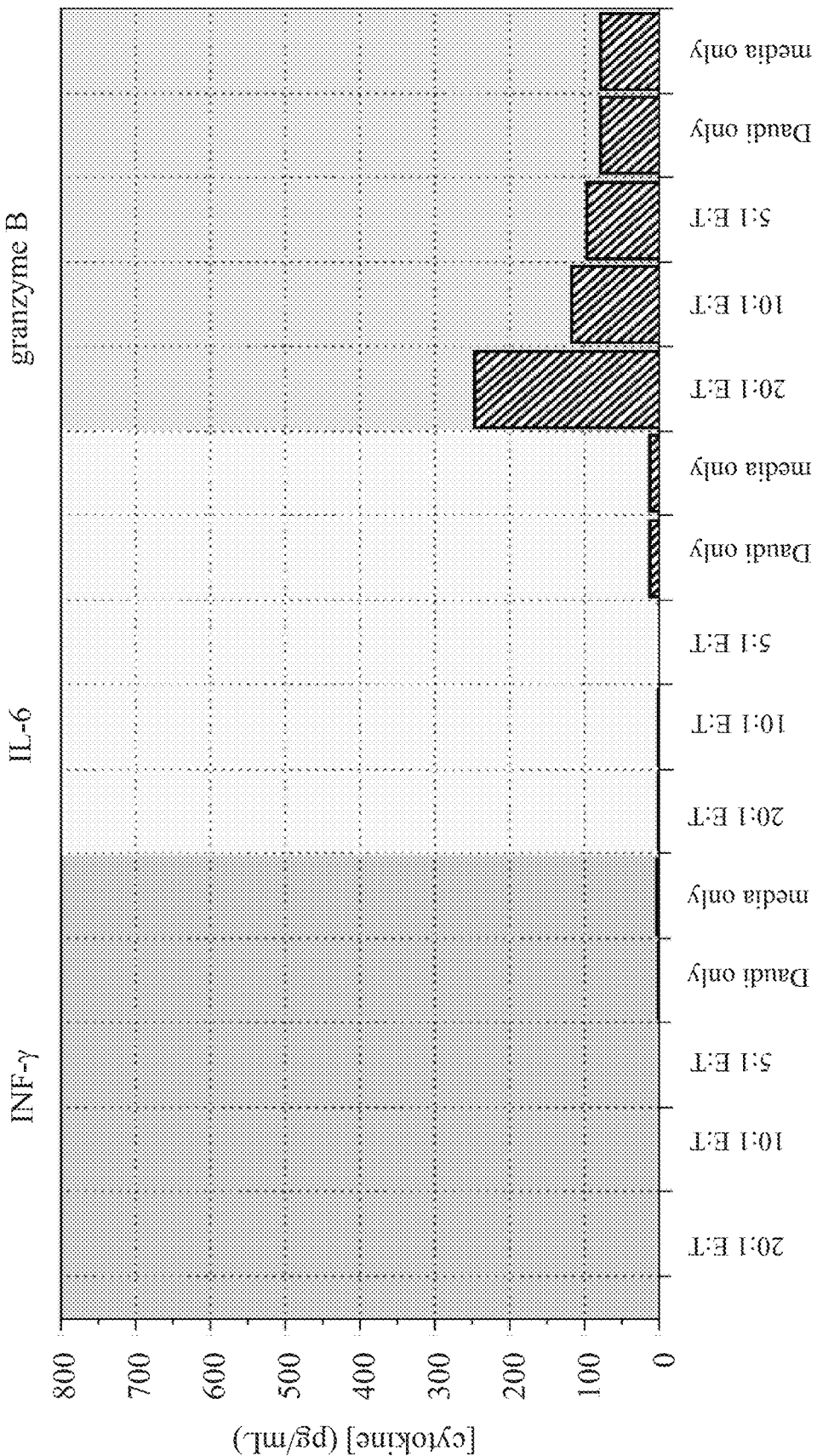
FIG. 19 is a graph showing control NK92 cytokine release. Each group of 5 bars corresponds to results for INFγ, IL-6, and granzyme B, respectively. The y-axis is cytokine level in pg/mL.
Figure 20:
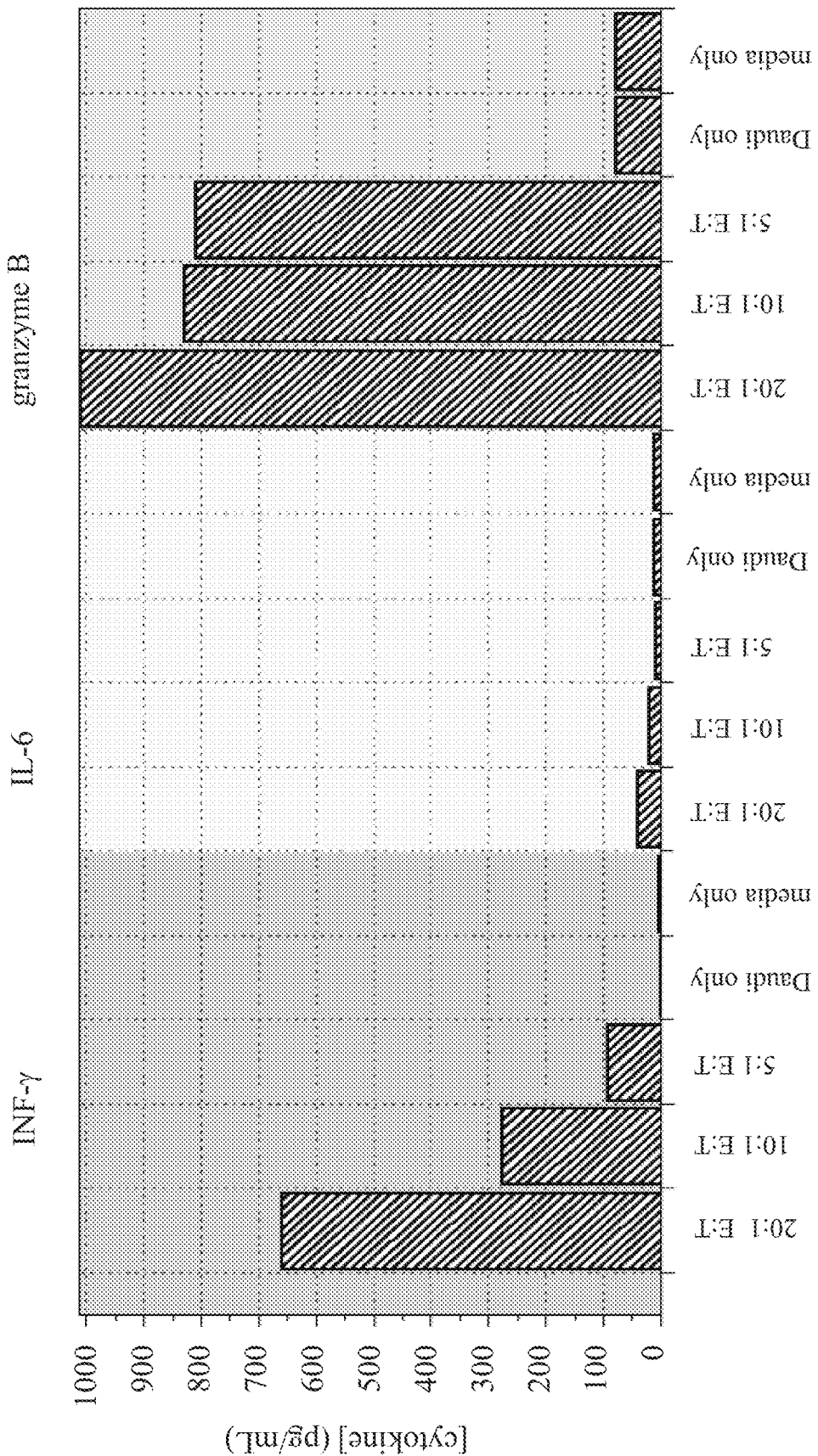
FIG. 20 is a graph showing NK92 PICK cytokine release. Each group of 5 bars corresponds to results for INFγ, IL-6, and granzyme B, respectively. The y-axis is cytokine level in pg/mL.
Figure 21:
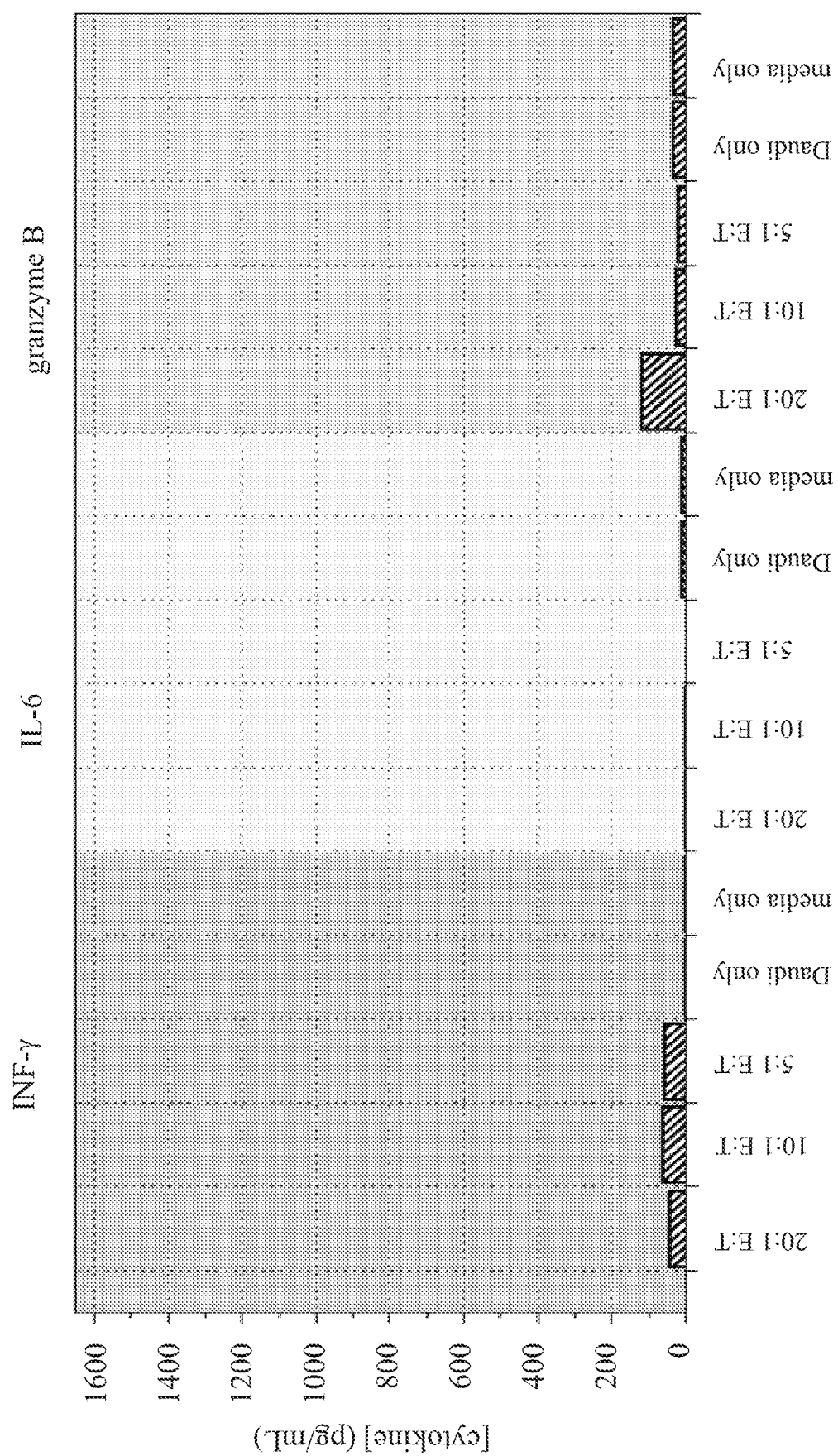
FIG. 21 is a graph showing control T-cell cytokine release. Each group of 5 bars corresponds to results for INFγ, IL-6, and granzyme B, respectively. The y-axis is cytokine level in pg/mL.
Figure 22:
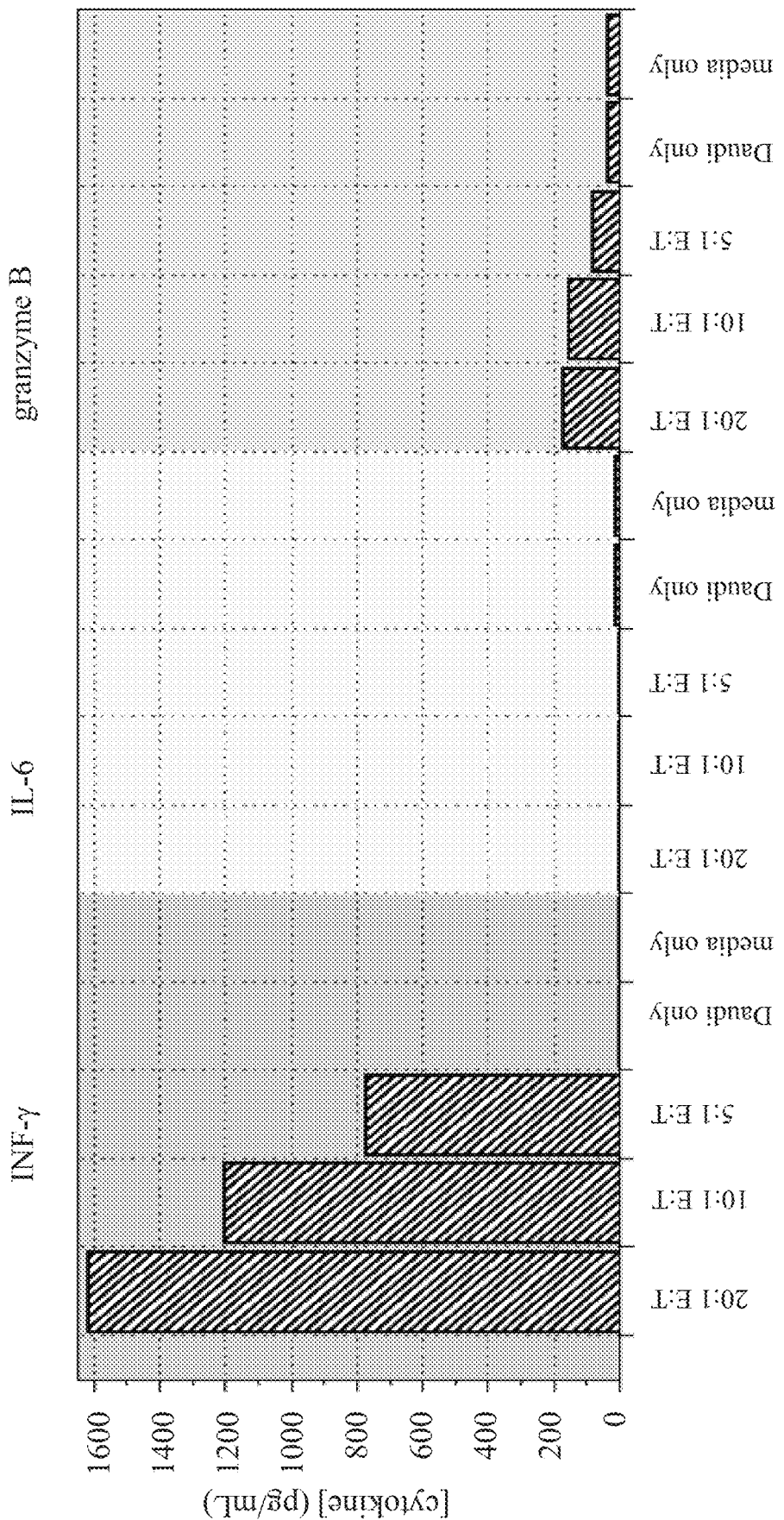
FIG. 22 is a graph showing T-PICK cytokine release. Each group of 5 bars corresponds to results for INFγ, IL-6, and granzyme B, respectively. The y-axis is cytokine level in pg/mL.

T-cells were complexed to Rituxan antibody as in Example 3. Linkers of 7 nm, 20 nm, or 33 nm were used. Control gamma/delta T-cells (gd-T cells) were prepared by spinning down 15 million gdT-cells, washing once in 5 mL PBS, and resuspending in 2 mL growth media (RPMI). 3 million Raji cells were prepared by washing once with 5 mL PBS, spinning down, resuspending in 1 mL PBS, addition 0.5 μL Cell Tracker Green from a stock solution, reacting at room temperature for 8 minutes, resuspending to 2 mL in growth media. Cell densities were counted. 10000 Raji cells were loaded per well on a 96-well plate. Complexed gdT-cells or control gdT-cells were added at ratios to Raji cells of 5:1, 10:1, or 20:1. 100 μL growth media were added to each used well. The plate was shaken at room temperature for 30 minutes (Orbital shaking at mark 7). Wells were checked by microscopy for the formation of cell-cell aggregates. PI stain was prepared by diluting a 1 mg/mL solution of P1 1 to 100 in PBS. Wells were stained for 15 minutes, incubating in the dark. Results were measured by flow cytometry, and are illustrated in FIG. 18.

Example 11: Effects of Rituxan-Complexed Cells Against Daudi Lymphoma Cells

T-cells and NK92 cells were separately complexed to Rituxan antibody as in Example 3. Control T-cells and control NK92 cells were separately prepared by spinning down, washing once in 5 mL PBS, and resuspending in 2 mL growth media. For each test, 2 million Daudi cells were prepared by washing with 5 mL PBS, spinning down, and resuspending in 1 mL PBS. 0.3 μL Cell Track Green (from stock solution of 2 μg/μL) were added to the Daudi cell solution, and reacted at room temperature for 8 minutes. Cells were resuspended to 2 mL in growth media. Cell densities were determined. 10000 Daudi cells were loaded per well on a 96-well plate. Complexed cells or uncomplexed control cells were added at ratios to Daudi cells of 5:1, 10:1, or 20:1. Even distribution was confirmed by microscopy. The plate was incubated at 37° C. and 5% $CO_2$ for 24 hours. Wells were checked by microscopy for the formation of cell-cell aggregates. The plate was centrifuged at 1500 rpm for 3 minutes. The supernatant from each well was collected in separate tubes, and frozen at −80° C. for later measurement of cytokine release. The concentrations of INF-γ, IL-6, and granzyme B were determined by standard methods. Results levels of these three cytokines in each of control NK92 cells, complexed NK92 cells (also referred to as "PICK" cells), control T cells, and complexed T-cells are shown in FIGS. 19, 20, 21, and 22, respectively. For each cytokine, measurements in pg/mL are provided for 20:1 E/T, 10:1 E/T, 5:1 E/T, Daudi cells only, media only, from left to right in each group, respectively. E/T indicates the ratio of effector cells (complexed or uncomplexed cells) to target cells (Daudi cells).

Example 12: Effects of Complexed T-Cells in Mouse Cancer Model

Figure 23:
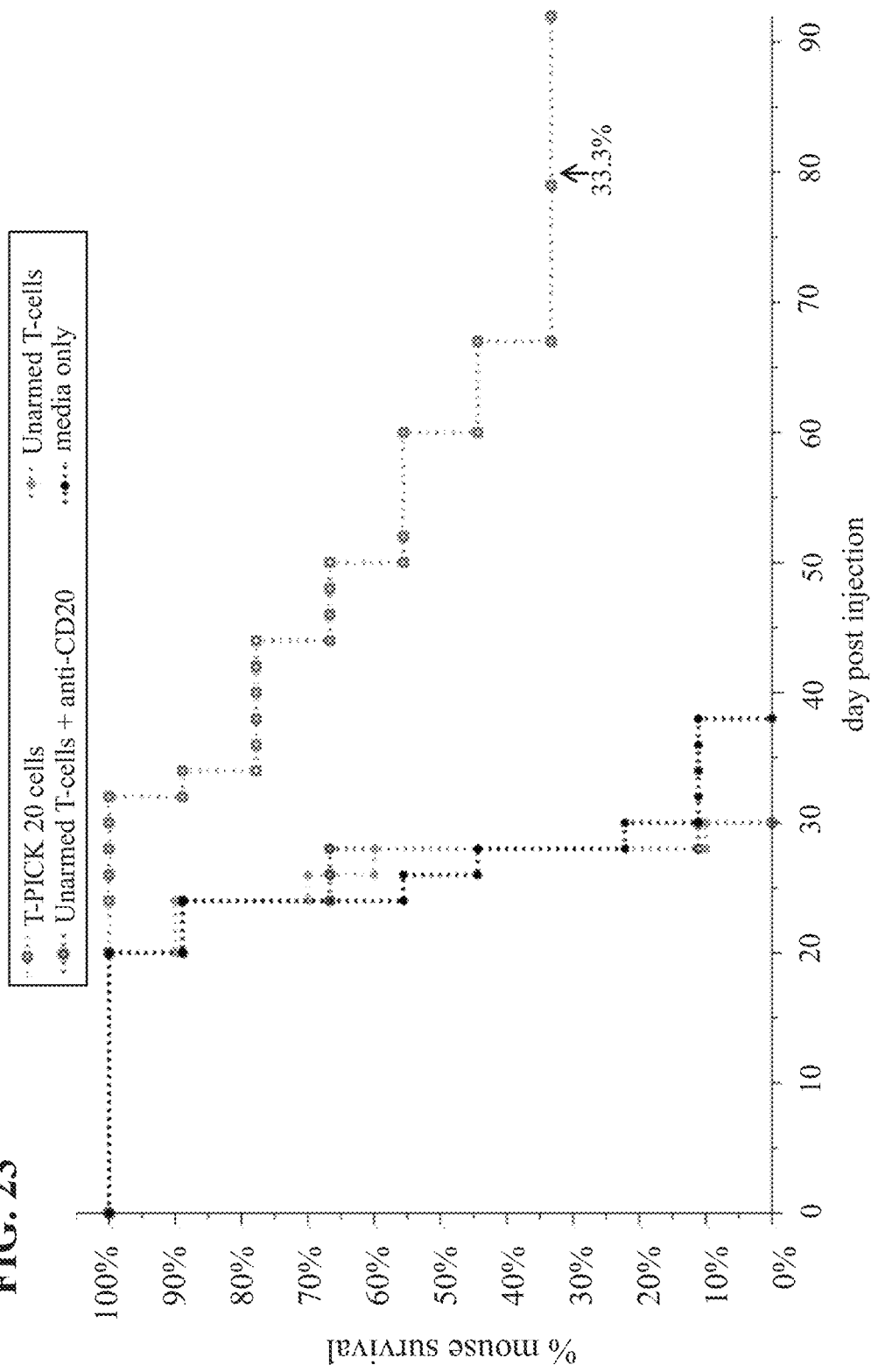
FIG. 23 shows results for an in vivo protocol according to an embodiment. The plot extending furthest to the right of the plot corresponds to T-PICK 20 cells.

T-cells were complexed to Rituxan antibody as in Example 3. Control gdT-cells were prepared by spinning down 100-120 million gdT cells, washing in PBS, and resuspending in 1.2 mL serum-free RPMI. Cell densities were determined, then stored on ice prior to use. The tumor target was Raji lymphoma in a SCID beige mouse model. Mice received a 100 μL tail-vein injection of a cell suspension (or media only) according to their respective groups at days 3, 5, 10, and 17. Results for a first trial are illustrated in FIG. 23, in which the groups were as follows: complexed T-cells ("T-PICK 20 cells"; 9 mice); uncomplexed T-cells plus Rituxan ("unarmed T-cells+anti-CD20"; 9 mice); uncomplexed T-cells ("unarmed T-cells"; 10 mice); serum-free RPMI only ("media only"; 9 mice). Mice that received cells received $5 \times 10^6$ cells in each dose. Results for the complexed T-cells are represented by the far right line showing the highest survival rate.

Figure 24:
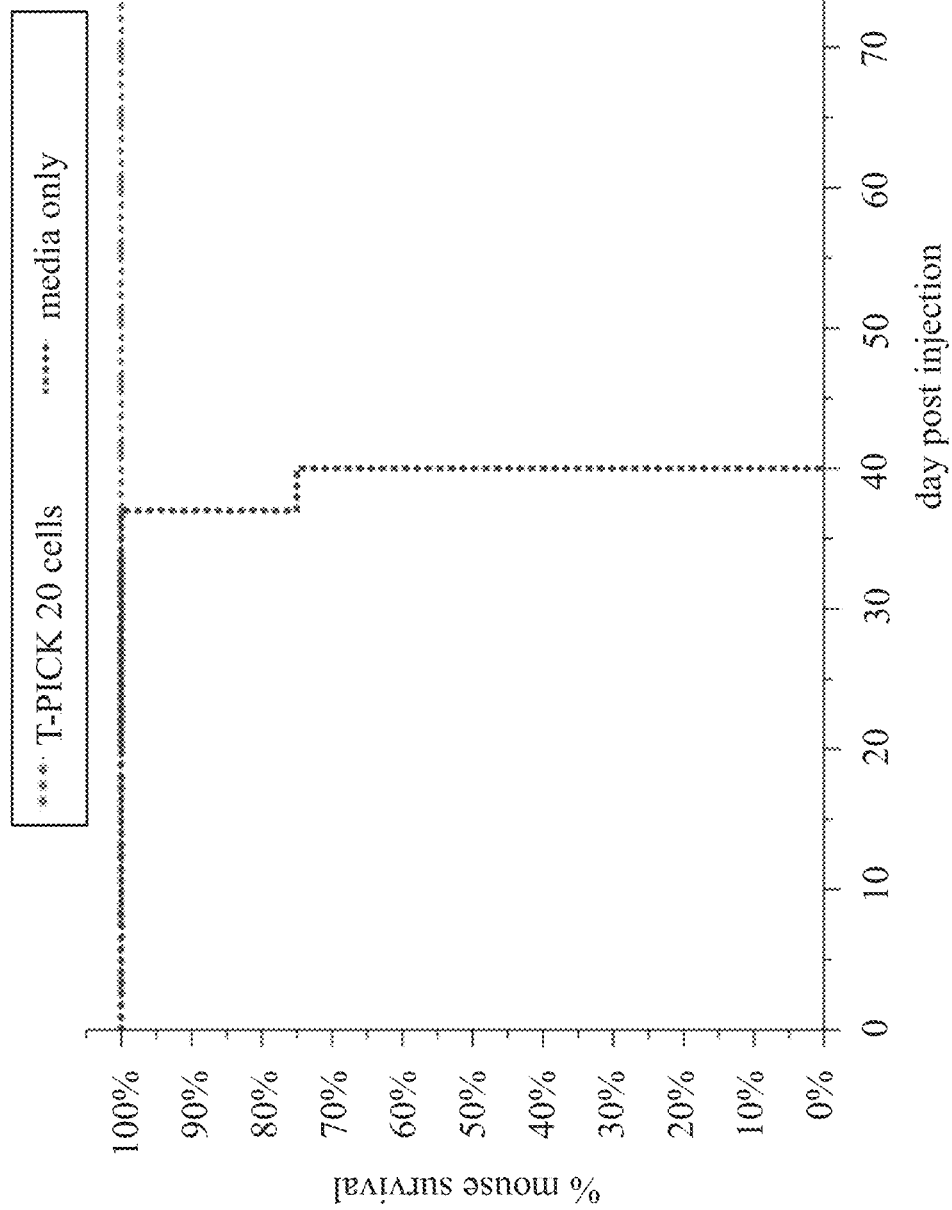
FIG. 24 shows results for an in vivo protocol according to an embodiment. The plot extending furthest to the right of the plot corresponds to T-PICK 20 cells.

Results for a second trial following a similar protocol are illustrated in FIG. 24. In this variation, the tumor target was Daudi lymphoma in SCID beige mouse model, in which groups were as follows: complexed T-cells, uncomplexed control T-cells with Rituxan, uncomplexed T-cells, Rituxan only, and serum-free RPMI only. All groups had 8 mice, except the media-only group, which had 4. Mice receiving cells received $10 \times 10^6$ cells in each dose. FIG. 24 illustrates results for the complexed T-cells ("T-PICK 20 cells") and serum-free RPMI only ("media only") groups. The group treated with complexed T-cells is represented by the line extending furthest to the right, indicating increased survival.

Example 13: Effects of CD16-Positive Complexed Cells on Target Cell Killing

Figure 25:
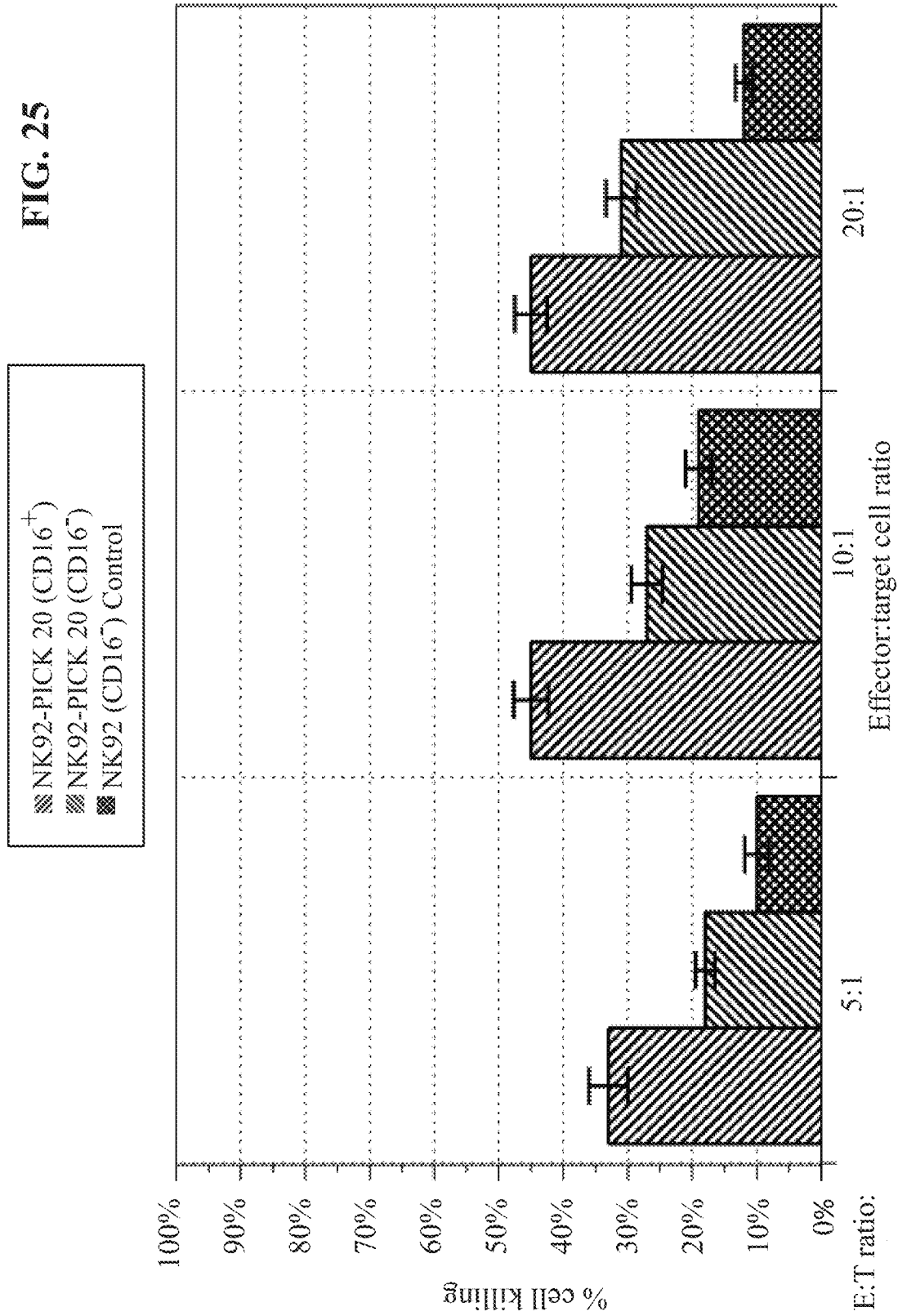
FIG. 25 is a graph indicating that NK92 cells show increased activation with CD16. Results are shown as % cell killing (y-axis) for the indicated effector cell to target cell ratios (x-axis; groups from left to right—5:1, 10:1, 20:1). Within each triplet, the bars represent results for NK92-PICK 20 (CD16$^+$) cells, NK92-PICK 20 (CD16$^-$) cells, and NK92 (CD16$^-$) control cells, from left to right, respectively.

NK92 cells were complexed to Rituxan antibody as in Example 3. This was performed for cells that were CD16-negative, and for cells that were CD16-positive. Target Daudi lymphoma cells were prepared as in Example 11. 10000 Daudi cells were loaded per well on a 96-well plate. Complexed cells or uncomplexed control cells were added at ratios to Daudi cells of 5:1, 10:1, or 20:1. Even distribution was confirmed by microscopy. The plate was incubated at 37° C. and 5% $CO_2$ for 4 hours. Wells were checked by microscopy for the formation of cell-cell aggregates. Cells were stained with 5 μL PI stain, as in Example 10, and results of staining were measured by flow cytometry. Results are illustrated in FIG. 25, which indicate higher percent killing of target cells by the CD16-positive NK92 complexed cells.

Example 14: Efficacy of Complexed Cells Against Different Cancer Targets

Figure 26:
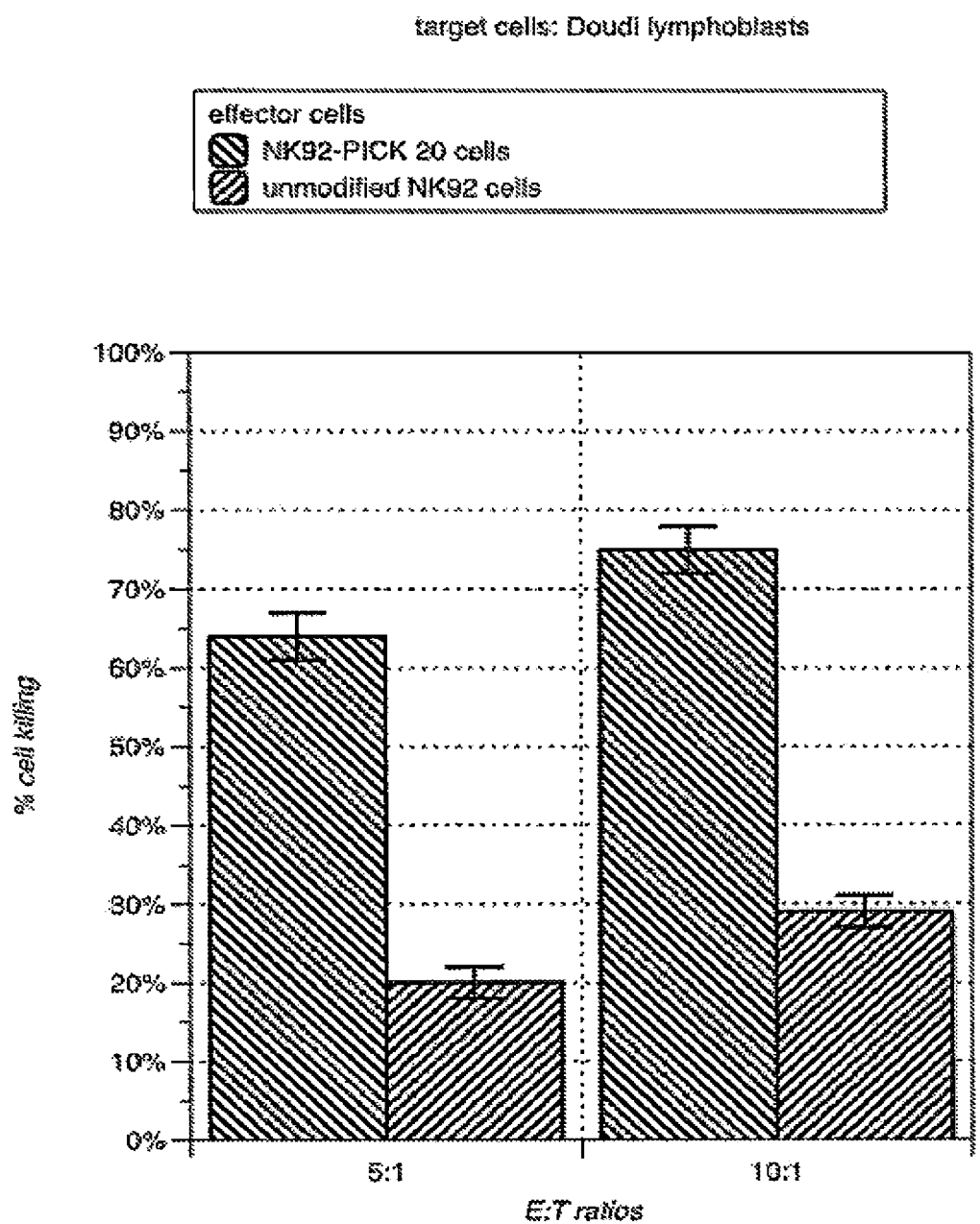
FIG. 26 shows results for NK92 PICK therapy utilizing Rituxan against Daudi lymphoblasts. Results are shown as % cell killing (y-axis) for the indicated effector cell to target cell ratios (x-axis; groups from left to right—5:1, 10:1). Within each pair, the bars represent results for NK92-PICK 20 cells, and unmodified NK92 cells, from left to right, respectively.
Figure 27:
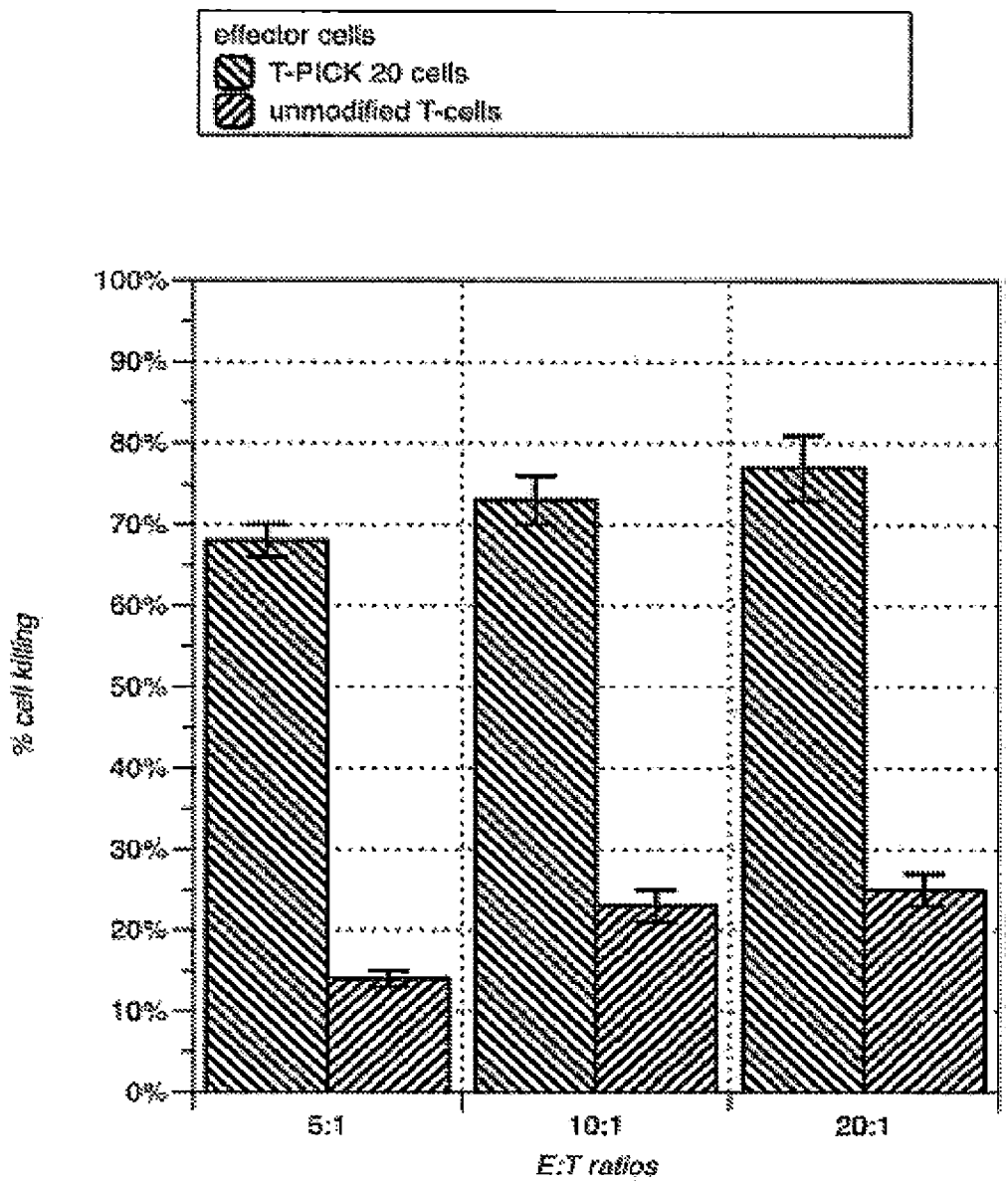
FIG. 27 shows results for T-PICK therapy utilizing Rituxan against Daudi lymphoblasts. Results are shown as % cell killing (y-axis) for the indicated effector cell to target cell ratios (x-axis; groups from left to right—5:1, 10:1, 20:1). Within each pair, the bars represent results for T-PICK 20 cells, and unmodified T-cells, from left to right, respectively.
Figure 28:
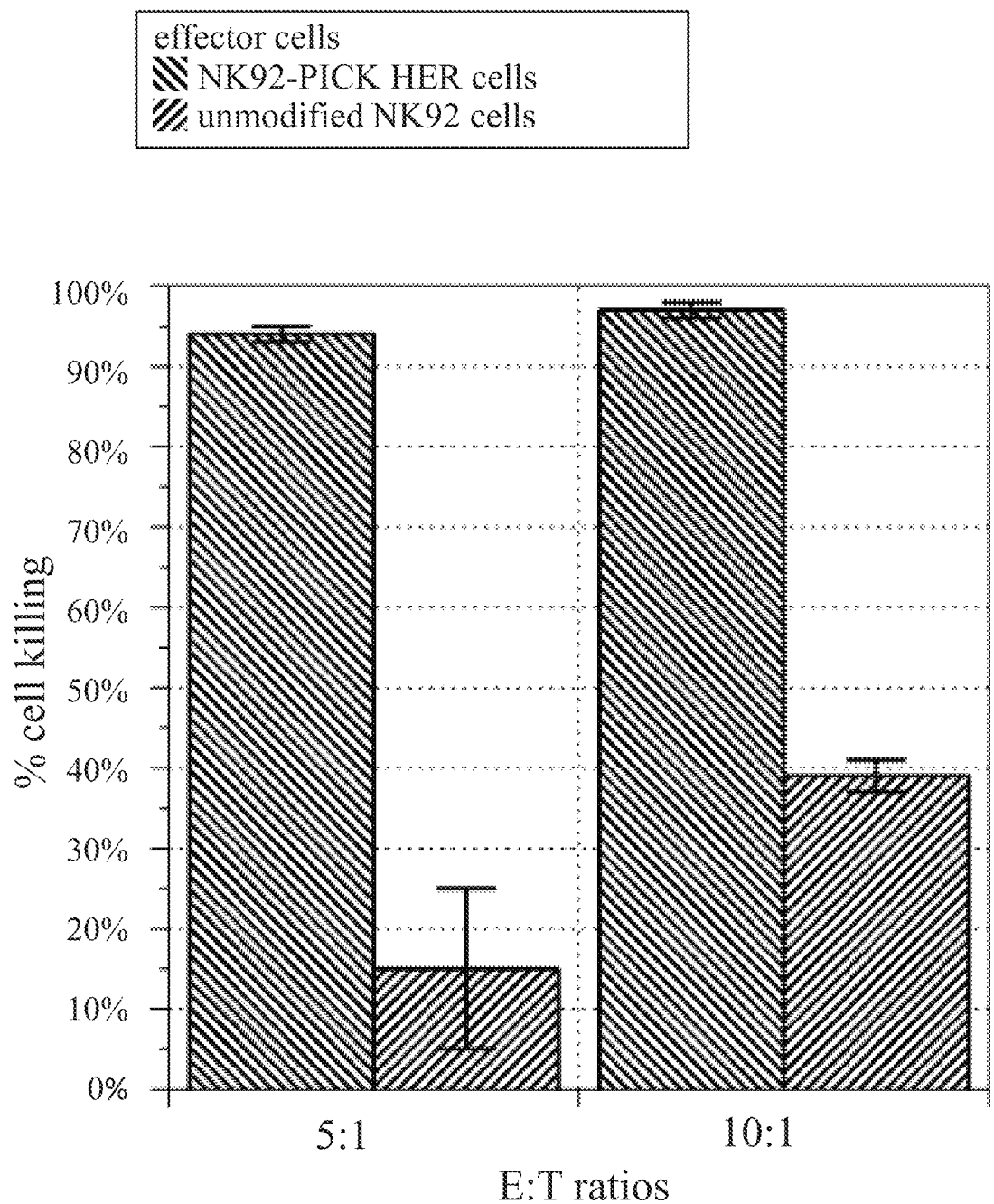
FIG. 28 shows results for NK92 PICK therapy utilizing Herceptin against SKBR3 breast cancer cells. Results are shown as % cell killing (y-axis) for the indicated effector cell to target cell ratios (x-axis; groups from left to right—5:1, 10:1). Within each pair, the bars represent results for NK92-PICK HER cells, and unmodified NK92 cells, from left to right, respectively.
Figure 29:
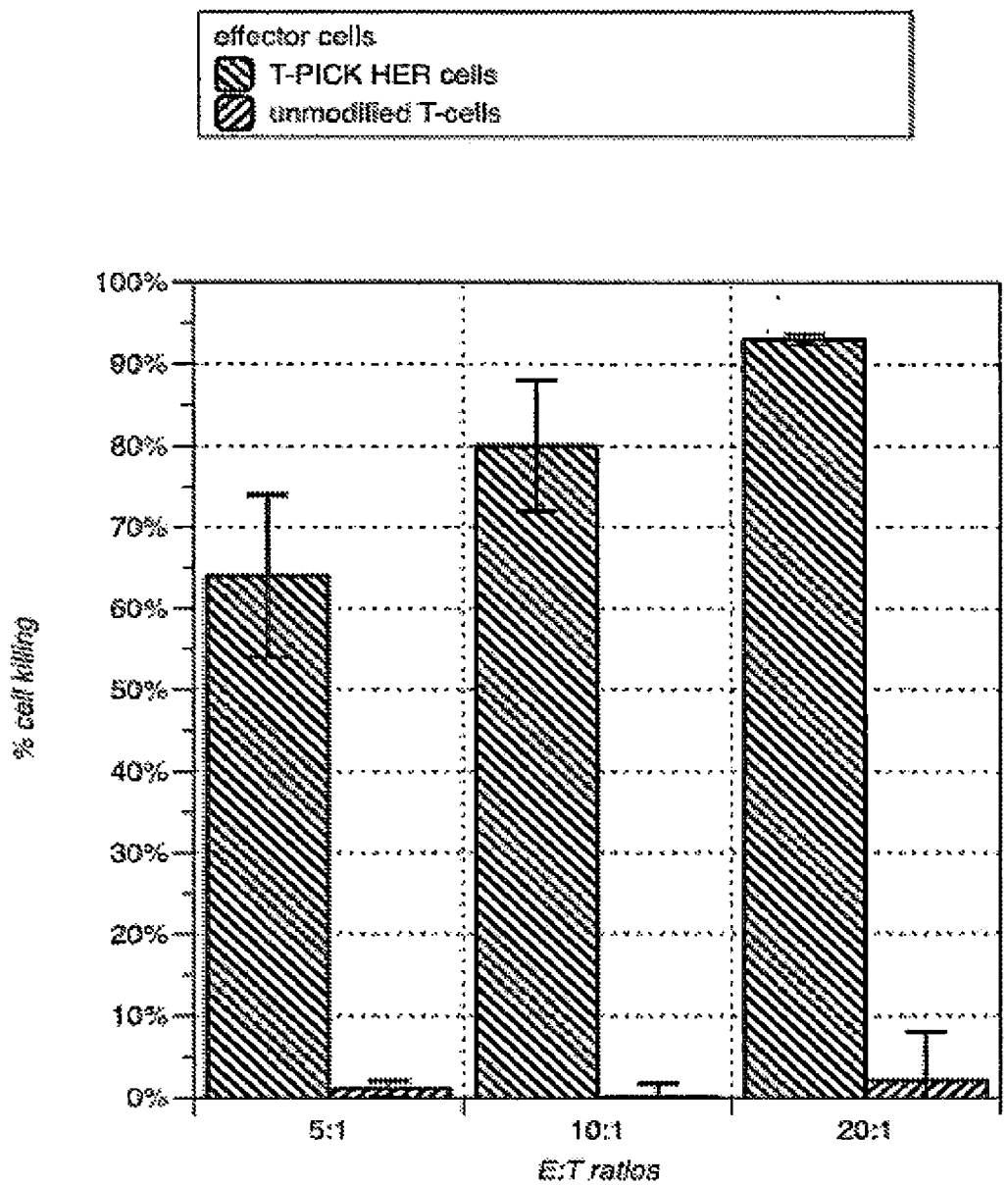
FIG. 29 shows results for T-PICK therapy utilizing Herceptin against SKBR3 breast cancer cells. Results are shown as % cell killing (y-axis) for the indicated effector cell to target cell ratios (x-axis; groups from left to right—5:1, 10:1, 20:1). Within each pair, the bars represent results for T-PICK HER cells, and unmodified T-cells, from left to right, respectively.

NK92 cells were complexed to Rituxan antibody as in Example 3. Cell killing against Daudi lymphoblast cells was measured as in the above examples, with ratios of complexed to target cells of 5:1 and 10:1. Results for complexed and uncomplexed cells are illustrated in FIG. 26. Efficacy of T-cells complexed to Rituxan were similarly measured for ratios of complexed to target cells of 5:1, 10:1, and 20:1, with results for complexed and uncomplexed cells illustrated in FIG. 27. Similar experiments were performed for NK92 and T-cells complexed to Herceptin to measure degree of killing against SKBR3 breast cancer cells, with results shown in FIG. 28 (NK92) and FIG. 29 (T-cells).

Figure 30:
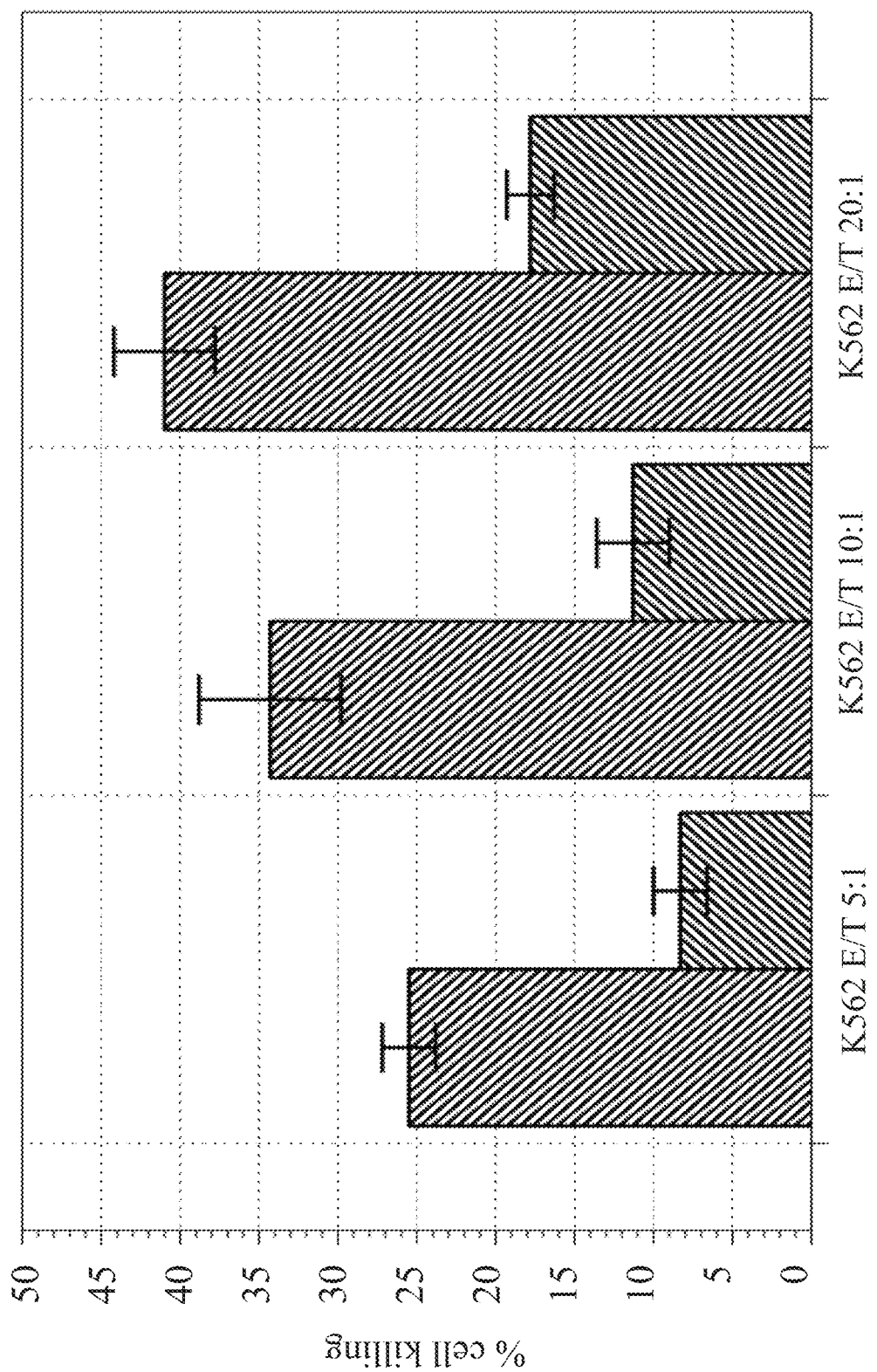
FIG. 30 shows results for T-PICK therapy utilizing ROR-2 against K562 cells. Results are shown as % cell killing (y-axis) for the indicated effector cell to target cell ratios (x-axis; groups from left to right—5:1, 10:1, 20:1). Within each pair, the bars represent results for T-PICK cells, and unmodified T-cells, from left to right, respectively.

T-cells were complexed to Receptor Tyrosine Kinase-Like Orphan Receptor 2 (ROR2), following a procedure similar to that in Example 3, except that ROR2 was conjugated to linker DNA instead of an antibody. Cell killing was measured against K562 target cells as above, with ratios of complexed to target cells of 5:1, 10:1, and 20:1. Results are illustrated in FIG. 30, which also indicate higher target cell killing by complexed cells.

Example 15: Cells Complexed to Rituxan Using Different Polynucleotide Linkers

Cells were complexed to Rituxan as in Example 3; however, different linker pairs were used to test the effects of linker sequence characteristics (e.g. sequence complexity, Tm, secondary structure) on conjugation efficacy. The linker sequences are indicated in Table 2 below. Some DNA sequences are named CA # or GT # (complements), with their version listed after.

TABLE 2

| Sequence 5'→3' | bases | Tm ° C. at 40 μM | length (nm) | Complexity | Notes |
| --- | --- | --- | --- | --- | --- |
| *Poly A 20 mer + PolyT 20mer | 20 | 44 | 6.8 | 1 | |
| *Poly CA 20 mer (CA, GT) | 20 | 63 | 6.8 | 1 | |
| Poly GGTT 20 mer | 20 | 63.7 | 6.8 | 2 | |
| TGG TCT CCT GTG GTC TCC TG (SEQ ID NO: 25) | 20 | 66 | 6.8 | 4 | Hairpin w Tm of 20° C. |

TABLE 2-continued

| Sequence 5'→3' | bases | Tm ° C. at 40 µM | length (nm) | Complexity | Notes |
|---|---|---|---|---|---|
| *Poly GGGTT 20 mer (CA2, GT2) | 20 | 68 | 6.8 | 3 | |
| CGG TCG GCT CGG TCG GCT GG (SEQ ID NO: 26) | 20 | 75 | 6.8 | 4 | Hairpin w Tm of 32° C. |
| *GGGTGGGT 20 mer (CA4, GT4) (SEQ ID NO: 27) | 20 | 75 | 6.8 | 3 | |
| *GGG CGG GCG GGT GGG TGG GC (CA5, GT5) (SEQ ID NO: 28) | 20 | 82 | 6.8 | 4 | Hairpin w Tm of 18° C. |

*denotes a sequence evaluated further in this example.

Figure 31:
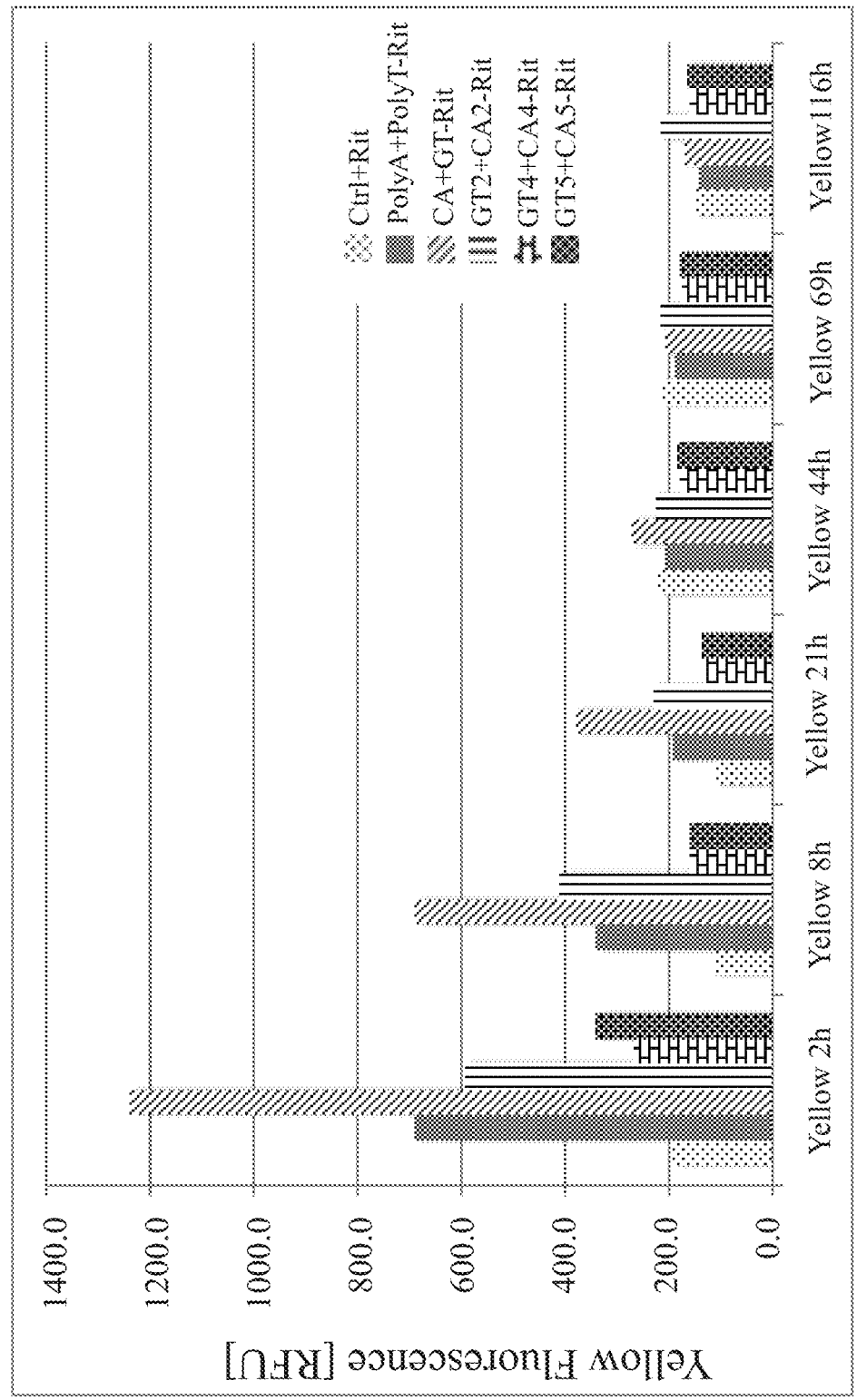
FIG. 31 shows results of an assay for presence of conjugated antibody over time.

Cells complexed to Rituxan were analyzed to determine half-life trends associated with different DNA linkers. complexed cells were assayed at 2, 8, 21, 44, 69, and 116 hours after conjugation for the presence of Rituxan. Ritux was detected an anti-Fab antibody labeled with Phycoerythrin (PE). Fluorescence of the label was quantified by flow cytometry, and results are illustrated in FIG. 31. The six time points are represented by 6 groups of bars, with bars from left to right corresponding to linkers listed in the legend from top to bottom, respectively. Trends indicate different half-lives for conjugation via different linker pairs, and thus tunability of conjugation based on polynucleotide linker sequence.

Figure 32:
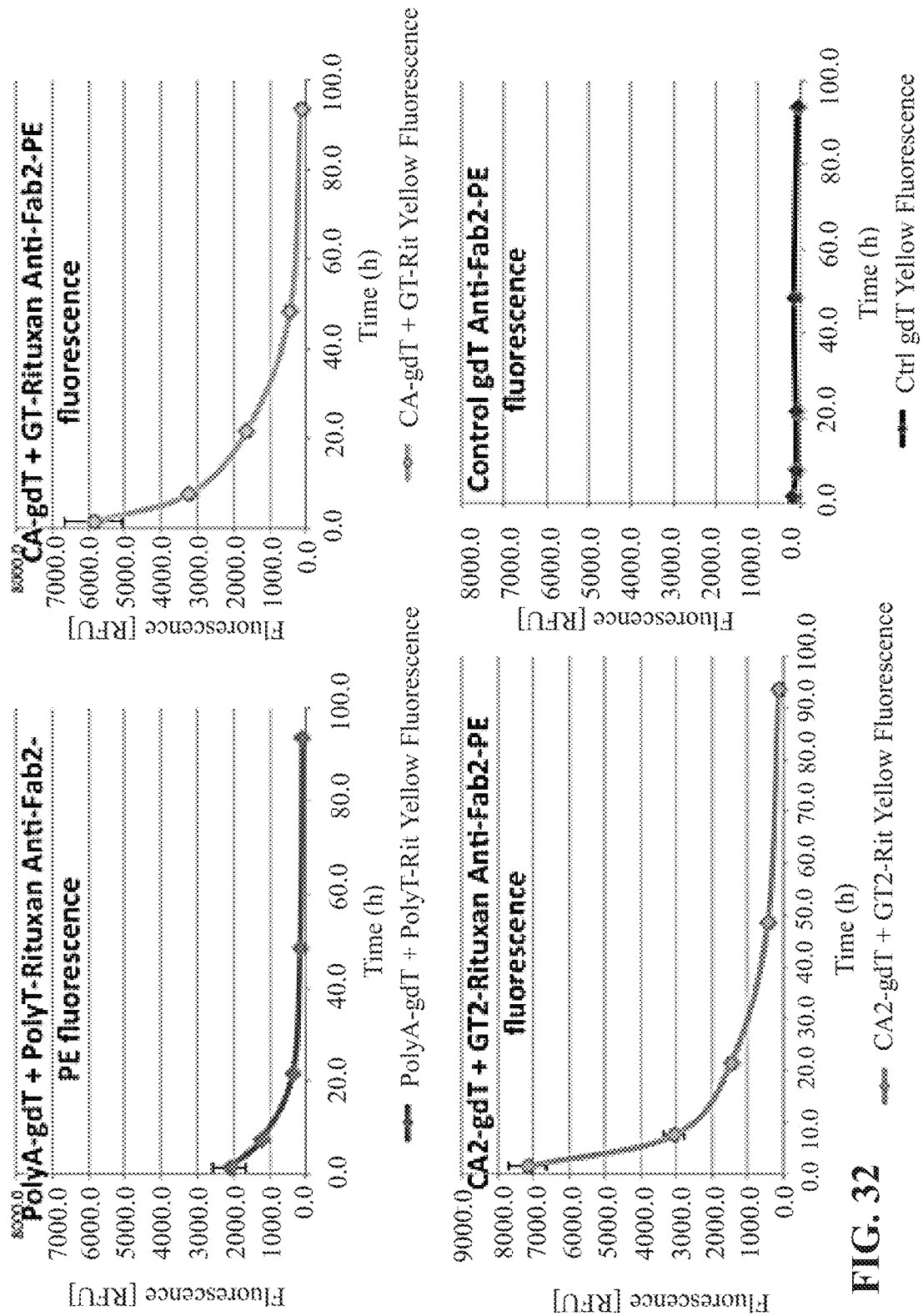
FIG. 32 shows results of an assay for presence of conjugated antibody over time.

This half-life determination experiment was repeated for selected linker pairs, specifically: (1) PolyA-linked T-cells complexed to PolyT-linked Rituxan; (2) CA-linked T-cells complexed to GT-linked Rituxan; and (3) CA2-linked T-cells complexed to GT2-linked Rituxan. Uncomplexed T-cells were used as a control in the detection experiment. Results are plotted in FIG. 32. The PolyA/PolyT linker pair appeared to have the longest half-life, but also had lower overall antibody modification of the cell surface. The GT2/CA2 linker pair appeared to have the shortest half-life, but had a higher initial level of antibody conjugation. Error bars in FIG. 32 indicate standard deviation of at least three replicates.

Figure 33:
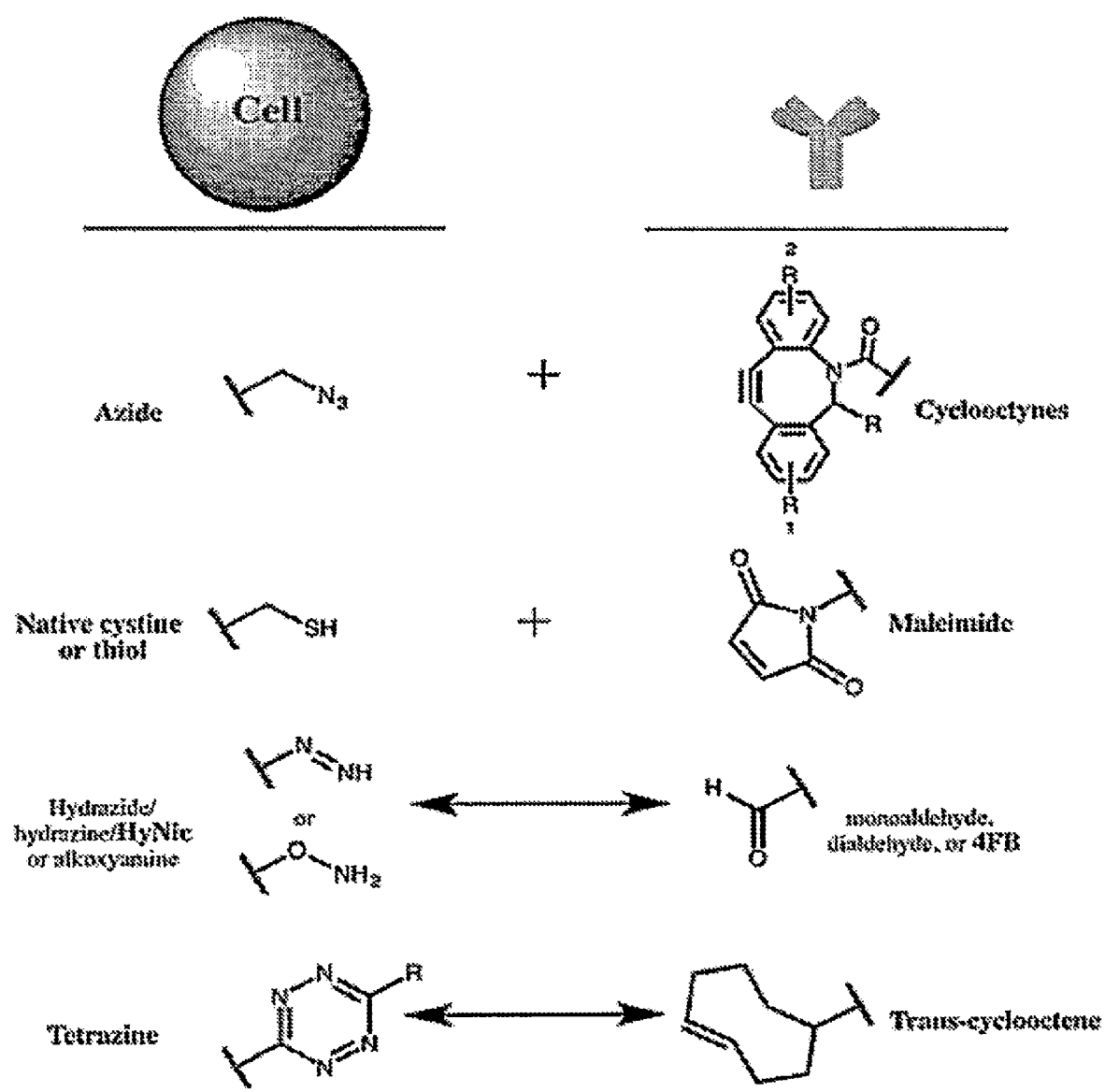
FIG. 33 illustrates schemes for the conjugation of a cell to a targeting moiety, in accordance with some embodiments.
Figure 34:
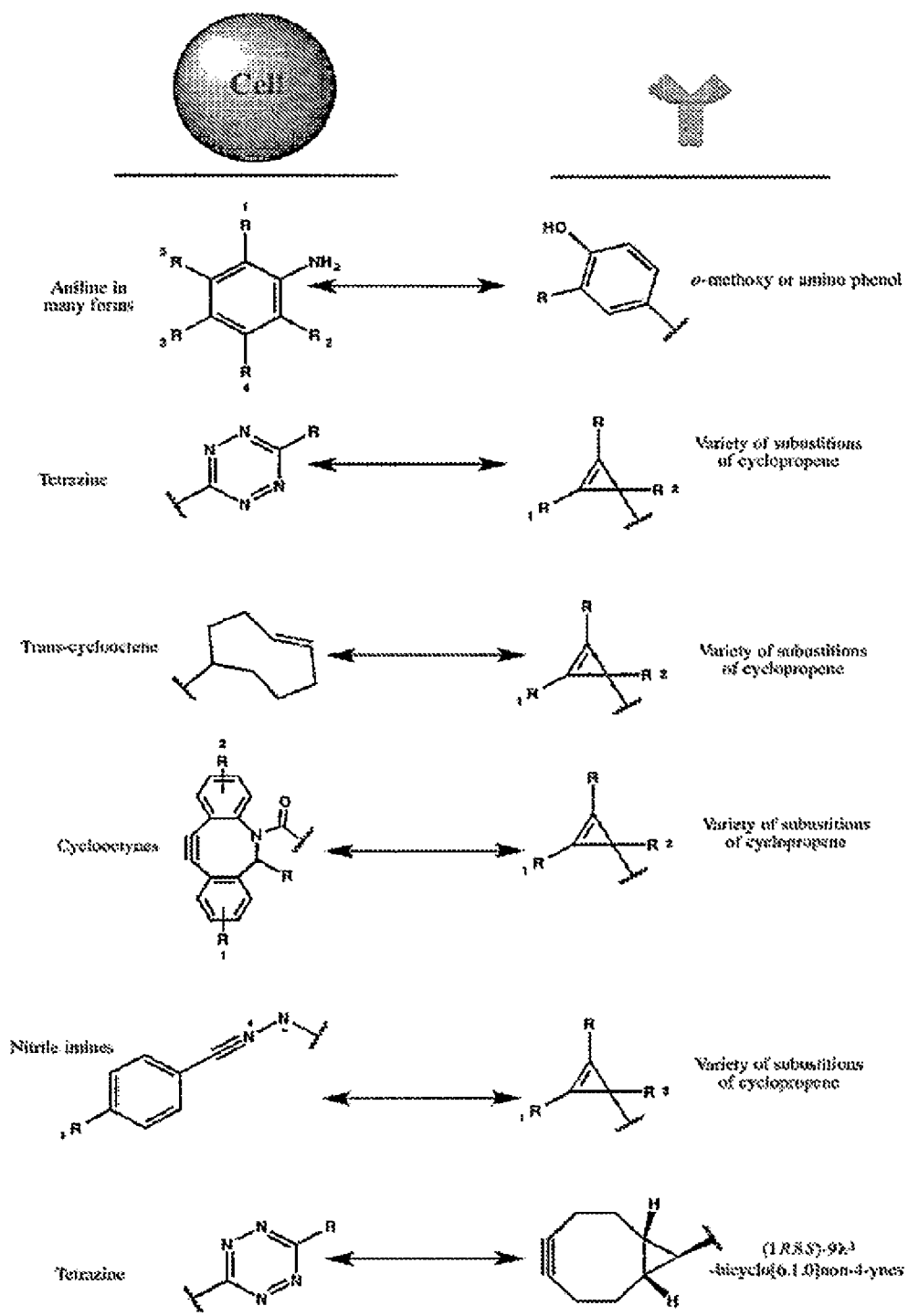
FIG. 34 illustrates schemes for the conjugation of a cell to a targeting moiety, in accordance with some embodiments.

Example 16: Linker Pairs for Covalent Conjugation of Cells to Targeting Moiety In this example, various pairs of reactive groups were used as linkers. One member of a pair was conjugated to a cell and the other was conjugated to an antibody. The cell and antibody were then exposed to one another, such that the reactive groups reacted with one another to directly conjugate the cell to the antibody by covalent attachment. An illustration of this approach and exemplary pairs of reactive groups are provided in FIG. 33. Illustrative reactive group pairs include: (1) azide and cyclooctynes; (2) native cystine or thiol with maleimide; (3) hydrazine/hydrazine/HyNic or alkoxyamine and monoaldehyde, dialdehyde or 4FB; and (4) tetrazine and trans-cyclooctene. In (1) and (2), the first reactive group of the pair is preferred as the group conjugated to cells. In (2) and (3), either member of the pair may be on the cell, while the other is on the targeting moiety (this is denoted by a double-headed arrow in FIG. 33). Additional examples of pairs of reactive groups, with either member of the pair used to modify the cell, are provided in FIG. 34, which illustrates: (5) aniline in many forms and o-methoxy or amino phenol; (6) tetrazine and a variety of substitutions of cyclopropene; (7) trans-cyclooctene and a variety of substitutions of cyclopropene; (8) trans-cyclooctene and a variety of substitutions of cyclopropene; (9) cyclooctynes and a variety of substitutions of cyclopropene; (10) nitrile imines and a variety of substitutions of cyclopropene; tetrazine and (1R,8S)-9$\lambda^3$-bicyclo[6.1.0]non-4-ynes.

Conjugation by covalent linkage between reactive groups followed the following general procedure, scaled for 10 million cells (and scaled proportionally for more cells, if needed). After washing with PBS, cells were suspended in DPBS plus NHS-bioconjugation linker at a final concentration ranging from 150 to 750 µM. Cells were reacted at RT with orbital shaking for 20-25 minutes. After this, the cells were rinsed two times by resuspending in PBS and pelleting via centrifugation. In some cases, a catalyst was explored to enhance modification. Commercially available reagents were tested in these experiments (see compounds listed in bold text in FIG. 33). Other chemistry with fast kinetics could also be explored as alternative ways to form complexes between cells and targeting moieties. Examples are listed in FIG. 34 and may use strain promoted or electron promoted cycloaddition or inverse electron demand Diels Alder reaction.

Figure 35:
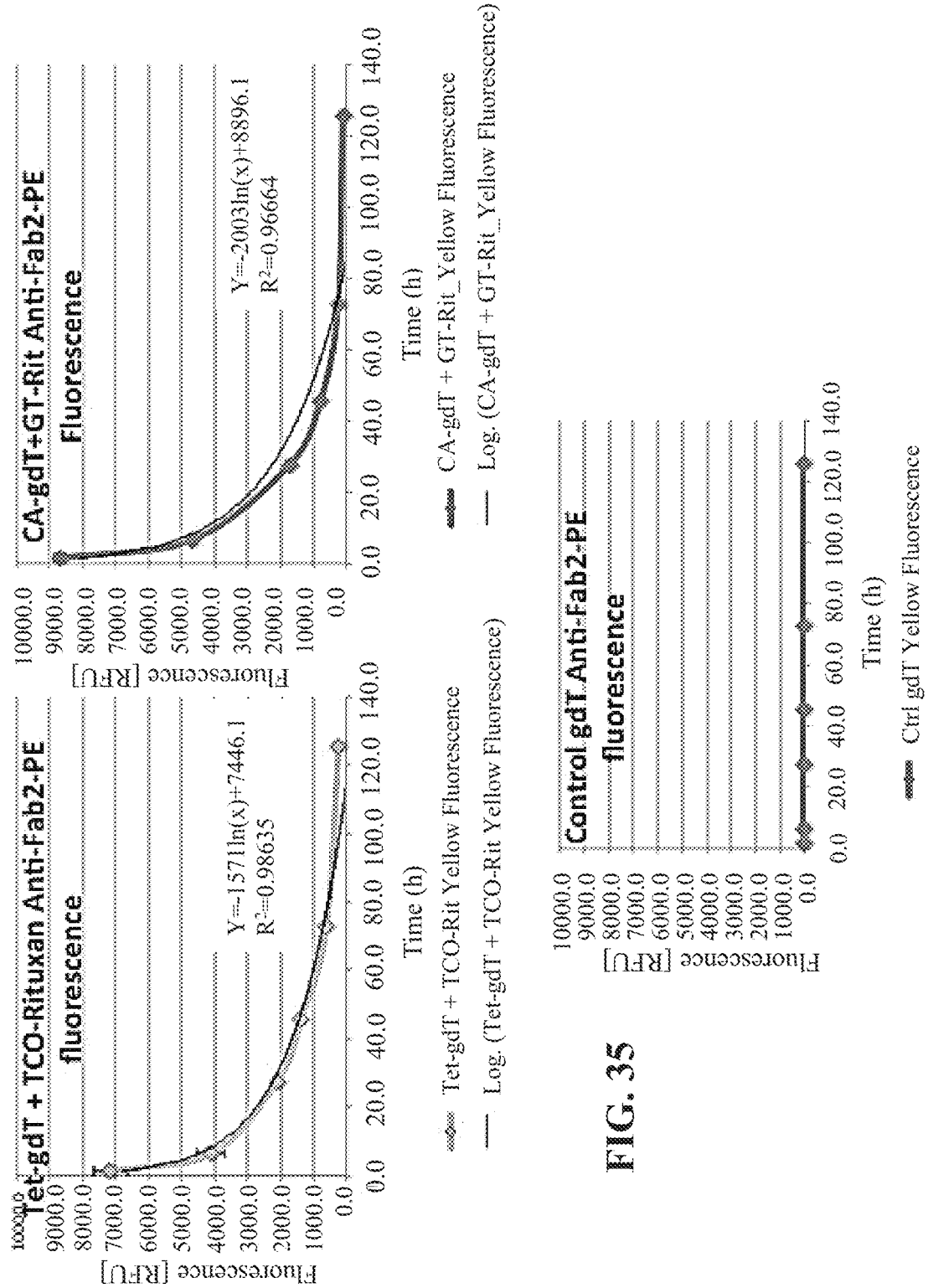
FIG. 35 shows results of an assay for presence of conjugated antibody over time.

For an analysis of conjugate half-life, DNA-linker complexes and reactive group complexes were prepared. gdT-cells complexed to Rituxan by DNA linkers were prepared as in previous examples, using the 20-mer poly-CA/GT (CA/GT) linker pair. gdT-cells conjugated to Rituxan by covalent attachment between reactive groups were prepared as above, using gdT-cells conjugated to tetrazine ("Tet") and Rituxan conjugated to trans-cyclooctene ("TCO"). Half-life was measured as in Example 15, including measurement of control gdT-cells. Results are shown in FIG. 35, with error bars showing standard deviation of at least three replicates.

Figure 36:
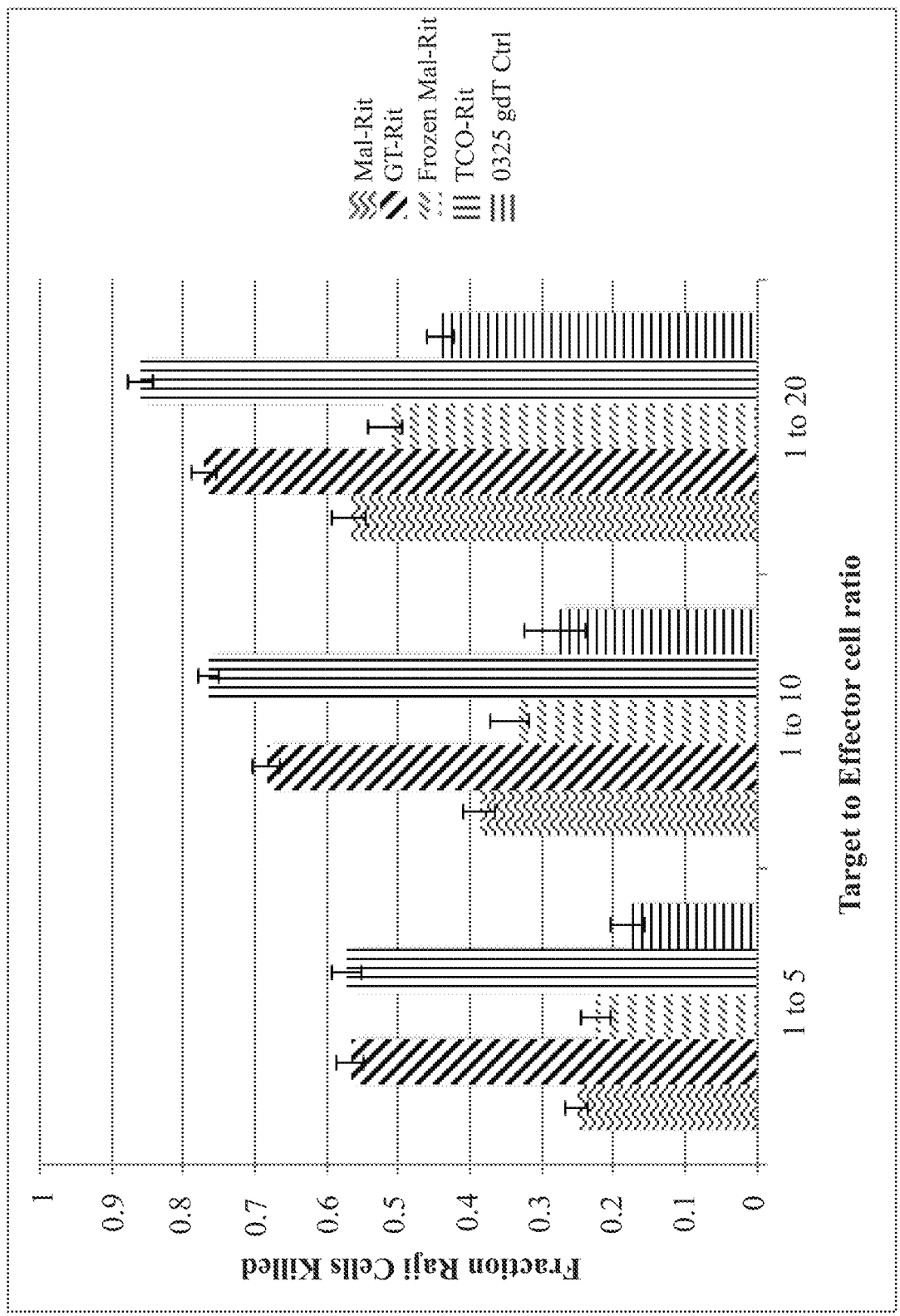
FIG. 36 is a graph showing fraction of Raji cells killed at t=0 after complexing cells with Rituxan. Error bars are standard deviation of 4 replicates.

After modification, the cells conjugated to Rituxan were incubated with Raji cells for a 4 h killing assay, as in Example 10, using different tumor to effector cell ratios performed a day apart. The ratios tested were 1 to 5, 1 to 10, and 1 to 20. Results are illustrated in FIG. 36, with results for each ratio presented in a group of 5 bars, and each bar within a group from left to right corresponding to the groups indicated in the legend from top to bottom, respectively. Groups are indicated by the linker conjugated to Rituxan as maleimide ("Mal-Rit"), DNA linker GT ("GT-Rit"), maleimide that had been frozen and thawed ("Frozen Mal-Rit"), TCO, uncomplexed control cells ("0325 gdT Ctrl"). The DNA linker partner was DNA linker CA. The reactive group partners were those indicated in FIG. 33. In all cases, the killing of target Raji cells was increased by the various methods for forming covalent or DNA-based complexes compared to unmodified gdT. The frozen maleimide-Rituxan modified cells (Frozen Mal-Rit) had a slightly higher number of antibodies per cell based on the Anti-Fab-PE data. The killing was slightly higher for gdT modified with maleimide-Rituxan (Mal-Rit) that was stored at 4° C. vs. frozen. The results for maleimide-conjugated Rituxan demonstrate that cell surface thiols can be directly modified with such antibody conjugates.

Figure 37:
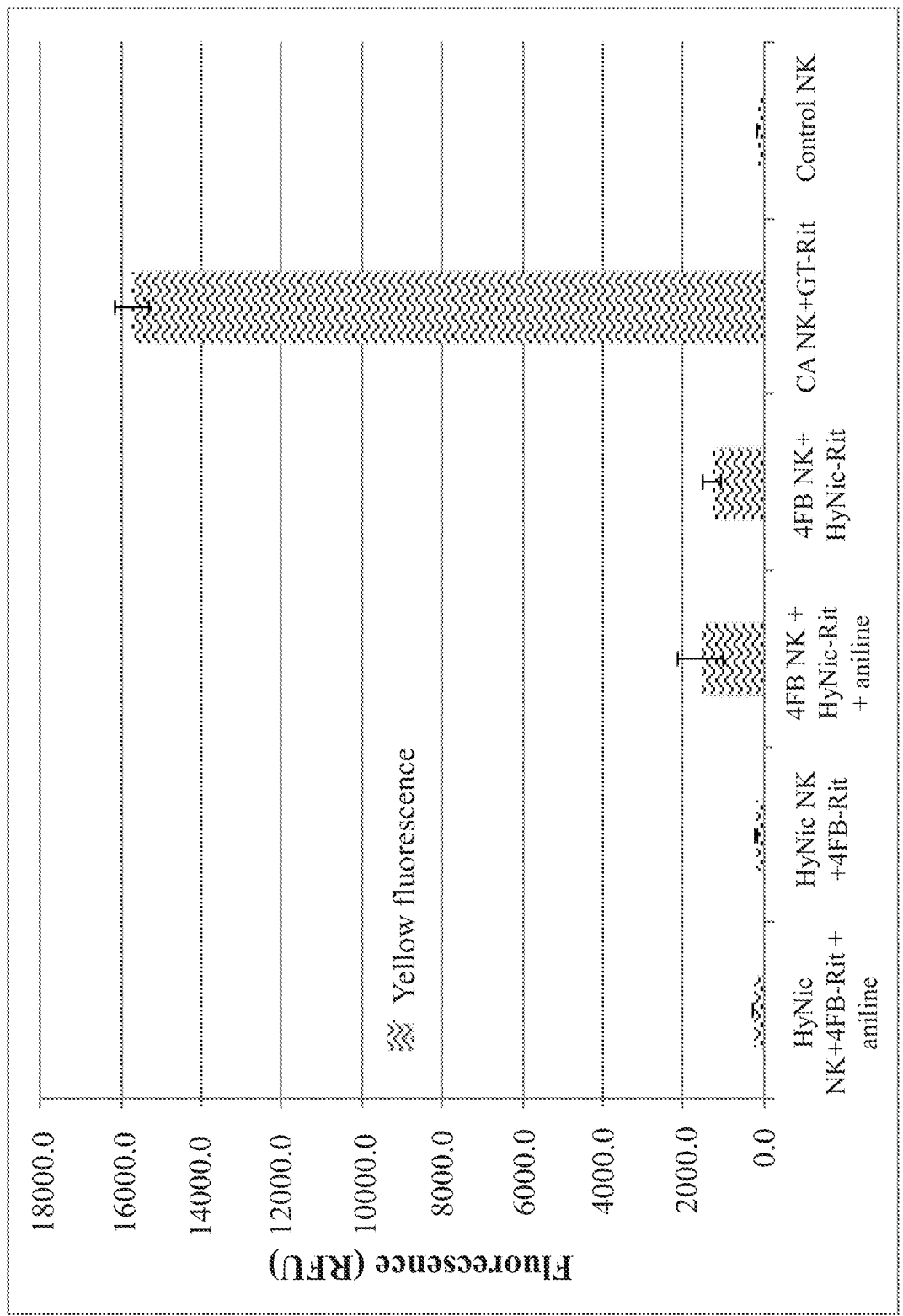
FIG. 37 is a graph showing relative level of antibody-cell complex formation for different linkers of the disclosure.

Labeling efficiency for various linkers and complex-formation conditions were also compared. Results are illustrated in FIG. 37. NK cells were complexed to Rituxan by: (1) HyNic-conjugated cells exposed to 4FB-PEG$_4$-conjugated Rituxan ("HyNic NK+4FB-Rit"), with or without 0.5 mM aniline catalysis; (2) 4FB-conjugated cells exposed to HyNic-conjugated Rituxan ("4FB NK+HyNic-Rit"), with or without 0.5 mM aniline catalysis; and (3) CA DNA-conjugated cells and GT DNA-conjugated Rituxan ("CA NK+GT-Rit"). Cell surface antibody quantification at zero hours after complex formation was determined by anti-Fab-PE labeling and flow-cytometry fluorescence detection. Results are presented below in Table 3. Error bars in FIG. 37 represent standard deviation of at least 3 replicates. Results indicate that degree of antibody labeling via reactive group pairs is also tunable.

TABLE 3

| Sample | Red Fluor | Avg Rit/cell |
|---|---|---|
| HyNic NK + 4FB-Rit + aniline | 70 | 6,535 |
| HyNic NK + 4FB-Rit | 59 | 5,446 |
| 4FB NK + HyNic-Rit + aniline | 173 | 16,764 |
| 4 FB NK + HyNic-Rit | 145 | 13,931 |
| CA NK + GT-Rit | 1359 | 142,960 |
| Control NK | 69 | 6,480 |

Example 17: Improved Efficacy of Complexed T-Cells in Treating Solid Tumors

Figure 38:
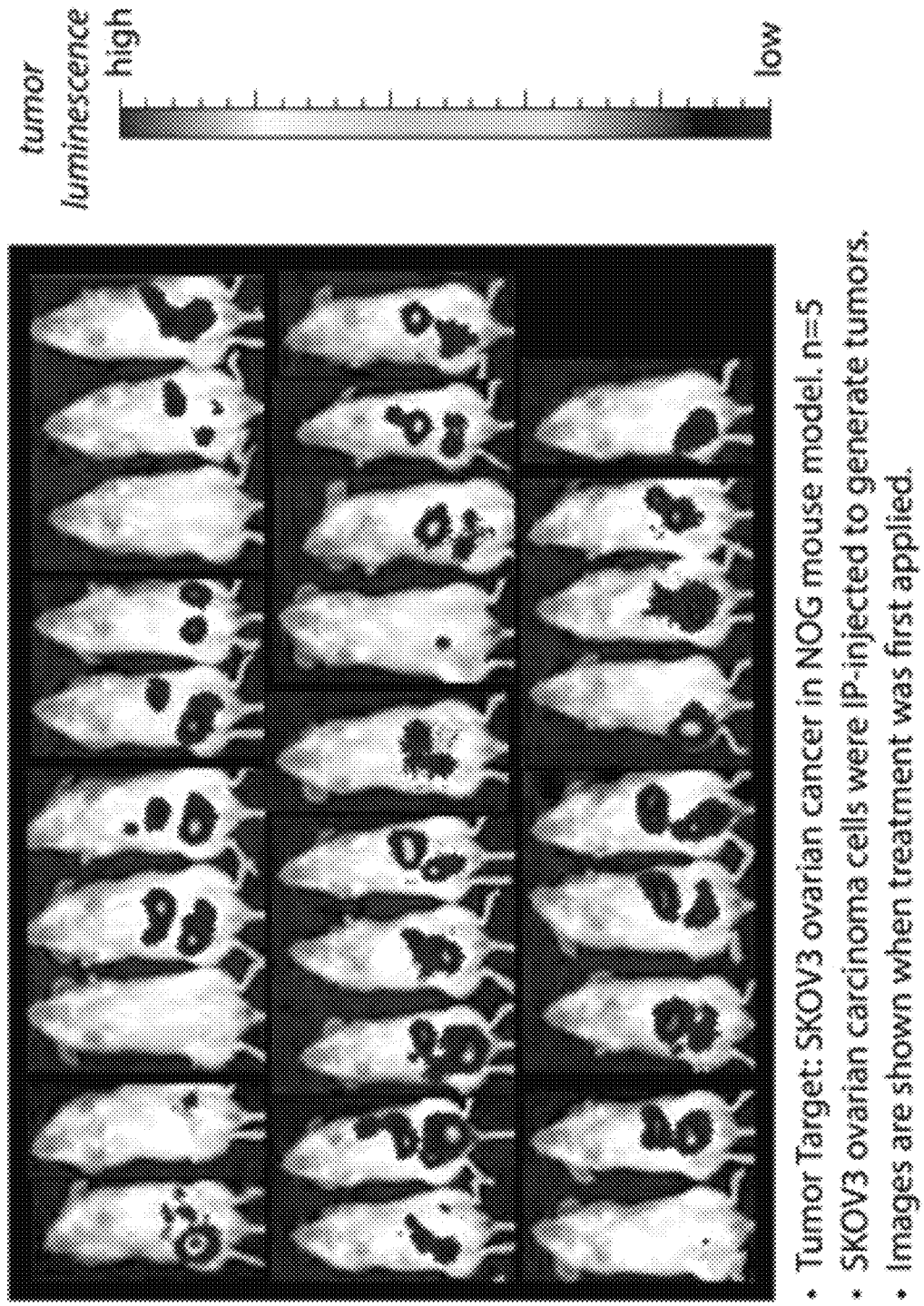
FIG. 38 provides an illustration of fluorescence from cancer cells in mice.
Figure 39:
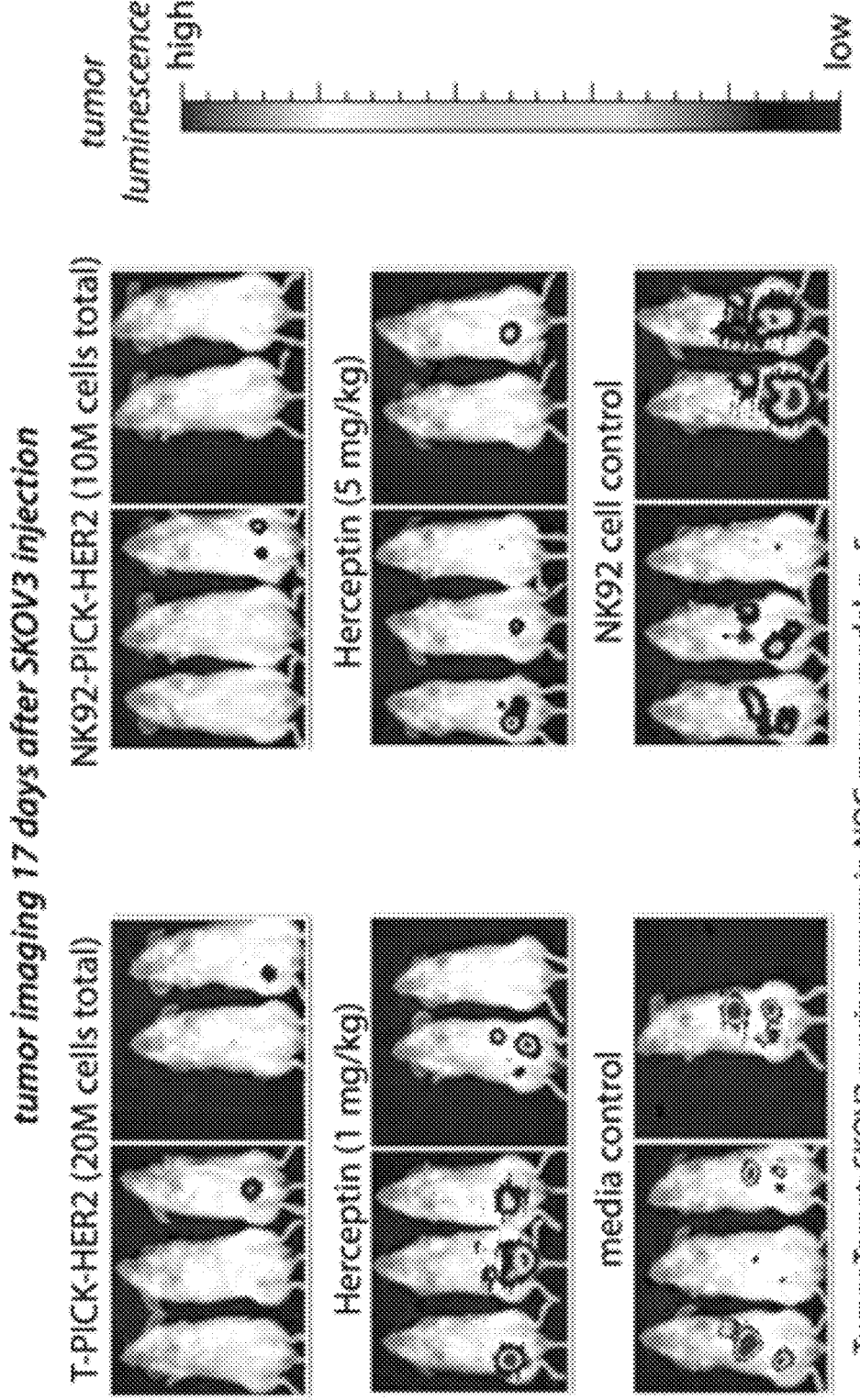
FIG. 39 provides an illustration of fluorescence from cancer cells in mice.
Figure 40:
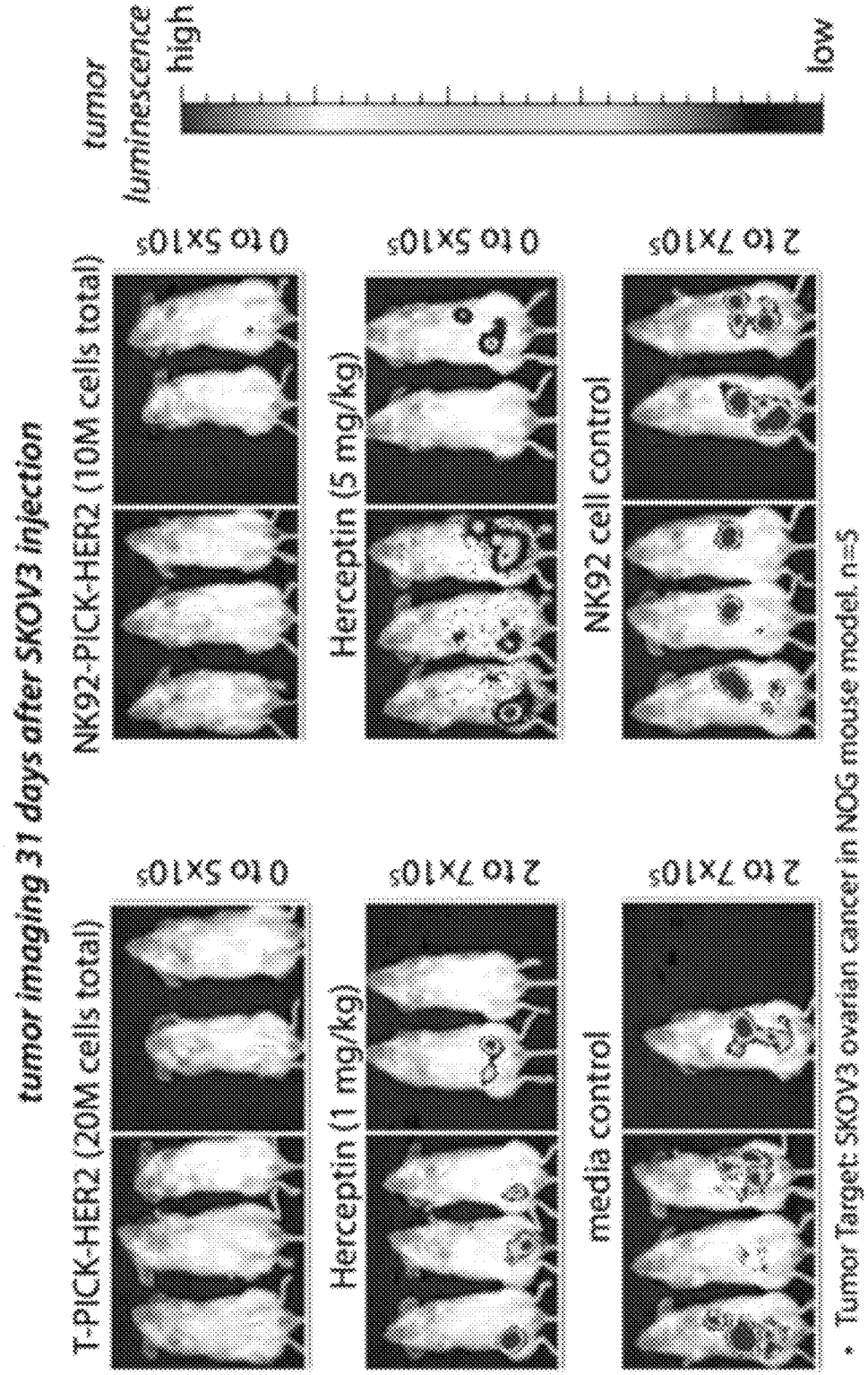
FIG. 40 provides an illustration of fluorescence from cancer cells in mice.
Figure 41:
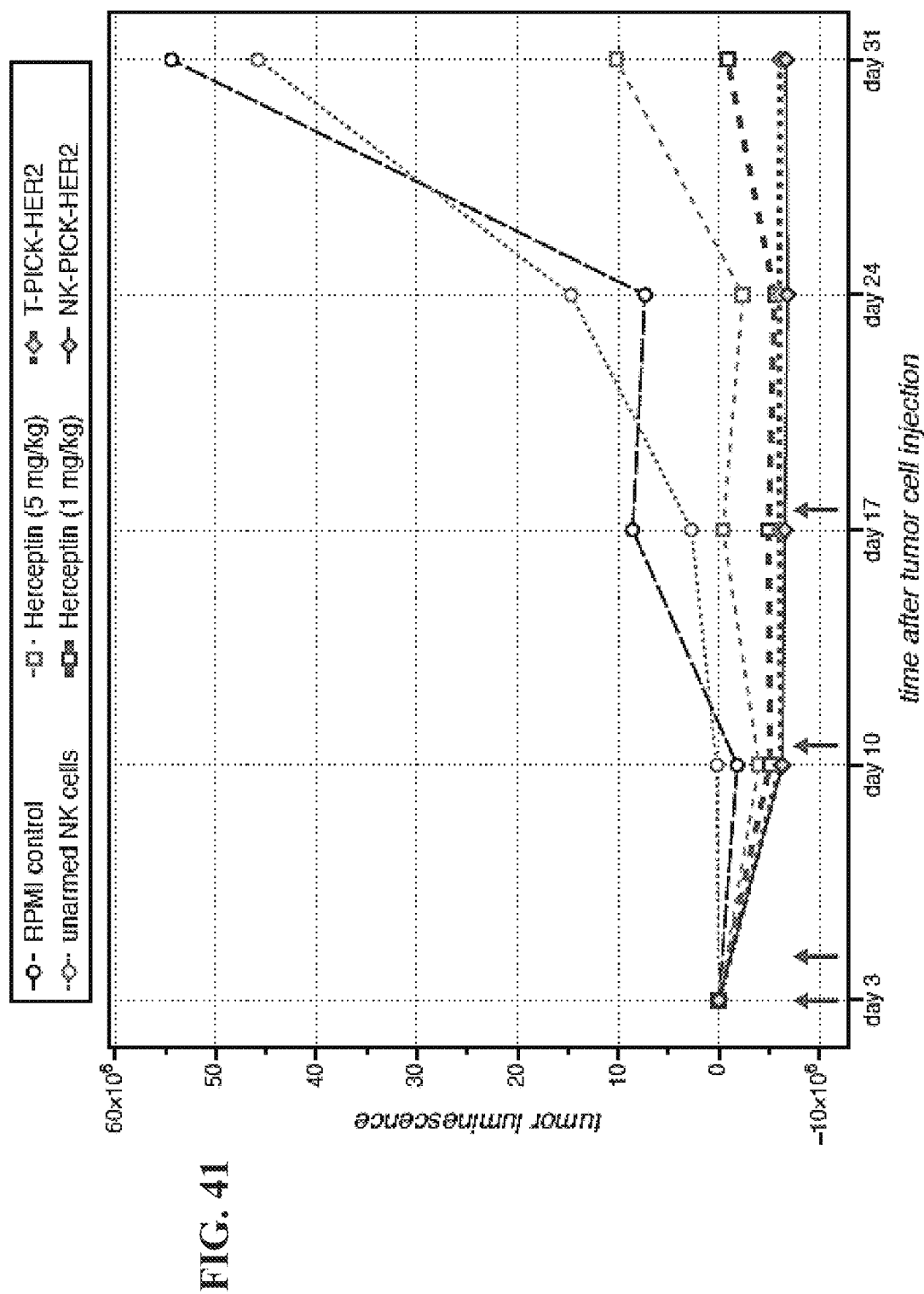
FIG. 41 is a graph plotting fluorescence from cancer cells in mice over time.

T-cells and NK92 cells were complexed with an anti-Her2 antibody using DNA linkers, similar to the procedure in Example 3. Efficacy of these conjugates (T-PICK-HER2 and NK92-PICK-HER2, respectively) was assessed in a mouse model of ovarian cancer, and compared to treatment with herceptin alone, NK92 control cells, and media-only controls. SKOV3 ovarian carcinoma cells were IP-injected into NOG mice (5 per group) to generate tumors. Mice then received IP injections of either cells, antibodies, or media (depending on group) via IP injection on days 3, 5, 11, and 18. Doses based on group were as follows: (1) 20 million T-cells complexed with anti-Her2; (2) 10 million NK92 cells complexed with anti-Her2; (3) 1 mg/kg herceptin; (4) 5 mg/kg herceptin; (5) media only; (6) NK92 control cells. Fluorescent images of tumor cells when treatment was first applied, on day 17, and on day 31 are shown in FIG. 38, FIG. 39, and FIG. 40, respectively. A plot of cancel cell fluorescence over time for each of the groups is provided in FIG. 41. Cell-antibody complexes were the most effective, and showed the lowest level of fluorescence.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A live cell comprising a surface and a population of at least about 1000 exogenous targeting units complexed to the surface, wherein an exogenous targeting unit in said population comprises a targeting moiety that is characterized in that:
   (a) it exhibits specific binding to a biological marker on a target cell;
   (b) it is not a nucleic acid; and
   (c) it is not produced by said live cell,
   wherein the exogenous targeting unit is complexed to the surface via an interaction between a first linker conjugated to the targeting moiety and a second linker covalently conjugated to the surface of the live cell.

2. The live cell of claim 1, wherein the first linker is a first polynucleotide.

3. The live cell of claim 2, wherein the targeting moiety comprises an antigen-binding unit.

4. The live cell of claim 2, wherein the first polynucleotide comprises a single-stranded region.

5. The live cell of claim 4, wherein the second linker is a second polynucleotide.

6. The live cell of claim 1, wherein the first linker and the second linker are selected from the group consisting of: a DNA binding domain and a target DNA; a leucine zipper and a target DNA; biotin and avidin; biotin and streptavidin; calmodulin binding protein and calmodulin; a hormone and a hormone receptor; lectin and a carbohydrate; a cell membrane receptor and a receptor ligand; an enzyme and a substrate; an antigen and an antibody; an agonist and an antagonist; polynucleotide hybridizing sequences; an aptamer and a target; and a zinc finger and a target DNA.

7. The live cell of claim 1, wherein the at least 1000 exogenous targeting units comprise at least two different exogenous targeting units, each different exogenous targeting unit exhibiting specific binding to the same or different biological marker.

8. The live cell of claim 1, wherein the first linker comprises a first reactive group, and the second linker comprises a second reactive group, and wherein the cell is complexed to the targeting moiety via a covalent bond formed by a reaction between the second reactive group and the first reactive group.

9. The live cell of claim 8, wherein the targeting moiety comprises an antigen-binding unit.

10. The live cell of claim 8, wherein the second linker comprises a PEG region.

11. The live cell of claim 1, wherein the cell is an effector cell.

12. The live cell of claim 1, wherein the cell is a stem cell.

13. A method of treating cancer, comprising administering to a subject in need thereof a complexed cell that is a live cell of claim 1, wherein (a) the biological marker is on a cancer cell; and (b) the complexed cell induces death of the cancer cells.

14. The method of claim 13, wherein the complexed cell comprises a first type and a second type of exogenous targeting unit complexed to said surface, wherein the first type and the second type each comprise a distinct targeting moiety that (a) is not a nucleic acid, and (b) is not produced by said live cell, and wherein the first type and the second type of exogenous targeting units each bind specifically to a different antigen.

15. A method of inducing cell proliferation in a target tissue, the method comprising administering to a subject in need thereof a complexed cell that is a live cell of claim 1, wherein (a) the live cell is delivered to the target tissue via the targeting moiety specifically binding to the biological marker; and (b) the complexed cell proliferates in the target tissue.

16. The method of claim 15, wherein the complexed cell comprises a first type and a second type of exogenous targeting unit complexed to said surface, wherein the first type and the second type each comprise a distinct targeting moiety that (a) is not a nucleic acid, and (b) is not produced by said live cell, and wherein the first type and the second type of exogenous targeting units each bind specifically to a different antigen.

17. The method of claim 13, wherein the live cell is an effector cell obtained from the subject.

18. The method of claim 17, wherein the complexed cell is administered without inducing cell expansion prior to administration.

19. The method of claim 13, wherein the live cell is a stem cell.

20. The method of claim 19, wherein the complexed cell is administered without inducing cell expansion prior to administration.

21. The live cell of claim 1, wherein said targeting unit and said live cell are separated by a length of 1 nm to 400 nm.

22. The live cell of claim 1, wherein the said exogenous targeting unit comprises an antigen-binding unit, and the antigen-binding unit binds to a cancer antigen, glycolipid, glycoprotein, cluster of differentiation antigen present on cells of a hematopoietic lineage, gamma-glutamyltranspeptidase, adhesion protein, hormone, growth factor, cytokine, ligand receptor, ion channel, membrane-bound form of an immunoglobulin μ, chain, alfa-fetoprotein, C-reactive protein, chromogranin A, epithelial mucin antigen, human epithelium specific antigen, Lewis(a) antigen, multidrug resistance related protein, Neu oncogene protein, neuron specific enolase, P-glycoprotein, multidrug-resistance-related antigen, p170, multidrug-resistance-related antigen, prostate specific antigen, NCAM, ganglioside molecule, MART-1, heat shock protein, sialyl Tn, tyrosinase, MUC-1, HER-2/neu, KSA, PSMA, p53, RAS, EGF-R, VEGF, or MAGE.

23. The live cell of claim 2, wherein the targeting moiety is conjugated to the first polynucleotide using a coupling group, wherein the coupling group is an NHS ester, other activated ester, an alkyl or acyl halide, a bifunctional cross-linker, or maleimide group.

24. The live cell of claim 5, wherein the first polynucleotide or second polynucleotide comprise a sequence selected from 20-mer poly-CA, 20-mer poly-GGTT, SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, and SEQ ID NO: 28.

25. The live cell of claim 1, the binding affinity of the targeting moiety for the biological marker is less than 250 nM.

26. The live cell of claim 5, the length of the first polynucleotide and the length of the second polynucleotide are 4 nt to 500 nt.

27. The live cell of claim 1, the binding affinity between the first linker and the second linker is less than 250 nM.

28. The live cell of claim 1, the live cell is an effector cell, immune cell, bacterial cell, cardiomyocyte, gd T cell, Cytokine Induced Killer, macrophage, neutrophil, natural killer T cell, primary cell, cytolytic T cell, killer cell, natural killer cell, monocyte, eosinophil, polymorphonuclear cell, granulocytes, mast cell, basophil, dendritic cell, B cell, T cell, antigen presenting cell, stem cell, cancer cell, transgenic cell, primary cell, cell lines, cells from endocrine system, committed progenitors for the blood and immune system (various type), induced pluripotent stem cells, a tumor infiltrating lymphocyte, a lymphocyte-activated killer cell, a pluripotent stem cell, a totipotent stem cell, or a multipotent stem cell.

29. The live cell of claim 10, the first linker or the second linker is conjugated to a native functional group of the targeting unit or the surface of the live cell, wherein the native functional group is an amino acid, a sugar, or an amine.

30. The live cell of the claim 1, the targeting moiety is a peptide, protein, or aptamer.

31. The live cell of claim 19, wherein said targeting unit and said live cell are separated by a length of 1 nm to 20 nm or 1 nm to 33 nm.

32. The live cell of claim 26, wherein the effector cell is a cytotoxic cell, an immune cell, a lymphocyte, a tissue repair cell, an immune-regulatory cell, a tissue regenerate cell, a stem cell, a committed progenitor cell, or a primary cell.

33. The method of claim 13, wherein the first linker is a first polynucleotide.

34. The method of claim 33, wherein the targeting moiety comprises an antigen-binding unit.

35. The method of claim 33, wherein the first polynucleotide comprises a single-stranded region.

36. The method of claim 35, wherein the second linker is a second polynucleotide.

37. The method of claim 13, wherein the first linker and the second linker are selected from the group consisting of: a DNA binding domain and a target DNA; a leucine zipper and a target DNA; biotin and avidin; biotin and streptavidin; calmodulin binding protein and calmodulin; a hormone and a hormone receptor; lectin and a carbohydrate; a cell membrane receptor and a receptor ligand; an enzyme and a substrate; an antigen and an antibody; an agonist and an antagonist; polynucleotide hybridizing sequences; an aptamer and a target; and a zinc finger and a target DNA.

38. The method of claim 13, wherein the at least 1000 exogenous targeting units comprise at least two different exogenous targeting units, each different exogenous targeting unit exhibiting specific binding to the same or different biological marker.

39. The method of claim 13, wherein the first linker comprises a first reactive group, and the second linker comprises a second reactive group, and wherein the cell is complexed to the targeting moiety via a covalent bond formed by a reaction between the second reactive group and the first reactive group.

40. The method of claim 39, wherein the targeting moiety comprises an antigen-binding unit.

41. The method of claim 39, wherein the second linker comprises a PEG region.

42. The method of claim 13, wherein said targeting unit and said live cell are separated by a length of 1 nm to 400 nm.

43. The method of claim 13, wherein the said exogenous targeting unit comprises an antigen-binding unit, and the antigen-binding unit binds to a cancer antigen, glycolipid, glycoprotein, cluster of differentiation antigen present on cells of a hematopoietic lineage, gamma-glutamyltranspeptidase, adhesion protein, hormone, growth factor, cytokine, ligand receptor, ion channel, membrane-bound form of an immunoglobulin µ chain, alfa-fetoprotein, C-reactive protein, chromogranin A, epithelial mucin antigen, human epithelium specific antigen, Lewis(a) antigen, multidrug resistance related protein, Neu oncogene protein, neuron specific enolase, P-glycoprotein, multidrug-resistance-related antigen, p170, multidrug-resistance-related antigen, prostate specific antigen, NCAM, ganglioside molecule, MART-1, heat shock protein, sialyl Tn, tyrosinase, MUC-1, HER-2/neu, KSA, PSMA, p53, RAS, EGF-R, VEGF, or MAGE.

44. The method of claim 33, wherein the targeting moiety is conjugated to the first polynucleotide using a coupling group, wherein the coupling group is an NHS ester, other activated ester, an alkyl or acyl halide, a bifunctional crosslinker, or maleimide group.

45. The method of claim 36, wherein the first polynucleotide or second polynucleotide comprise a sequence selected from 20-mer poly-CA, 20-mer poly-GGTT, SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, and SEQ ID NO: 28.

46. The method of claim 13, the binding affinity of the targeting moiety for the biological marker is less than 250 nM.

47. The method of claim 36, the length of the first polynucleotide and the length of the second polynucleotide are 4 nt to 500 nt.

48. The method of claim 13, the binding affinity between the first linker and the second linker is less than 250 nM.

49. The method of claim 13, the live cell is an effector cell, immune cell, bacterial cell, cardiomyocyte, gd T cell, Cytokine Induced Killer, macrophage, neutrophil, natural killer T cell, primary cell, cytolytic T cell, killer cell, natural killer cell, monocyte, eosinophil, polymorphonuclear cell, granulocytes, mast cell, basophil, dendritic cell, B cell, T cell, antigen presenting cell, stem cell, cancer cell, transgenic cell, primary cell, cell lines, cells from endocrine system, committed progenitors for the blood and immune system (various type), induced pluripotent stem cells, a tumor infiltrating lymphocyte, a lymphocyte-activated killer cell, a pluripotent stem cell, a totipotent stem cell, or a multipotent stem cell.

50. The method of claim 41, the first linker or the second linker is conjugated to a native functional group of the targeting unit or the surface of the live cell, wherein the native functional group is an amino acid, a sugar, or an amine.

51. The method of claim 13, the targeting moiety is a peptide, protein, or aptamer.

52. The method of claim 42, wherein said targeting unit and said live cell are separated by a length of 1 nm to 20 nm or 1 nm to 33 nm.

53. The method of claim 49, wherein the effector cell is a cytotoxic cell, an immune cell, a lymphocyte, a tissue repair cell, an immune-regulatory cell, a tissue regenerate cell, a stem cell, a committed progenitor cell, or a primary cell.

54. The method of claim 15, wherein the first linker is a first polynucleotide.

55. The method of claim 54, wherein the targeting moiety comprises an antigen-binding unit.

56. The method of claim 54, wherein the first polynucleotide comprises a single-stranded region.

57. The method of claim 56, wherein the second linker is a second polynucleotide.

58. The method of claim 15, wherein the first linker and the second linker are selected from the group consisting of: a DNA binding domain and a target DNA; a leucine zipper and a target DNA; biotin and avidin; biotin and streptavidin; calmodulin binding protein and calmodulin; a hormone and a hormone receptor; lectin and a carbohydrate; a cell membrane receptor and a receptor ligand; an enzyme and a substrate; an antigen and an antibody; an agonist and an antagonist; polynucleotide hybridizing sequences; an aptamer and a target; and a zinc finger and a target DNA.

59. The method of claim 15, wherein the at least 1000 exogenous targeting units comprise at least two different exogenous targeting units, each different exogenous targeting unit exhibiting specific binding to the same or different biological marker.

60. The method of claim 15, wherein the first linker comprises a first reactive group, and the second linker comprises a second reactive group, and wherein the cell is complexed to the targeting moiety via a covalent bond formed by a reaction between the second reactive group and the first reactive group.

61. The method of claim 60, wherein the targeting moiety comprises an antigen-binding unit.

62. The method of claim 60, wherein the second linker comprises a PEG region.

63. The method of claim 15, wherein said targeting unit and said live cell are separated by a length of 1 nm to 400 nm.

64. The method of claim 15, wherein the said exogenous targeting unit comprises an antigen-binding unit, and the antigen-binding unit binds to a cancer antigen, glycolipid, glycoprotein, cluster of differentiation antigen present on cells of a hematopoietic lineage, gamma-glutamyltranspeptidase, adhesion protein, hormone, growth factor, cytokine, ligand receptor, ion channel, membrane-bound form of an immunoglobulin µ chain, alfa-fetoprotein, C-reactive protein, chromogranin A, epithelial mucin antigen, human epithelium specific antigen, Lewis(a) antigen, multidrug resistance related protein, Neu oncogene protein, neuron specific enolase, P-glycoprotein, multidrug-resistance-related antigen, p170, multidrug-resistance-related antigen, prostate specific antigen, NCAM, ganglioside molecule, MART-1, heat shock protein, sialyl Tn, tyrosinase, MUC-1, HER-2/neu, KSA, PSMA, p53, RAS, EGF-R, VEGF, or MAGE.

65. The method of claim 54, wherein the targeting moiety is conjugated to the first polynucleotide using a coupling group, wherein the coupling group is an NHS ester, other activated ester, an alkyl or acyl halide, a bifunctional crosslinker, or maleimide group.

66. The method of claim 57, wherein the first polynucleotide or second polynucleotide comprise a sequence selected from 20-mer poly-CA, 20-mer poly-GGTT, SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, and SEQ ID NO: 28.

67. The method of claim 15, the binding affinity of the targeting moiety for the biological marker is less than 250 nM.

68. The method of claim 57, the length of the first polynucleotide and the length of the second polynucleotide are 4 nt to 500 nt.

69. The method of claim 15, the binding affinity between the first linker and the second linker is less than 250 nM.

70. The method of claim 15, the live cell is an effector cell, immune cell, bacterial cell, cardiomyocyte, gd T cell, Cytokine Induced Killer, macrophage, neutrophil, natural killer T cell, primary cell, cytolytic T cell, killer cell, natural killer cell, monocyte, eosinophil, polymorphonuclear cell, granulocytes, mast cell, basophil, dendritic cell, B cell, T cell, antigen presenting cell, stem cell, cancer cell, transgenic cell, primary cell, cell lines, cells from endocrine system, committed progenitors for the blood and immune system (various type), induced pluripotent stem cells, a tumor infiltrating lymphocyte, a lymphocyte-activated killer cell, a pluripotent stem cell, a totipotent stem cell, or a multipotent stem cell.

71. The method of claim 62, the first linker or the second linker is conjugated to a native functional group of the targeting unit or the surface of the live cell, wherein the native functional group is an amino acid, a sugar, or an amine.

72. The method of claim 15, the targeting moiety is a peptide, protein, or aptamer.

73. The method of claim 63, wherein said targeting unit and said live cell are separated by a length of 1 nm to 20 nm or 1 nm to 33 nm.

74. The method of claim 70, wherein the effector cell is a cytotoxic cell, an immune cell, a lymphocyte, a tissue repair cell, an immune-regulatory cell, a tissue regenerate cell, a stem cell, a committed progenitor cell, or a primary cell.

* * * * *